(12) United States Patent
Tatani et al.

(10) Patent No.: US 8,796,247 B2
(45) Date of Patent: Aug. 5, 2014

(54) INDOLE DERIVATIVE, AND PHARMACOLOGICALLY ACCEPTABLE SALT THEREOF

(75) Inventors: Kazuya Tatani, Nagano (JP); Atsushi Kondo, Nagano (JP); Tatsuhiro Kondo, Niigata (JP); Naohiro Kawamura, Nagano (JP); Shigeki Seto, Nogi (JP); Yasushi Kohno, Nogi (JP)

(73) Assignees: Kissei Pharmaceutical Co., Ltd., Nagano (JP); Kyorin Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 13/980,599

(22) PCT Filed: Jan. 24, 2012

(86) PCT No.: PCT/JP2012/051401
§ 371 (c)(1),
(2), (4) Date: Sep. 5, 2013

(87) PCT Pub. No.: WO2012/102254
PCT Pub. Date: Aug. 2, 2012

(65) Prior Publication Data
US 2014/0018335 A1    Jan. 16, 2014

(30) Foreign Application Priority Data
Jan. 25, 2011    (JP) ................. 2011-012956

(51) Int. Cl.
| C07D 209/08 | (2006.01) |
| A61K 31/40 | (2006.01) |
| A61K 31/4025 | (2006.01) |
| A61K 31/443 | (2006.01) |
| A61K 31/4439 | (2006.01) |
| A61K 31/444 | (2006.01) |
| A61K 45/06 | (2006.01) |
| C07D 401/06 | (2006.01) |
| C07D 401/14 | (2006.01) |
| C07D 405/06 | (2006.01) |
| C07D 405/14 | (2006.01) |
| C07D 409/14 | (2006.01) |
| C07D 413/14 | (2006.01) |
| C07D 417/14 | (2006.01) |
| A61K 31/404 | (2006.01) |

(52) U.S. Cl.
CPC .......... *C07D 209/08* (2013.01); *A61K 31/4025* (2013.01); *A61K 31/404* (2013.01); *C07D 401/06* (2013.01); *C07D 413/14* (2013.01); *C07D 401/14* (2013.01); *C07D 409/14* (2013.01); *A61K 45/06* (2013.01); *C07D 405/06* (2013.01); *A61K 31/4439* (2013.01); *A61K 31/443* (2013.01); *A61K 31/40* (2013.01); *C07D 417/14* (2013.01); *A61K 31/444* (2013.01); *C07D 405/14* (2013.01)

USPC .......... 514/171; 514/333; 514/339; 514/415; 546/256; 546/268.4; 546/268.7; 546/269.4; 546/277.4; 548/465; 548/509

(58) Field of Classification Search
None
See application file for complete search history.

(56) References Cited

U.S. PATENT DOCUMENTS
| 2012/0122931 A1 | 5/2012 | Kondo et al. |
| 2012/0129890 A1 | 5/2012 | Tatani et al. |

FOREIGN PATENT DOCUMENTS
| WO | WO 2008/006790 | 1/2008 |
| WO | WO 2008/006793 | 1/2008 |
| WO | WO 2008/006794 | 1/2008 |
| WO | WO 2008/006795 | 1/2008 |

OTHER PUBLICATIONS

Canadian Patent Application No. 2,825,172, Indole Derivative, and Pharmacologically Acceptable Salt Thereof; National Stage Entry of PCT/JP2012/051401, claiming priority to JP2011-012956, filed Jan. 25, 2011.

(Continued)

*Primary Examiner* — Janet L Andres
*Assistant Examiner* — Timothy R Rozof
(74) *Attorney, Agent, or Firm* — Richard S. Echler

(57) ABSTRACT

The present invention provides a compound represented by the general formula (I) of the present invention, which has $EP_1$ receptor antagonism:

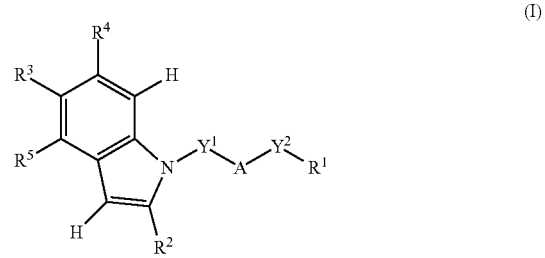

(I)

wherein A represents a pyridine ring, a furan ring, or the like; $Y^1$ represents a $C_{1-6}$ alkylene group; $Y^2$ represents a single bond or the like; $R^1$ represents —C(=O)—NH—$SO_2R^6$, an acidic 5-membered hetero ring group, or the like; $R^2$ represents an optionally substituted phenyl group, an optionally substituted 5-membered aromatic heterocyclic group, or the like; $R^3$ represents a halogen atom, a $C_{1-6}$ alkoxy group, or the like; $R^4$ represents a hydrogen atom, a halogen atom, or the like; $R^5$ represents a hydrogen atom or the like; and $R^6$ represents a $C_{1-6}$ alkyl group or the like], and a pharmaceutically acceptable salt thereof. Furthermore, the compound (I) of the present invention can be used as an agent for treating or preventing LUTS, in particular, various symptoms of OABs.

13 Claims, No Drawings

(56) References Cited

OTHER PUBLICATIONS

Canadian Patent Application No. 2,825,134, Indole Derivative and Pharmacologically Acceptable Salt of Same; National Stage Entry of PCT/JP2012/051402, claiming priority to JP2011-012955, filed Jan. 25, 2011.
European Patent Application No. 12 739 597.8, Indole Derivative, and Pharmacologically Acceptable Salt Thereof; National Stage Entry of PCT/JP2012/051401, claiming priority to JP2011-012956, filed Jan. 25, 2011.
European Patent Application No. 12 739 875.8, Indole Derivative and Pharmacologically Acceptable Salt of Same; National Stage Entry of PCT/JP2012/051402, claiming priority to JP2011-012955, filed Jan. 25, 2011.
Japanese Patent Application No. 2012-554793, Indole Derivative, and Pharmacologically Acceptable Salt Thereof; claiming priority to JP2011-012956, filed Jan. 25, 2011.
Japanese Patent Application No. 2012-554794, Indole Derivative and Pharmacologically Acceptable Salt of Same; National Stage Entry of PCT/JP2012/051402, claiming priority to JP2011-012955, filed Jan. 25, 2011.
Hall, et al., "Discoveery of a novel indole series of EP1 receptor antagonists by scaffold hopping," Bioorganic & Medicinal Chemistry Letters, 18 (2008) 2684-2690.

INDOLE DERIVATIVE, AND PHARMACOLOGICALLY ACCEPTABLE SALT THEREOF

CROSS REFERENCE TO RELATED APPLICATIONS

This Application is a National Stage of PCT/JP2012/051401, filed Jan. 24, 2012, which claims priority to Japanese Patent Application Serial No. 2011-012956, filed Jan. 25, 2011, the entirety of which are incorporated herein by reference.

SEQUENCE LISTING

Incorporated by reference in its entirety is a computer-readable sequence listing submitted concurrently herewith and identified as follows: One 5 KB ASCII (Text) file named "03457_P001U1_Sequence_Listing_ST25.txt."

FIELD

The present invention relates to an indole derivative having an $EP_1$ receptor antagonism, which is useful as a pharmaceutical, or a pharmaceutically acceptable salt thereof, a pharmaceutical composition comprising the same, and a pharmaceutical use thereof.

BACKGROUND

With an increasingly aging and stressed society, the number of patients with lower urinary tract dysfunction (LUTD) has increased. LUTD is a generic term for urine collection disorder and dysuria, and the symptoms derived from LUTD are lower urinary tract symptoms (LUTS). One of the LUTS is an overactive bladder syndrome (OABs). OABs may also be generally called overactive bladder (OAB). In any case, it is a disease defined as "a symptom syndrome which essentially has urinary urgency and which is usually accompanied by urinary frequency and nocturia. Urge urinary incontinence is not necessary". The symptoms associated with OABs interfere with general life activities such as work, daily life, mental activity, and the like, and thus lower the quality of life (QOL). Currently, the first choice drug as an agent for treating OABs is an anticholinergic agent. However, it is necessary for the anticholinergic agent to be used upon sufficient consideration of an anti-muscarinic effect such as thirst and residual urine, and thus the anticholinergic agent is not always effective for all patients (see, for example, Non-patent literature 1). Under these circumstances, there is a demand for development of a therapeutic agent which has a different mechanism from that of the anticholinergic agent (see, for example, Non-patent literature 1).

Recently, in LUTS, particularly in OABs, the role of urothelium has attracted attention. For LUTS, it has become clear that various chemical mediators are released in the urothelial cells, which cause a micturition reflex through the receptors of bladder sensory nerve terminals. Among them, one of the chemical mediators, prostaglandin $E_2$ ($PGE_2$), binds with a prostaglandin E receptor 1 ($EP_1$ receptor) in the afferent nerves (especially C fibers) in the urothelium to increase the micturition reflex. In addition, $PGE_2$ binds with the $EP_1$ receptor present in the bladder smooth muscle to contract the bladder. In fact, it has been reported that the $EP_1$ receptor antagonists inhibit both of the increase in the micturition reflex and the increase in the afferent nerve activities by $PGE_2$ (see, for example, Non-patent literature 2 and Non-patent literature 3). Given the above, it is suggested that $PGE_2$ is involved in contraction of the bladder smooth muscle and increase in the bladder sensory nerves through the $EP_1$ receptors. Furthermore, it is reported that the $EP_1$ receptor antagonists do not increase the amount of the residual urine, but increase the bladder capacity (see, for example, Non-patent literature 4).

There exist four subtypes of the $PGE_2$ receptor: $EP_2$, $EP_3$, and $EP_4$ as well as $EP_1$. The $EP_1$ receptor exists in the lungs as well as the bladder and the urothelium, the skeletal muscle, the renal collecting duct, and the like (see, for example, Non-patent literature 2). Therefore, it is expected that by changing the selectivity of the subtypes of the $PGE_2$ receptor, the target organs of the drugs, or the target tissues, a therapeutic agent for desired diseases can be developed.

As an indole in which the 1-, 2-, and 5-positions are substituted, N,N-dimethyl-1-{[4-(5-methoxy-2-phenyl-1H-indol-1-yl)methyl]benzoyl}pyrrolidin-3-ylamine represented by the chemical structural formula (A), which is an H3 receptor inhibitor, and the like have been described (see, for example, Patent literature 1).

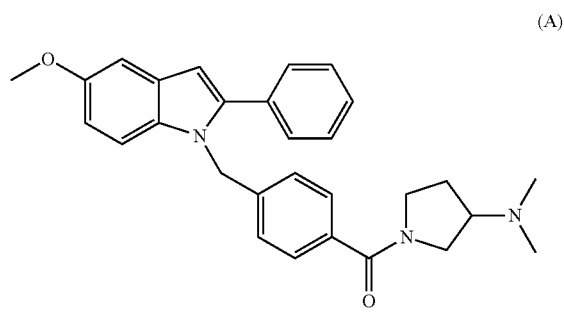

(A)

Further, a compound represented by the general formula (B) having an angiotensin II receptor inhibitory effect has been disclosed (see, for example, Non-patent literature 5).

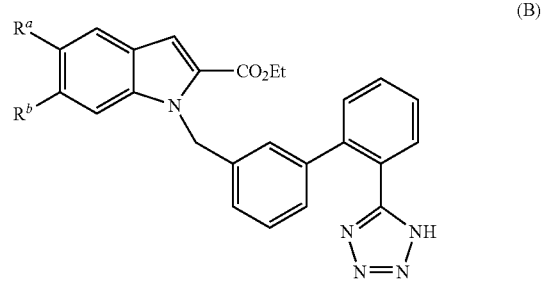

(B)

In the formula B, $R^a$ represents a hydrogen atom or a fluorine atom, and $R^b$ represents a hydrogen atom or a chlorine atom.

However, the chemical structures of these compounds are different from the chemical structure of the compound of the present invention. Further, it is not described or suggested that these compounds have a prostaglandin $EP_1$ receptor antagonism.

A compound represented by the chemical structural formula (C) and the like have been described as an indole derivative having an $EP_1$ receptor antagonism (see, for example, Patent literature 2)

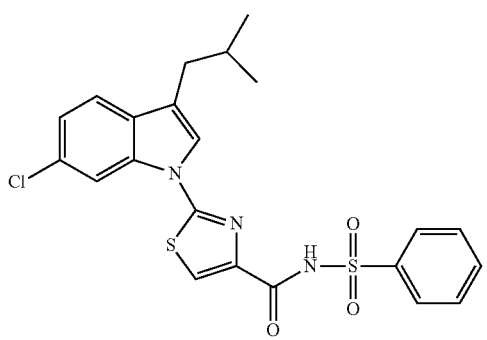

(C)

However, the chemical structure formulae of these compounds are different from the chemical structure formula of the compound of the present invention with respect to the positions, types, and the like of the substituents.

International Publication WO 2007/108936 pamphlet.
International Publication WO 2008/006790 pamphlet.
Narihito Seki, *Folia Pharmacologica Japonica*, 2007, Vol. 129, p. 368-373.
Xiaojun Wang, et al., *Biomedical Research*, 2008, Vol. 29, p. 105-111.
Masahito Kawatani, *PAIN RESEARCH*, 2004, Vol. 19, p. 185-190.
Masanobu Maegawa, *The Journal of The Japan Neurogenic Bladder Society*, 2008, Vol. 19, p. 169.
Richard D. Cramer, et al., *Journal of Medicinal Chemistry*, 1999, Vol. 42, p. 3919-3933.

SUMMARY OF THE DISCLOSURE

An object of the present invention is to provide a compound having an $EP_1$ receptor antagonism or a pharmaceutically acceptable salt thereof, a pharmaceutical composition comprising the same, and a pharmaceutical use thereof.

The present inventors have conducted extensive studies on a compound having an $EP_1$ receptor antagonism, and as a result, they have found that the compound (I) of the present invention or a pharmaceutically acceptable salt thereof exhibits a potent $EP_1$ receptor antagonism, thereby completing the present invention.

That is, the means for solving the above-described objects are presented below.

[1] A compound represented by the general formula (I) or a pharmaceutically acceptable salt thereof:

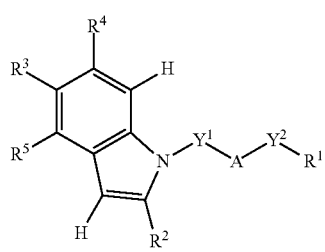

(I)

wherein

A represents a group selected from the group consisting of the following a) to h):

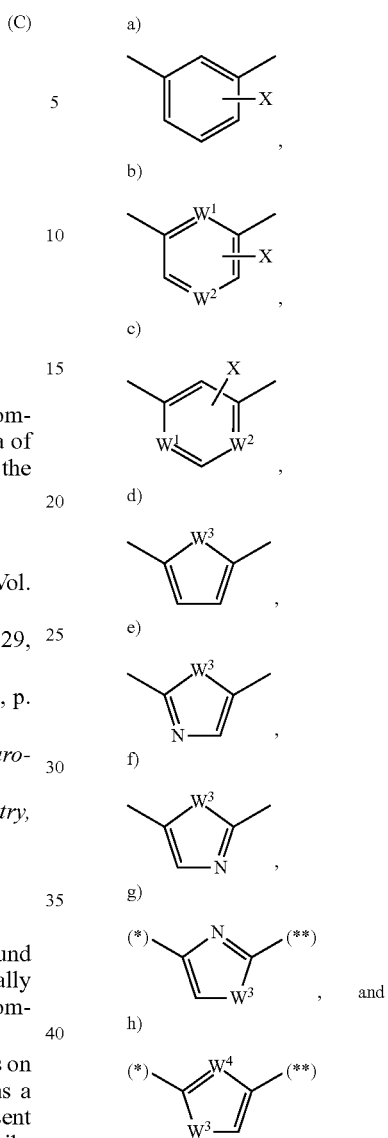

one of $W^1$ and $W^2$ represents a nitrogen atom and the other represents =CH— or a nitrogen atom;
$W^3$ represents an oxygen atom or a sulfur atom;
$W^4$ represents =CH— or a nitrogen atom;
X represents a hydrogen atom or a halogen atom;
$Y^1$ represents a $C_{1-6}$ alkylene group;
$Y^2$ represents a single bond or an oxy-$C_{1-6}$ alkylene group;
$R^1$ represents a group selected from the group consisting of the following i) to n):
 i) —C(=O)—NH—SO$_2$—R$^6$,
 j) —C(=O)—NH—OH,
 k) —C(=O)—NH—CN,
 l) —NH—C(=O)—R$^6$,
 m) an acidic 5-membered hetero ring group, and
 n) a 6-membered aromatic ring group substituted with a phenolic hydroxy group;
$R^2$ represents a group selected from the group consisting of the following o) to t):
 o) a branched $C_{3-6}$ alkyl group,
 p) a halo-$C_{1-6}$ alkyl group,
 q) a $C_{3-6}$ cycloalkyl group, in which the ring is unsubstituted or substituted with one $C_{1-6}$ alkyl group, r) a phenyl group, in which the ring is unsubstituted or substituted with one to five groups independently selected from the group consisting of the following: a halogen atom, a $C_{1-6}$ alkyl group, a halo-$C_{1-6}$ alkyl group, a hydroxy-$C_{1-6}$ alkyl group, a $C_{1-6}$ alkoxy group, and a cyano group, s) a 6-membered aromatic heterocyclic group, in which the ring is unsubstituted or substituted with one to four groups independently selected from the group consisting of the following: a halogen atom, a $C_{1-6}$ alkyl group, a halo-$C_{1-6}$ alkyl group, a hydroxy-$C_{1-6}$ alkyl group, a $C_{1-6}$ alkoxy group, and a cyano group, and t) a 5-membered aromatic heterocyclic group, in which the ring is unsubstituted or substituted with one to three groups independently selected from the group consisting of the following: a halogen atom, a $C_{1-6}$ alkyl group, a halo-$C_{1-6}$ alkyl group, a hydroxy-$C_{1-6}$ alkyl group, a $C_{1-6}$ alkoxy group, and a cyano group;

$R^3$ represents a halogen atom, a $C_{1-6}$ alkyl group, a halo-$C_{1-6}$ alkyl group, a hydroxy-$C_{1-6}$ alkyl group, a $C_{1-6}$ alkoxy group, a halo-$C_{1-6}$ alkoxy group, a $C_{1-6}$ alkylsulfanyl group, a $C_{3-6}$ cycloalkyl group, a cyano group, an amino group, or a nitro group;

$R^4$ represents a hydrogen atom, a halogen atom, a $C_{1-6}$ alkyl group, or a $C_{1-6}$ alkoxy group;

$R^5$ represents a hydrogen atom, a halogen atom, a $C_{1-6}$ alkyl group, or a $C_{1-6}$ alkoxy group;

$R^6$ represents a group selected from the group consisting of the following u) to x):

u) a $C_{1-6}$ alkyl group, v) a halo-$C_{1-6}$ alkyl group, w) a $C_{3-6}$ cycloalkyl group, and x) a phenyl group, in which the ring is unsubstituted or substituted with one to five groups independently selected from the group consisting of the following: a halogen atom, a $C_{1-6}$ alkyl group, a halo-$C_{1-6}$ alkyl group, and a $C_{1-6}$ alkoxy group (with the proviso that the bonds with (*) represent binding to $Y^1$; and the bonds with (**) represent binding to $Y^2$)].

[2] The compound as set forth in [1] or a pharmaceutically acceptable salt thereof, wherein A represents a group selected from the group consisting of the following a), b), d), and h):

a)

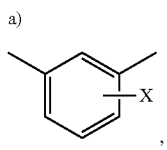

b)

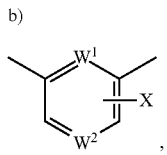

d)

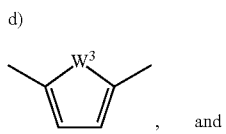

, and h)

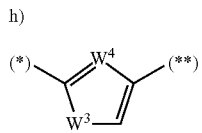

$Y^2$ represents a single bond; and $R^5$ represents a hydrogen atom (with the proviso that the bond with (*) represents binding to $Y^1$; and the bond with (**) represents binding to $Y^2$).

[3] The compound as set forth in [2] or a pharmaceutically acceptable salt thereof, wherein A represents a group selected from the group consisting of the following a), b), and d):

a)

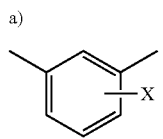

b)

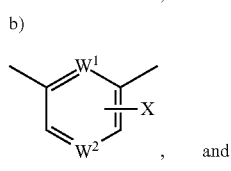

, and d)

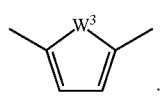

.

[4] The compound as set forth in [3] or a pharmaceutically acceptable salt thereof, wherein $R^2$ is a group selected from the group consisting of the following o), r1), s1) and t1):

o) a branched $C_{3-6}$ alkyl group, r1) a phenyl group, in which the ring is unsubstituted or substituted with one group selected from the group consisting of the following: a halogen atom, a $C_{1-6}$ alkyl group, a halo-$C_{1-6}$ alkyl group, and a $C_{1-6}$ alkoxy group, s1) a 6-membered aromatic heterocyclic group, in which the ring is unsubstituted or substituted with one group selected from the group consisting of the following: a halogen atom, a $C_{1-6}$ alkyl group, a halo-$C_{1-6}$ alkyl group, and a $C_{1-6}$ alkoxy group, and t1) a 5-membered aromatic heterocyclic group, in which the ring is unsubstituted or substituted with one group selected from the group consisting of the following: a halogen atom, a $C_{1-6}$ alkyl group, a halo-$C_{1-6}$ alkyl group, and a $C_{1-6}$ alkoxy group.

[5] The compound as set forth in [4] or a pharmaceutically acceptable salt thereof, wherein $R^3$ is a halogen atom, a $C_{1-6}$ alkyl group, a $C_{1-6}$ alkoxy group, or a $C_{3-6}$ cycloalkyl group.

[6] The compound as set forth in [5] or a pharmaceutically acceptable salt thereof, wherein $R^1$ is a group selected from the group consisting of the following i) and m):

i) —C(=O)—NH—SO$_2$—R$^6$; and m) an acidic 5-membered hetero ring group.

[7] The compound as set forth in [6] or a pharmaceutically acceptable salt thereof, wherein $R^1$ is —C(=O)—NH—SO$_2$—R$^6$.

[8] The compound as set forth in [1], which is the compound selected from the following group, or a pharmaceutically acceptable salt thereof:

N-(methanesulfonyl)-6-(5-methoxy-2-phenylindol-1-ylmethyl)pyridine-2-carboxamide,
6-[6-fluoro-5-methoxy-2-(thiophen-3-yl)indol-1-ylmethyl]-N-(methanesulfonyl)pyridine-2-carboxamide,
6-(6-chloro-5-methoxy-2-phenylindol-1-ylmethyl)-N-(ethanesulfonyl)pyridine-2-carboxamide,
N-(ethanesulfonyl)-6-(5-methoxy-2-phenylindol-1-ylmethyl)pyridine-2-carboxamide,
5-methoxy-2-phenyl-1-[6-(1H-1,2,3,4-tetrazol-5-yl)pyridin-2-ylmethyl]-1H-indole,
5-methoxy-2-phenyl-1-[5-(1H-1,2,3,4-tetrazol-5-yl)furan-2-ylmethyl]-1H-indole,
6-chloro-5-methoxy-2-phenyl-1-[6-(1H-1,2,3,4-tetrazol-5-yl)pyridin-2-ylmethyl]-1H-indole,
6-fluoro-5-methoxy-1-[6-(1H-1,2,3,4-tetrazol-5-yl)pyridin-2-ylmethyl]-2-(thiophen-3-yl)-1H-indole,
6-[2-(butan-2-yl)-6-chloro-5-methoxyindol-1-ylmethyl]-N-(ethanesulfonyl)pyridine-2-carboxamide,
6-[2-(2,5-difluorophenyl)-5-methoxyindol-1-ylmethyl]-N-(ethanesulfonyl)pyridine-2-carboxamide,
6-[2-(butan-2-yl)-5-methoxyindol-1-ylmethyl]-N-(ethanesulfonyl)pyridine-2-carboxamide,
6-(5-methoxy-2-phenylindol-1-ylmethyl)-N-(propane-1-sulfonyl)pyridine-2-carboxamide,
6-(5-methoxy-2-phenylindol-1-ylmethyl)-N-(propane-2-sulfonyl)pyridine-2-carboxamide,
N-(cyclopropanesulfonyl)-6-(5-methoxy-2-phenylindol-1-ylmethyl)pyridine-2-carboxamide,
6-[2-(butan-2-yl)-5-methoxyindol-1-ylmethyl]-N-(propane-1-sulfonyl)pyridine-2-carboxamide,
6-[2-(butan-2-yl)-5-methoxyindol-1-ylmethyl]-N-(propane-2-sulfonyl)pyridine-2-carboxamide,
6-[2-(butan-2-yl)-5-methoxyindol-1-ylmethyl]-N-(cyclopropanesulfonyl)pyridine-2-carboxamide,
6-(6-fluoro-5-methoxy-2-phenylindol-1-ylmethyl)-N-(methanesulfonyl)pyridine-2-carboxamide,
N-(ethanesulfonyl)-6-(6-fluoro-5-methoxy-2-phenylindol-1-ylmethyl)pyridine-2-carboxamide,
6-(6-fluoro-5-methoxy-2-phenylindol-1-ylmethyl)-N-(propane-1-sulfonyl)pyridine-2-carboxamide,
N-(cyclopropanesulfonyl)-6-(6-fluoro-5-methoxy-2-phenylindol-1-ylmethyl)pyridine-2-carboxamide,
2-(butan-2-yl)-5-methoxy-1-[6-(1H-1,2,3,4-tetrazol-5-yl)pyridin-2-ylmethyl]-1H-indole,
6-fluoro-5-methoxy-2-phenyl-1-[6-(1H-1,2,3,4-tetrazol-5-yl)pyridin-2-ylmethyl]-1H-indole,
6-chloro-2-(furan-3-yl)-5-methoxy-1-[6-(1H-1,2,3,4-tetrazol-5-yl)pyridin-2-ylmethyl]-1H-indole,
5-methoxy-2-(1-methylcyclopropyl)-1-[6-(1H-1,2,3,4-tetrazol-5-yl)pyridin-2-ylmethyl]-1H-indole,
6-chloro-5-methoxy-2-(1-methylcyclopropyl)-1-[6-(1H-1,2,3,4-tetrazol-5-yl)pyridin-2-ylmethyl]-1H-indole,
5-methoxy-2-(1-methylcyclopropyl)-1-[5-(1H-1,2,3,4-tetrazol-5-yl)furan-2-ylmethyl]-1H-indole,
3-[6-(6-fluoro-5-methoxy-2-phenylindol-1-ylmethyl)pyridin-2-yl]-4,5-dihydro-1,2,4-oxadiazol-5-one, and
N-cyano-6-(6-fluoro-5-methoxy-2-phenylindol-1-ylmethyl) pyridine-2-carboxamide.

[9] A pharmaceutical composition comprising the compound as set forth in any one of [1] to [8] or a pharmaceutically acceptable salt thereof

[10] The pharmaceutical composition as set forth in [9], comprising a combination of at least one agent selected from the group consisting of the following:

An anticholinergic agent, an $\alpha_1$ antagonist, a $\beta$ agonist, a 5$\alpha$-reductase inhibitor, a PDE inhibitor, an acetylcholine esterase inhibitor, an anti-androgen, a progesterone-based hormone, an LH-RH analog, a neurokinin inhibitor, an anti-diuretic, a calcium channel blocker, a direct smooth muscle agonist, a tricyclic antidepressant, a potassium channel modulator, a sodium channel blocker, an $H_1$ blocker, a serotonin reuptake inhibitor, a norepinephrine reuptake inhibitor, a dopamine reuptake inhibitor, a GABA agonist, a TRPV1 modulator, an endothelin antagonist, a 5-$HT_{1A}$ antagonist, an $\alpha_1$ agonist, an opioid agonist, a $P_2X$ antagonist, a COX inhibitor, a $\sigma$ agonist, and a muscarinic agonist.

[11] An $EP_1$ receptor antagonist comprising the compound as set forth in any one of [1] to [8] or a pharmaceutically acceptable salt thereof.

[12] An agent for preventing or treating lower urinary tract symptoms, comprising the compound as set forth in any one of [1] to [8] or a pharmaceutically acceptable salt thereof.

[13] A method for preventing or treating lower urinary tract symptoms, comprising administering an effective amount of the compound as set forth in any one of [1] to [8] or a pharmaceutically acceptable salt thereof.

[14] Use of the compound as set forth in any one of [1] to [8] or a pharmaceutically acceptable salt thereof for the manufacture of a pharmaceutical composition for preventing or treating lower urinary tract symptoms.

DETAILED DESCRIPTION

The compound (I) of the present invention or a pharmaceutically acceptable salt thereof exhibits a potent $EP_1$ receptor antagonism, for example, in a test for confirmation of an $EP_1$ receptor antagonism. Therefore, the compound (I) of the present invention or a pharmaceutically acceptable salt thereof is useful as an agent for treating or preventing lower urinary tract symptoms (LUTS), in particular, overactive bladder syndrome (OABs) or the like, based on its $EP_1$ receptor antagonism.

The terms in the specification are defined as follows.

The "halogen atom" means a fluorine atom, a chlorine atom, a bromine atom, or an iodine atom. In X, a fluorine atom or a chlorine atom is preferable. In $R^3$, a fluorine atom or a chlorine atom is preferable, and a fluorine atom is more preferable. In $R^4$, a fluorine atom or a chlorine atom is preferable, and a chlorine atom is more preferable.

The "$C_{1-6}$ alkyl group" means an alkyl group having 1 to 6 carbon atoms, which may be branched. Examples thereof include a methyl group, an ethyl group, an n-propyl group, an isopropyl group, an n-butyl group, an isobutyl group, a sec-butyl group, a tert-butyl group, an n-pentyl group, an isopentyl group, a neopentyl group, a tert-pentyl group, a 1-methylbutyl group, a 2-methylbutyl group, a 1,2-dimethylpropyl group, an n-hexyl group, an isohexyl group, and the like. In $R^3$, a methyl group or an ethyl group is preferable, and a methyl group is more preferable.

The "branched $C_{3-6}$ alkyl group" means a branched alkyl group having 3 to 6 carbon atoms. Examples thereof include an isopropyl group, an isobutyl group, a sec-butyl group, a tert-butyl group, an isopentyl group, a neopentyl group, a tert-pentyl group, a 1-methylbutyl group, a 2-methylbutyl group, a 1,2-dimethylpropyl group, a 1-ethylpropyl group, an isohexyl group, and the like. It is preferably an isopropyl group, an isobutyl group, a sec-butyl group, or a 1-ethylpropyl group. It is more preferably an isopropyl group, a sec-butyl group, or a 1-ethylpropyl group. It is further preferably a sec-butyl group.

The "C$_{1-6}$ alkoxy group" means an alkoxy group having 1 to 6 carbon atoms, which may be branched. Examples thereof include a methoxy group, an ethoxy group, a propoxy group, an isopropoxy group, a butoxy group, an isobutoxy group, a sec-butoxy group, a tert-butoxy group, a pentyloxy group, a hexyloxy group, and the like. In R$^3$, a methoxy group or an ethoxy group is preferable, and a methoxy group is more preferable.

The "halo-C$_{1-6}$ alkyl group" means the C$_{1-6}$ alkyl group described above which is substituted with the same or different 1 to 5 or 6 halogen atoms described above. Examples thereof include a monofluoromethyl group, a difluoromethyl group, a trifluoromethyl group, a 2-chloroethyl group, a 2-fluoroethyl group, a 2,2-difluoroethyl group, a 1,1-difluoroethyl group, a 1,2-difluoroethyl group, a 2,2,2-trifluoroethyl group, a 1,1,2,2,2-pentafluoroethyl group, a 2,2,2-trichloroethyl group, a 3-fluoropropyl group, a 2-fluoropropyl group, a 1-fluoropropyl group, a 3,3-difluoropropyl group, a 2,2-difluoropropyl group, a 1,1-difluoropropyl group, a 1-fluorobutyl group, a 1-fluoropentyl group, a 1-fluorohexyl group, a 2,2,2-trifluoro-1-trifluoromethyl-1-ethyl group, and the like. It is preferably a monofluoromethyl group, a trifluoromethyl group, or a 2-fluoroethyl group.

The "halo-C$_{1-6}$ alkoxy" means the C$_{1-6}$ alkoxy group described above which is substituted with the same or different 1 to 5 halogen atoms described above. Examples thereof include a monofluoromethoxy group, a difluoromethoxy group, a trifluoromethoxy group, a 2-chloroethoxy group, a 2-fluoroethoxy group, a 2,2-difluoroethoxy group, a 1,1-difluoroethoxy group, a 1,2-difluoroethoxy group, a 2,2,2-trifluoroethoxy group, a 1,1,2,2,2-pentafluoroethoxy group, a 2,2,2-trichloroethoxy group, a 3-fluoropropoxy group, a 2-fluoropropoxy group, a 1-fluoropropoxy group, a 3,3-difluoropropoxy group, a 2,2-difluoropropoxy group, a 1,1-difluoropropoxy group, a 4-fluorobutoxy group, a 5-fluoropentyloxy group, a 6-fluorohexyloxy group, and the like. It is preferably a monofluoromethoxy group, a difluoromethoxy group, or a trifluoromethoxy group.

The "hydroxy-C$_{1-6}$ alkyl group" means the C$_{1-6}$ alkyl group described above which is substituted with a hydroxy group. Examples thereof include a hydroxymethyl group, a 1-hydroxyethyl group, a 1-hydroxy-1,1-dimethylmethyl group, a 2-hydroxyethyl group, a 2-hydroxy-2-methylpropyl group, a 3-hydroxypropyl group, and the like.

The "C$_{1-6}$ alkylsulfanyl group" means a group represented by (C$_{1-6}$ alkyl)-S—. Examples thereof include a methylsulfanyl group, an ethylsulfanyl group, a propylsulfanyl group, a butylsulfanyl group, a pentylsulfanyl group, a hexylsulfanyl group, and the like.

The "C$_{3-6}$cycloalkyl group" means a monocyclic saturated alicyclic hydrocarbon group having 3 to 6 carbon atoms. Examples thereof include a cyclopropyl group, a cyclobutyl group, a cyclopentyl group, a cyclohexyl group. In R$^2$, a cyclopropyl group or a cyclopentyl group is preferable. It is more preferably a cyclopropyl group.

The "C$_{7-10}$ aralkyl group" means an alkyl group having 1 to 4 carbon atoms, which is substituted with an aryl group such as a phenyl group, a naphthyl group, and the like. Examples thereof include a benzyl group, a phenethyl group, a 1-phenylethyl group, a 3-phenylpropyl group, a 4-phenylbutyl group, and the like.

The "5-membered aromatic heterocyclic group" means a 5-membered aromatic group containing 1 to 4 hetero atoms selected from an oxygen atom, a nitrogen atom, and a sulfur atom in the ring. Examples thereof include a furyl group, a pyrrolyl group, a thienyl group, an imidazolyl group, a pyrazolyl group, a 1,2,4-triazolyl group, an isothiazolyl group, an isoxazolyl group, an oxazolyl group, a thiazolyl group, a 1,3,4-oxadiazolyl group, a 1,2,4-oxadiazolyl group, and the like. It is preferably a 2-furyl group, a 3-furyl group, a 2-thienyl group, or a 3-thienyl group. It is more preferably a 3-furyl group or a 3-thienyl group.

The "6-membered aromatic heterocyclic group" means a 6-membered aromatic group containing 1 to 4 nitrogen atoms in the ring. Examples thereof include a pyridyl group, a pyrimidinyl group, a pyrazinyl group, a pyridazinyl group, and the like. It is preferably a pyridyl group, and more preferably a 3-pyridyl group.

The "acidic 5-membered hetero ring group" means a 5-membered ring containing a nitrogen atom bonded to an acidic proton in the ring or a 5-membered nitrogen-containing hetero ring having a phenolic hydroxy group. Examples thereof include the groups represented by the formulae:

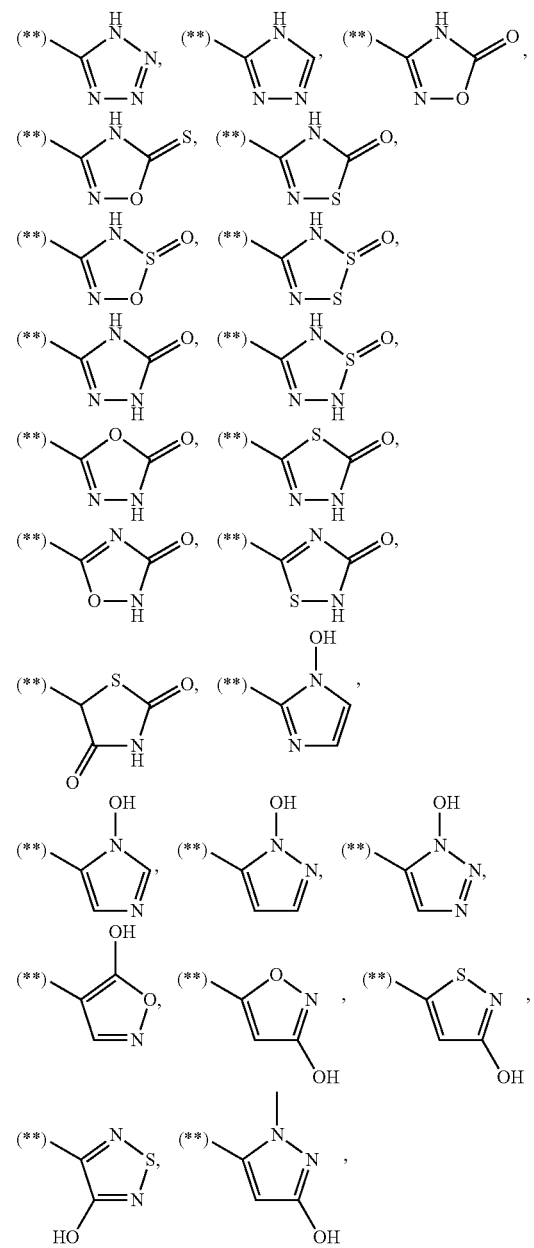

-continued

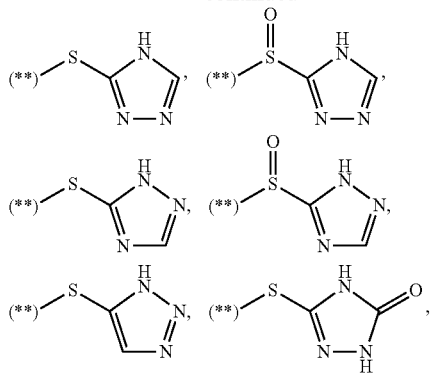

and the like. Preferably, the formulae are:

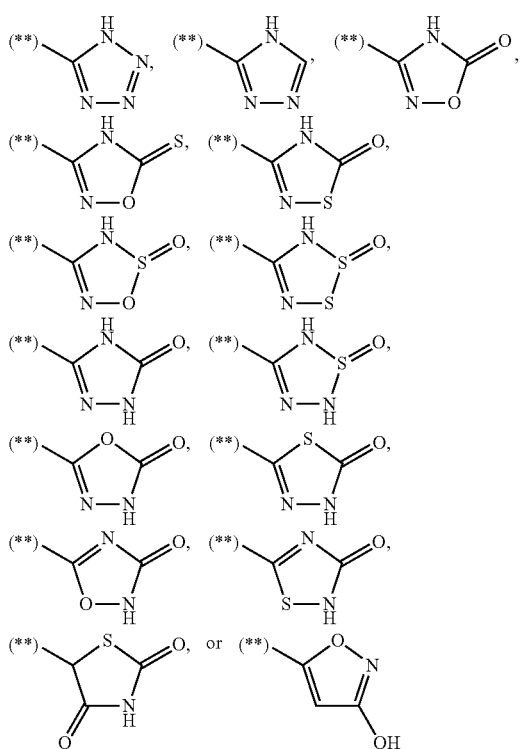

More preferably, the formulae are:

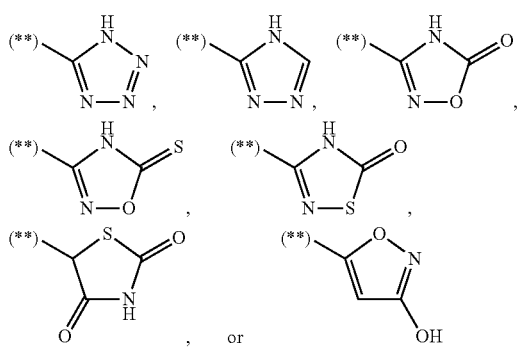

Further preferably, the formulae are:

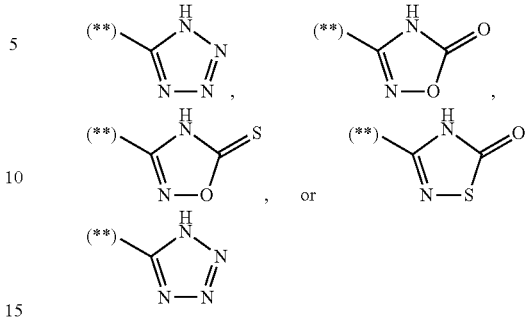

With the proviso that the bonds with (**) represent bonding to $Y^2$ of the compound represented by the general formula (I).

The "6-membered aromatic ring group substituted with a phenolic hydroxy group" means a 6-membered hetero ring group or an aromatic ring group which has a phenolic hydroxy group. Examples thereof include groups represented by the formulae:

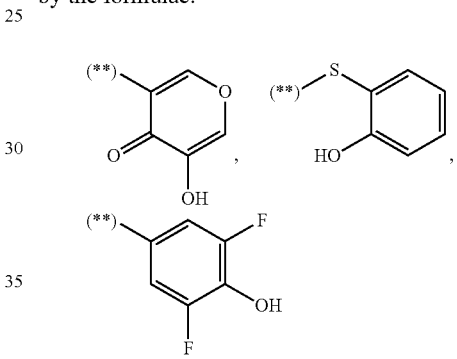

and the like.

With the proviso that the bonds with (**) represent bonding to $Y^2$ of the compound represented by the general formula (I).

The "$C_{1-6}$ alkylene group" means a divalent linear or branched-chained saturated hydrocarbon chain having 1 to 6 carbon atoms. Examples thereof include —$CH_2$—, —$CH_2CH_2$—, —$CH(CH_3)$—, —$(CH_2)_3$—, —$CH(CH_3)CH_2$—, —$CH_2CH(CH_3)$—, —$CH(CH_2CH_3)$—, —$C(CH_3)_2$—, —$(CH_2)_4$—, —$CH(CH_3)$—$(CH_2)_2$—, —$(CH_2)_2$—$CH(CH_3)$—, —$CH(CH_2CH_3)$—$CH_2$—, —$C(CH_3)_2CH_2$—, —$CH_2$—$C(CH_3)_2$—, —$CH(CH_3)$—$CH(CH_3)$—, —$(CH_2)_5$—, —$CH(CH_3)$—$(CH_2)_3$—, —$C(CH_3)_2CH_2CH_2$—, —$(CH_2)_6$—, —$C(CH_3)_2(CH_2)_3$—, and the like.

In addition, in the present specification, —$CH_2$— may be referred to as a methylene group.

The "oxy-$C_{1-6}$ alkylene group" means —O—$CH_2$—, —$CH_2$—O—, —O—$(CH_2)_2$—, —$CH_2$—O—$CH_2$—, —$(CH_2)_2$—O—, —O—$CH(CH_3)$—, —$CH(CH_3)$—O—, —O—$(CH_2)_3$—, —$(CH_2)_3$—O—, —O—$CH(CH_3)$—$CH_2$—, —$CH(CH_3)$—$CH_2$—O—, —O—$C(CH_3)_2$—, —$C(CH_3)_2$—O—, —O—$(CH_2)_4$—, —O—$(CH_2)_5$—, or —O—$(CH_2)_6$—. It is preferably —O—$CH_2$—, —$CH_2$—O—, —O—$(CH_2)_2$, —O—$CH(CH_3)$—, —O—$CH(CH_3)$—$CH_2$—, or —O—$C(CH_3)_2$—. It is more preferably —O—$CH_2$—, —O—$CH(CH_3)$—, or —O—$C(CH_3)_2$—.

Hereinafter, the present invention is described in more detail.

The compounds (I) of the present invention also include stereoisomers such as optical isomers, geometric isomers, and the like thereof.

In the case where the compound (I) of the present invention is an optical isomer having one or more asymmetric carbon atoms, the optical isomer of the compound (I) of the present invention may have either of an R configuration and an S configuration at the respective asymmetric carbon atoms. Also, any of the optical isomers thereof and a mixture of the optical isomers are encompassed by the present invention. Further, in the mixture of the optical active bodies, racemic bodies including equal amounts of the respective optical isomers are also encompassed within the scope of the present invention. In the case where the compound (I) of the present invention is a solid or crystal racemic body, the racemic compound, the racemic mixture, and the racemic solid solution are also encompassed within the scope of the present invention.

In the case where geometric isomers of the compound (I) of the present invention exist, the present invention includes any of the geometric isomers.

Furthermore, in the case where tautomers of the compound (I) of the present invention exist, the present invention includes any of the tautomers.

The compound (I) of the present invention can be converted to a pharmaceutically acceptable salt thereof according to a usual method, as necessary. Such a salt may be presented as an acid addition salt or a salt with a base.

Examples of the acid addition salt include acid addition salts with mineral acids such as hydrochloric acid, hydrobromic acid, hydroiodic acid, sulfuric acid, nitric acid, phosphoric acid and the like, and acid addition salts with organic acids such as formic acid, acetic acid, trifluoroacetic acid, methanesulfonic acid, benzene sulfonic acid, p-toluenesulfonic acid, propionic acid, citric acid, succinic acid, tartaric acid, fumaric acid, butyric acid, oxalic acid, malonic acid, maleic acid, lactic acid, malic acid, carbonic acid, glutamic acid, aspartic acid and the like.

Examples of the salt with a base include salts with inorganic bases, such as a sodium salt, a potassium salt, a calcium salt, a magnesium salt, and the like, and salts with organic bases such as piperidine, morpholine, pyrrolidine, arginine, lysine, and the like.

In addition, the compound (I) of the present invention or a pharmaceutically acceptable salt thereof also encompasses hydrates, and solvates with pharmaceutically acceptable solvents such as ethanol and the like.

The "$EP_1$ receptor antagonism" as mentioned in the present invention means an action of inhibiting the binding of a prostaglandin $E_2$ ($PGE_2$) to a prostaglandin E receptor 1 ($EP_1$ receptor).

The $EP_1$ receptor antagonism reduces or inhibits the influx amount of calcium into cells and thus decreases the intracellular calcium concentration. As a result, the $EP_1$ receptor antagonism exhibits an action of relaxation of smooth muscles, inhibition of sensory nerve stimulation, or the like. Particularly, the $EP_1$ receptor antagonist acts on the bladder, the urothelium, or the like, whereby it is useful as an agent for treating or preventing LUTS, in particular, the symptoms of OABs or the like.

Furthermore, the $EP_1$ receptor antagonism can be evaluated based on the efficacy of inhibiting the influx amount of calcium into cells by a $PGE_2$. This efficacy can be evaluated by an in vitro test or in vivo test mutatis mutandis in accordance with "Pharmacological Test Examples" described in JP2008-214224A.

Preferable substituents for the compound (I) of the present invention or a pharmaceutically acceptable salt thereof are as follows.

(I-1) A is preferably a benzene ring, a pyridine ring, or a furan ring, more preferably a furan ring or a pyridine ring, and further preferably a pyridine ring.

(I-2) $Y^1$ is preferably a methylene group, —CH(CH$_3$)—, or —C(CH$_3$)$_2$—, and more preferably a methylene group.

(I-3) $Y^2$ is preferably a single bond.

(I-4) $R^1$ is preferably —C(=O)—NH—SO$_2$—$R^6$ or an acidic 5-membered hetero ring group, and more preferably —C(=O)—NH—SO$_2$—$R^6$ or the following formulae:

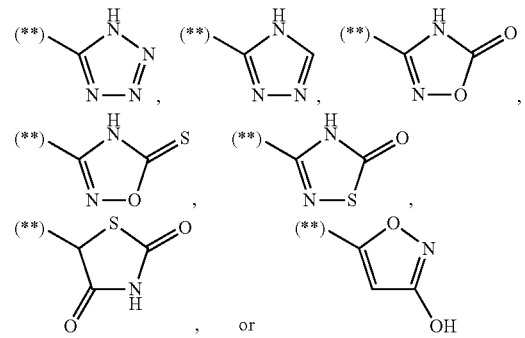

further preferably —C(=O)—NH—SO$_2$—$R^6$ or the following formulae:

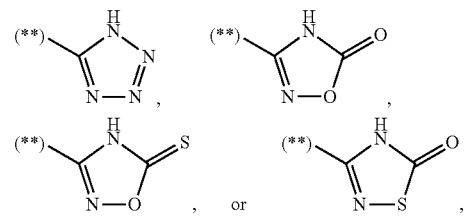

and most preferably —C(=O)—NH—SO$_2$—$R^6$ or the following formula:

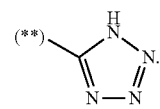

(I-5) $R^2$ is preferably a group selected from the group consisting of the following o), q1), r2), and t2):

o) a branched C$_{3-6}$ alkyl group, q1) a C$_{3-6}$ cycloalkyl group, in which the ring is unsubstituted or substituted with one C$_{1-6}$ alkyl group at the 1-position, r2) a phenyl group, in which the ring is unsubstituted or substituted with one to two groups independently selected from the group consisting of the following: a halogen atom, a C$_{1-6}$ alkyl group, or a C$_{1-6}$ alkoxy group, or t2) a 5-membered aromatic heterocyclic group, in which the ring is unsubstituted or substituted with one C$_{1-6}$ alkyl group, more preferably an isopropyl group, a sec-butyl group, a $C_{3-6}$ cycloalkyl group in which the ring is unsubstituted or substituted with one $C_{1-6}$ alkyl group at the 1-position, a phenyl group which is unsubstituted or substituted with one fluorine atom, a 3-furyl group which is unsubstituted or substituted with one $C_{1-6}$ alkyl group, or a 3-thienyl group which is unsubstituted or substituted with one $C_{1-6}$ alkyl group, further preferably a 1-methylcyclopropyl group, a phenyl group, a 2-fluorophenyl group, a 3-fluorophenyl group, a 4-fluorophenyl group, a 3-furyl group, or a 3-thienyl group, and further more preferably a 1-methylcyclopropyl group, a phenyl group, a 2-fluorophenyl group, a 3-furyl group, or a 3-thienyl group.

(I-6) $R^3$ is preferably a halogen atom, a $C_{1-6}$ alkyl group, a halo-$C_{1-6}$ alkyl group, a $C_{1-6}$ alkoxy group, or a $C_{3-6}$ cycloalkyl group, more preferably a fluorine atom, a chlorine atom, a methyl group, a trifluoromethyl group, a methoxy group, an ethoxy group, or a cyclopropyl group, further more preferably a fluorine atom, a chlorine atom, a methyl group, a methoxy group, or an ethoxy group, further more preferably a methyl group or a methoxy group, and most preferably a methoxy group.

(I-7) $R^4$ is preferably a hydrogen atom, a halogen atom, or a $C_{1-6}$ alkyl group, more preferably a hydrogen atom, a fluorine atom, a chlorine atom, or a methyl group, and further more preferably a hydrogen atom or a chlorine atom.

(I-8) $R^5$ is preferably a hydrogen atom.

(I-9) $R^6$ is preferably a $C_{1-6}$ alkyl group, a $C_{3-6}$ cycloalkyl group, or a phenyl group in which the ring is unsubstituted or substituted with one group selected from the group consisting of the following: a halogen atom, a $C_{1-6}$ alkyl group, and a $C_{1-6}$ alkoxy group, more preferably a $C_{1-6}$ alkyl group, a cyclopropyl group, or a phenyl group, further more preferably a methyl group, an ethyl group, an n-propyl group, an isopropyl group, a cyclopropyl group, or a phenyl group, and further more preferably a methyl group, an ethyl group, an n-propyl group, an isopropyl group, or a cyclopropyl group.

In a preferable embodiment, the compound (I) of the present invention or a pharmaceutically acceptable salt thereof is a compound including a combination of preferable substituents described in (1-1) to (1-9).

Embodiment 1

In a preferable embodiment of the present invention,
A is a benzene ring, a pyridine ring, or a furan ring;
$Y^1$ is a methylene group;
$Y^2$ is a single bond;
$R^1$ is —C(=O)—NH—SO$_2$—$R^6$ or an acidic 5-membered hetero ring group;
$R^2$ is selected from the following o), q1), r2), and t2):
  o) a branched $C_{3-6}$ alkyl group,
  q1) a $C_{3-6}$ cycloalkyl group, in which the ring is unsubstituted or substituted with one $C_{1-6}$ alkyl group at the 1-position,
  r2) a phenyl group, in which the ring is unsubstituted or substituted with one to two groups independently selected from the group consisting of the following: a halogen atom, a $C_{1-6}$ alkyl group, or a $C_{1-6}$ alkoxy group, or
  t2) a 5-membered aromatic heterocyclic group, in which the ring is unsubstituted or substituted with one $C_{1-6}$ alkyl group;
$R^3$ is a halogen atom, a $C_{1-6}$ alkyl group, a halo-$C_{1-6}$ alkyl group, a $C_{1-6}$ alkoxy group, or a $C_{3-6}$ cycloalkyl group;

$R^4$ is a hydrogen atom, a halogen atom, or a $C_{1-6}$ alkyl group;
$R^5$ is a hydrogen atom; and
$R^6$ is a $C_{1-6}$ alkyl group, a $C_{3-6}$ cycloalkyl group, or a phenyl group in which the ring is unsubstituted or substituted with one group selected from the group consisting of the following: a halogen atom, a $C_{1-6}$ alkyl group, and a $C_{1-6}$ alkoxy group.

Embodiment 2

In an embodiment that is preferable to Embodiment 1,
$R^3$ is a $C_{1-6}$ alkoxy group, and more preferably a methoxy group; and
$R^6$ is a $C_{1-6}$ alkyl group or a $C_{3-6}$ cycloalkyl group.

Examples of the concrete compounds included in the present embodiment include the following compounds:
N-(methanesulfonyl)-6-(5-methoxy-2-phenylindol-1-ylmethyl)pyridine-2-carboxamide (Example 1-1),
6-[6-fluoro-5-methoxy-2-(thiophen-3-yl)indol-1-ylmethyl]-N-(methanesulfonyl)pyridine-2-carboxamide (Example 1-5),
6-(6-chloro-5-methoxy-2-phenylindol-1-ylmethyl)-N-(ethanesulfonyl)pyridine-2-carboxamide (Example 1-6),
N-(ethanesulfonyl)-6-(5-methoxy-2-phenylindol-1-ylmethyl)pyridine-2-carboxamide (Example 1-12),
5-methoxy-2-phenyl-1-[6-(1H-1,2,3,4-tetrazol-5-yl)pyridin-2-ylmethyl]-1H-indole (Example 2-1),
5-methoxy-2-phenyl-1-[5-(1H-1,2,3,4-tetrazol-5-yl)furan-2-ylmethyl]-1H-indole (Example 2-2),
6-chloro-5-methoxy-2-phenyl-1-[6-(1H-1,2,3,4-tetrazol-5-yl)pyridin-2-ylmethyl]-1H-indole (Example 2-3),
6-fluoro-5-methoxy-1-[6-(1H-1,2,3,4-tetrazol-5-yl)pyridin-2-ylmethyl]-2-(thiophen-3-yl)-1H-indole (Example 2-4),
6-[2-(butan-2-yl)-6-chloro-5-methoxyindol-1-ylmethyl]-N-(ethanesulfonyl)pyridine-2-carboxamide (Example 4-2),
6-[2-(2,5-difluorophenyl)-5-methoxyindol-1-ylmethyl]-N-(ethanesulfonyl)pyridine-2-carboxamide (Example 4-5),
6-[2-(butan-2-yl)-5-methoxyindol-1-ylmethyl]-N-(ethanesulfonyl)pyridine-2-carboxamide (Example 4-10),
6-(5-methoxy-2-phenylindol-1-ylmethyl)-N-(propane-1-sulfonyl)pyridine-2-carboxamide (Example 4-12),
6-(5-methoxy-2-phenylindol-1-ylmethyl)-N-(propane-2-sulfonyl)pyridine-2-carboxamide (Example 4-13),
N-(cyclopropanesulfonyl)-6-(5-methoxy-2-phenylindol-1-ylmethyl)pyridine-2-carboxamide (Example 4-14),
6-[2-(butan-2-yl)-5-methoxyindol-1-ylmethyl]-N-(propane-1-sulfonyl)pyridine-2-carboxamide (Example 4-16),
6-[2-(butan-2-yl)-5-methoxyindol-1-ylmethyl]-N-(propane-2-sulfonyl)pyridine-2-carboxamide (Example 4-17),
6-[2-(butan-2-yl)-5-methoxyindol-1-ylmethyl]-N-(cyclopropanesulfonyl)pyridine-2-carboxamide (Example 4-18),
6-(6-fluoro-5-methoxy-2-phenylindol-1-ylmethyl)-N-(methanesulfonyl)pyridine-2-carboxamide (Example 4-19),
N-(ethanesulfonyl)-6-(6-fluoro-5-methoxy-2-phenylindol-1-ylmethyl)pyridine-2-carboxamide (Example 4-20),
6-(6-fluoro-5-methoxy-2-phenylindol-1-ylmethyl)-N-(propane-1-sulfonyl)pyridine-2-carboxamide (Example 4-22),
N-(cyclopropanesulfonyl)-6-(6-fluoro-5-methoxy-2-phenylindol-1-ylmethyl)pyridine-2-carboxamide (Example 4-23), 2-(butan-2-yl)-5-methoxy-1-[6-(1H-1,2,3,4-tetrazol-5-yl)pyridin-2-ylmethyl]-1H-indole (Example 5-1),
6-fluoro-5-methoxy-2-phenyl-1-[6-(1H-1,2,3,4-tetrazol-5-yl)pyridin-2-ylmethyl]-1H-indole (Example 5-3),
6-chloro-2-(furan-3-yl)-5-methoxy-1-[6-(1H-1,2,3,4-tetrazol-5-yl)pyridin-2-ylmethyl]-1H-indole (Example 5-4),
5-methoxy-2-(1-methylcyclopropyl)-1-[6-(1H-1,2,3,4-tetrazol-5-yl)pyridin-2-ylmethyl]-1H-indole (Example 5-5),
6-chloro-5-methoxy-2-(1-methylcyclopropyl)-1-[6-(1H-1,2,3,4-tetrazol-5-yl)pyridin-2-ylmethyl]-1H-indole (Example 5-6),
5-methoxy-2-(1-methylcyclopropyl)-1-[5-(1H-1,2,3,4-tetrazol-5-yl)furan-2-ylmethyl]-1H-indole (Example 5-7), and
3-[6-(6-fluoro-5-methoxy-2-phenylindol-1-ylmethyl)pyridin-2-yl]-4,5-dihydro-1,2,4-oxadiazol-5-one (Example 6-6).

Embodiment 3
In an embodiment that is preferable to Embodiment 2,
$R^1$ is —C(=O)—NH—SO$_2$—$R^6$ or an acidic 5-membered hetero ring group, and more preferably —C(=O)—NH—SO$_2$—$R^6$ or the following formulae:

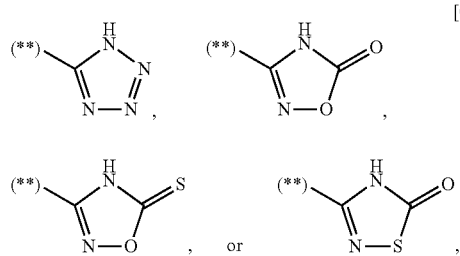

[Chem. 17]

and further preferably —C(=O)—NH—SO$_2$—$R^6$; and
$R^6$ is a methyl group, an ethyl group, an n-propyl group, an isopropyl group, or a cyclopropyl group.

Embodiment 4
In an embodiment that is preferable to Embodiment 3,
A is a pyridine ring.
Examples of the concrete compounds included in the present embodiment include the following compounds:
N-(methanesulfonyl)-6-(5-methoxy-2-phenylindol-1-ylmethyl)pyridine-2-carboxamide (Example 1-1),
6-[6-fluoro-5-methoxy-2-(thiophen-3-yl)indol-1-ylmethyl]-N-(methanesulfonyl)pyridine-2-carboxamide (Example 1-5),
6-(6-chloro-5-methoxy-2-phenylindol-1-ylmethyl)-N-(ethanesulfonyl)pyridine-2-carboxamide (Example 1-6),
N-(ethanesulfonyl)-6-(5-methoxy-2-phenylindol-1-ylmethyl)pyridine-2-carboxamide (Example 1-12),
5-methoxy-2-phenyl-1-[6-(1H-1,2,3,4-tetrazol-5-yl)pyridin-2-ylmethyl]-1H-indole (Example 2-1),
6-chloro-5-methoxy-2-phenyl-1-[6-(1H-1,2,3,4-tetrazol-5-yl)pyridin-2-ylmethyl]-1H-indole (Example 2-3),
6-fluoro-5-methoxy-1-[6-(1H-1,2,3,4-tetrazol-5-yl)pyridin-2-ylmethyl]-2-(thiophen-3-yl)-1H-indole (Example 2-4),
6-[2-(butan-2-yl)-6-chloro-5-methoxyindol-1-ylmethyl]-N-(ethanesulfonyl)pyridine-2-carboxamide (Example 4-2),
6-[2-(2,5-difluorophenyl)-5-methoxyindol-1-ylmethyl]-N-(ethanesulfonyl)pyridine-2-carboxamide (Example 4-5),
6-[2-(butan-2-yl)-5-methoxyindol-1-ylmethyl]-N-(ethanesulfonyl)pyridine-2-carboxamide (Example 4-10),
6-(5-methoxy-2-phenylindol-1-ylmethyl)-N-(propane-1-sulfonyl)pyridine-2-carboxamide (Example 4-12),
6-(5-methoxy-2-phenylindol-1-ylmethyl)-N-(propane-2-sulfonyl)pyridine-2-carboxamide (Example 4-13),
N-(cyclopropanesulfonyl)-6-(5-methoxy-2-phenylindol-1-ylmethyl)pyridine-2-carboxamide (Example 4-14),
6-[2-(butan-2-yl)-5-methoxyindol-1-ylmethyl]-N-(propane-1-sulfonyl)pyridine-2-carboxamide (Example 4-16),
6-[2-(butan-2-yl)-5-methoxyindol-1-ylmethyl]-N-(propane-2-sulfonyl)pyridine-2-carboxamide (Example 4-17),
6-[2-(butan-2-yl)-5-methoxyindol-1-ylmethyl]-N-(cyclopropanesulfonyl)pyridine-2-carboxamide (Example 4-18),
6-(6-fluoro-5-methoxy-2-phenylindol-1-ylmethyl)-N-(methanesulfonyl)pyridine-2-carboxamide (Example 4-19),
N-(ethanesulfonyl)-6-(6-fluoro-5-methoxy-2-phenylindol-1-ylmethyl)pyridine-2-carboxamide (Example 4-20),
6-(6-fluoro-5-methoxy-2-phenylindol-1-ylmethyl)-N-(propane-1-sulfonyl)pyridine-2-carboxamide (Example 4-22),
N-(cyclopropanesulfonyl)-6-(6-fluoro-5-methoxy-2-phenylindol-1-ylmethyl)pyridine-2-carboxamide (Example 4-23),
2-(butan-2-yl)-5-methoxy-1-[6-(1H-1,2,3,4-tetrazol-5-yl)pyridin-2-ylmethyl]-1H-indole (Example 5-1),
6-fluoro-5-methoxy-2-phenyl-1-[6-(1H-1,2,3,4-tetrazol-5-yl)pyridin-2-ylmethyl]-1H-indole (Example 5-3),
6-chloro-2-(furan-3-yl)-5-methoxy-1-[6-(1H-1,2,3,4-tetrazol-5-yl)pyridin-2-ylmethyl]-1H-indole (Example 5-4),
5-methoxy-2-(1-methylcyclopropyl)-1-[6-(1H-1,2,3,4-tetrazol-5-yl)pyridin-2-ylmethyl]-1H-indole (Example 5-5),
6-chloro-5-methoxy-2-(1-methylcyclopropyl)-1-[6-(1H-1,2,3,4-tetrazol-5-yl)pyridin-2-ylmethyl]-1H-indole (Example 5-6), and
3-[6-(6-fluoro-5-methoxy-2-phenylindol-1-ylmethyl)pyridin-2-yl]-4,5-dihydro-1,2,4-oxadiazol-5-one (Example 6-6).

Embodiment 5
In an embodiment that is preferable to Embodiment 3,
A is a furan ring.
Examples of the concrete compounds included in the present embodiment include the following compounds:
5-methoxy-2-phenyl-1-[5-(1H-1,2,3,4-tetrazol-5-yl)furan-2-ylmethyl]-1H-indole (Example 2-2), and
5-methoxy-2-(1-methylcyclopropyl)-1-[5-(1H-1,2,3,4-tetrazol-5-yl)furan-2-ylmethyl]-1H-indole (Example 5-7).

Embodiment 6
In an embodiment that is preferable to Embodiment 3,
A is a benzene ring.

Production Process of Compound (I) of the Present Invention

The compound (I) of the present invention or a pharmaceutically acceptable salt thereof can be prepared according to the method described below in detail or a similar method thereto, or according to a method described in other literature or a similar method thereto.

The compound (I) of the present invention or a pharmaceutically acceptable salt thereof can be prepared using a compound (I). The compound (I) may be commercially available or can be prepared according to the method described below in detail or a similar method thereto, or according to a method described in other literature or a similar method thereto.

[A] Synthesis of Compound (I)
The compound (I) can be prepared with the method shown in Scheme 1. If a protective group is necessary, combinations of introduction and cleavage can be appropriately carried out in accordance with usual methods.

Scheme 1

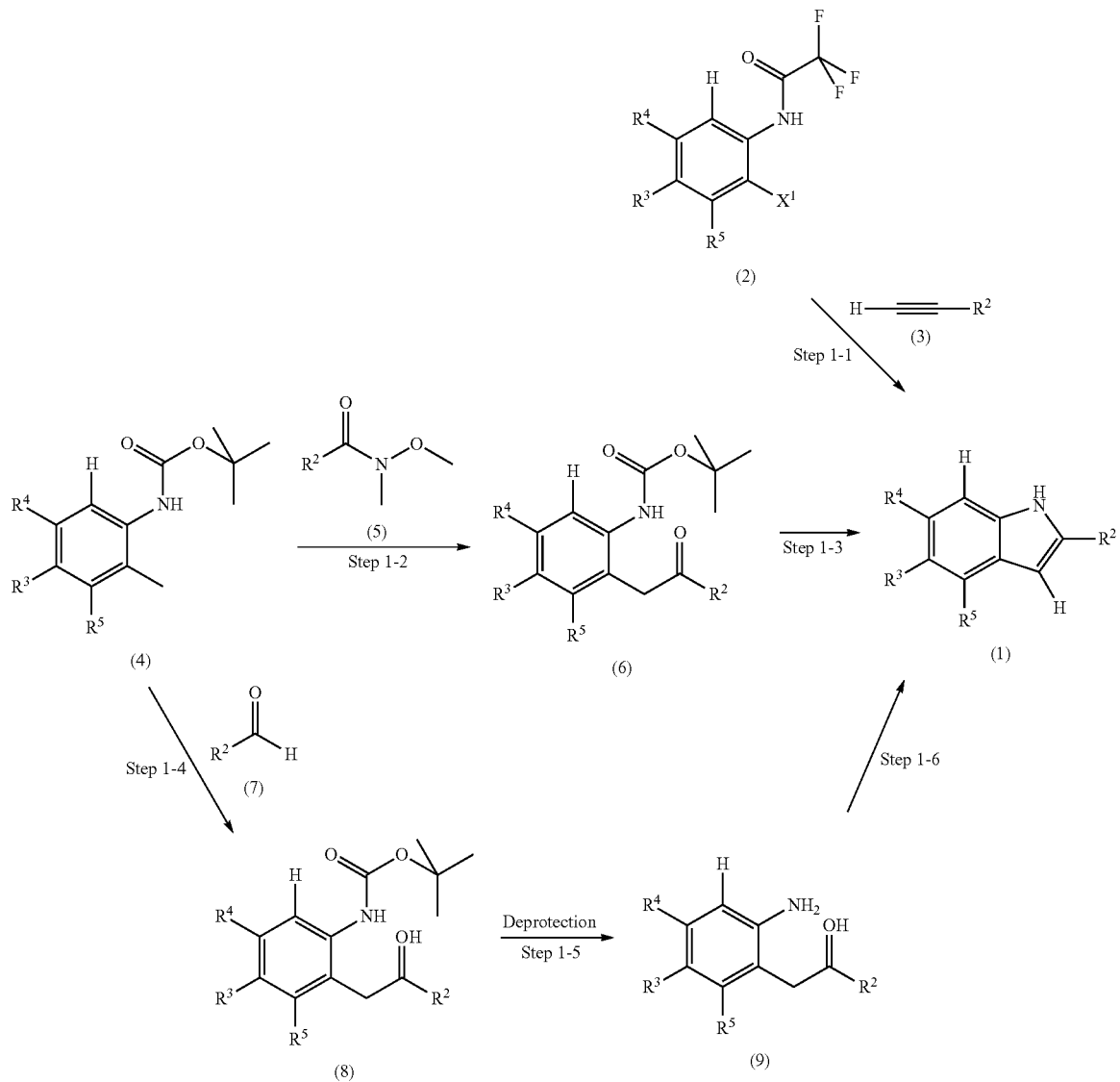

(wherein $R^2$, $R^3$, $R^4$, and $R^5$ have the same meanings as defined above; $X^1$ represents a leaving group such as a chlorine atom, a bromine atom, an iodine atom, a trifluoromethanesulfonyloxy group, and the like.)

Step 1-1

The compound (1) can be prepared by reacting a compound (2) with a compound (3) in the presence of a palladium catalyst, a copper catalyst, and a base in a solvent. Examples of the solvent to be used include acetonitrile, N,N-dimethylformamide, tetrahydrofuran, a mixed solvent thereof, and the like. Examples of the palladium catalyst to be used include bis(triphenylphosphine) palladium(II) dichloride, tetrakis(triphenylphosphine) palladium(0), and the like. Examples of the copper catalyst to be used include copper(I) iodide. Examples of the base to be used include triethylamine, N,N-diisopropylethylamine, potassium carbonate, potassium phosphate, and the like. The reaction temperature is usually room temperature to solvent reflux temperature. The reaction time varies depending on a starting material to be used, a solvent to be used, a reaction temperature, or the like, but it is usually 30 minutes to 3 days.

Further, the compounds (2) and (3) used in the present step may be commercially available or can be prepared according to a method described in other literature or a similar method thereto.

Step 1-2

A compound (6) can be prepared by reacting a compound (4) that has been lithiated using alkyllithium, with a compound (5) in a solvent. Examples of the solvent to be used include tetrahydrofuran, diethyl ether, 1,2-dimethoxyethane, 1,4-dioxane, a mixed solvent thereof, and the like. Examples of the alkyllithium to be used include n-butyllithium, sec-butyllithium, tert-butyllithium, and the like, and sec-butyllithium is preferable. The reaction temperature is usually −78° C. to solvent reflux temperature. The reaction time varies depending on a starting material to be used, a solvent to be used, a reaction temperature, or the like, but it is usually 30 minutes to 1 day.

Further, the compounds (4) and (5) used in the present step may be commercially available or can be prepared according to a method described in other literature or a similar method thereto.

Step 1-3

The compound (1) can be prepared by treating the compound (6) with an acid in a solvent. Examples of the solvent to be used include dichloromethane, chloroform, methanol, ethanol, tetrahydrofuran, 1,4-dioxane, a mixed solvent thereof, and the like. Examples of the acid to be used include trifluoroacetic acid, methanesulfonic acid, concentrated hydrochloric acid, concentrated sulfuric acid, and the like. The reaction temperature is usually −78° C. to solvent reflux temperature. The reaction time varies depending on a starting material to be used, a solvent to be used, a reaction temperature, or the like, but it is usually 30 minutes to 3 days.

Step 1-4

A compound (8) can be prepared by reacting a compound (4) that has been lithiated using alkyllithium, with a compound (7) in a solvent. Examples of the solvent to be used include tetrahydrofuran, diethyl ether, 1,2-dimethoxyethane, 1,4-dioxane, a mixed solvent thereof, and the like. Examples of the alkyllithium to be used include n-butyllithium, sec-butyllithium, tert-butyllithium, and the like, and sec-butyllithium is preferable. The reaction temperature is usually −78° C. to solvent reflux temperature. The reaction time varies depending on a starting material to be used, a solvent to be used, a reaction temperature, or the like, but it is usually 30 minutes to 1 day.

Step 1-5

A compound (9) can be prepared by treating the compound (8) under acidic conditions. Such a reaction is well-known to a skilled person in the art, and can be carried out according to the method described in, for example, "Greene's Protective Groups in Organic Synthesis", fourth edition, Wiley-Interscience, 2006, edited by Greene & Wuts.

Step 1-6

The compound (1) can be prepared by oxidizing the compound (9) in the presence of a palladium catalyst, an oxidizing agent, and a base in a solvent. Examples of the solvent to be used include N,N-dimethylformamide, 1-methyl-2-pyrrolidone, a mixed solvent thereof, and the like. Examples of the palladium catalyst to be used include tetrakis(triphenylphosphine) palladium(0). Examples of the oxidizing agent to be used include mesityl bromide. Examples of the base to be used include potassium carbonate, cesium carbonate, sodium hydride, and the like. The reaction temperature is usually room temperature to solvent reflux temperature. The reaction time varies depending on a starting material to be used, a solvent to be used, a reaction temperature, or the like, but it is usually 30 minutes to 3 days.

[B] Synthesis of Compounds (1a) to (1k)

The compound (I) of the present invention can be prepared as compounds (Ia) to (Ik) with the methods shown in Schemes 2 to 9. If a protective group is necessary, combinations of introduction and cleavage can be appropriately carried out in accordance with usual methods.

Among the compounds (I) of the present invention, a compound (Ia) in which $R^1$ is —C(=O)—NH—SO$_2$—$R^6$ can be prepared by the method shown in Scheme 2 or a similar method thereto, or according to a method described in other literature or a similar method thereto. If a protective group is necessary, combinations of introduction and cleavage can be appropriately carried out in accordance with usual methods.

Scheme 2

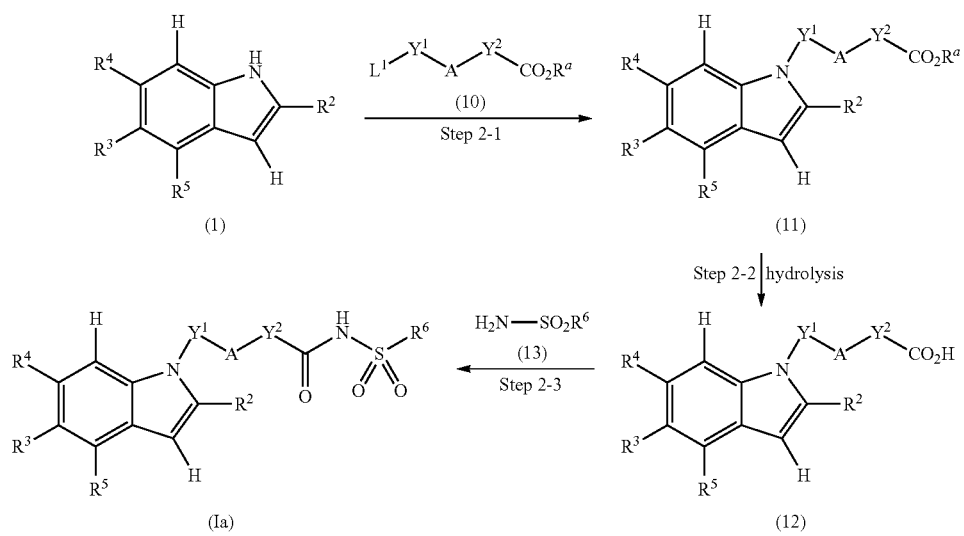

(wherein A, $R^2$, $R^3$, $R^4$, $R^5$, $R^6$, $Y^1$, and $Y^2$ have the same meanings as defined above; $R^a$ represents a $C_{1-6}$ alkyl group or a $C_{7-10}$ aralkyl group; and $L^1$ represents a leaving group such as a chlorine atom, a bromine atom, an iodine atom, a methanesulfonyloxy group, and the like.)

Step 2-1

A compound (11) can be prepared by reacting the compound (1) with a compound (10) in the presence of a base in a solvent. Examples of the solvent to be used include N,N-dimethylformamide, N,N-dimethylacetamide, N,N-dimethylimidazolidinone, tetrahydrofuran, a mixed solvent thereof, and the like. Examples of the base to be used include sodium hydride, cesium carbonate, potassium tert-butoxide, lithium bis(trimethylsilyl)amide, and the like. The reaction temperature is usually −20° C. to solvent reflux temperature. The reaction time varies depending on a starting material to be used, a solvent to be used, a reaction temperature, or the like, but it is usually 30 minutes to 3 days. The present step can be carried out upon addition of sodium iodide, tetra-n-butylammonium bromide, tetra-n-butylammonium iodide, and the like, as necessary.

Further, the compound (10) used in the present step may be commercially available or can be prepared according to a method described in literature or a similar method thereto by using a corresponding alcohol as a starting material and converting a hydroxy group of the alcohol to a chlorine atom, a bromine atom, an iodine atom, a methanesulfonyloxy group, and the like.

Step 2-2

A compound (12) can be prepared by treating the compound (11) according to a method for converting an ester group into a carboxy group. Such a method is well-known to a skilled person in the art, and can be carried out according to the method described in, for example, 'Greene's Protective Groups in Organic Synthesis', fourth edition, Wiley-Interscience, 2006, edited by Greene & Wuts.

Step 2-3

The compound (Ia) of the present invention can be prepared by reacting the compound (12) with a compound (13) in the presence of a condensing agent in a solvent. Examples of the solvent to be used include dichloromethane, N,N-dimethylformamide, tetrahydrofuran, acetonitrile, a mixed solvent thereof, and the like. Examples of the condensing agent to be used include 1-ethyl-3-(3-dimethylaminopropyl)carbodiimide hydrochloride (EDC), N,N'-dicyclohexylcarbodiimide (DCC), and the like. The present step is preferably carried out upon addition of a tertiary amine, as necessary. Examples of the tertiary amine to be used include 4-dimethylaminopyridine, triethylamine, N,N-diisopropylethylamine, and the like. The reaction temperature is usually 0° C. to solvent reflux temperature. The reaction time varies depending on a starting material to be used, a solvent to be used, a reaction temperature, or the like, but it is usually 30 minutes to 3 days.

Further, the compound (13) used in the present step may be commercially available or can be prepared according to a method described in other literature or a similar method thereto.

Among the compounds (I) of the present invention, a compound (Ib) in which $R^1$ is a tetrazolyl group can be prepared by the method shown in Scheme 3 or a similar method thereto, or according to a method described in other literature or a similar method thereto. If a protective group is necessary, combinations of introduction and cleavage can be appropriately carried out in accordance with usual methods.

Scheme 3

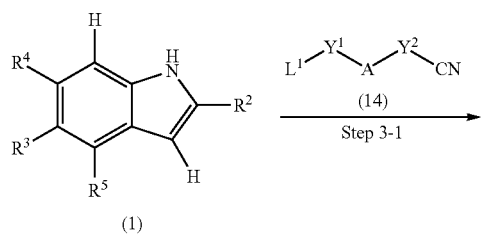

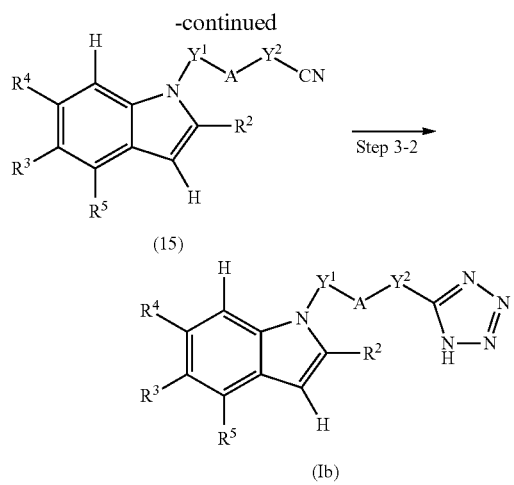

(wherein A, $R^2$, $R^3$, $R^4$, $R^5$, $Y^1$, and $Y^2$ have the same meanings as defined above; and $L^2$ represents a leaving group such as a chlorine atom, a bromine atom, an iodine atom, a methanesulfonyloxy group, and the like.)

Step 3-1

A compound (15) can be prepared by reacting the compound (1) with a compound (14) in the presence of a base in a solvent. Examples of the solvent to be used include N,N-dimethylformamide, N,N-dimethylacetamide, tetrahydrofuran, a mixed solvent thereof, and the like. Examples of the base to be used include sodium hydride, cesium carbonate, potassium tert-butoxide, lithium bis(trimethylsilyl)amide, and the like. The reaction temperature is usually −20° C. to solvent reflux temperature. The reaction time varies depending on a starting material to be used, a solvent to be used, a reaction temperature, or the like, but it is usually 30 minutes to 3 days. The present step can be carried out upon addition of sodium iodide, tetra-n-butylammonium bromide, tetra-n-butylammonium iodide, and the like, as necessary.

Further, the compound (14) used in the present step may be commercially available or can be prepared according to a method described in other literature or a similar method thereto.

Step 3-2

The compound (Ib) of the present invention can be prepared by reacting the compound (15) with an azide salt in a solvent. Examples of the solvent to be used include methanol, isopropyl alcohol, water, N,N-dimethylformamide, toluene, xylene, a mixed solvent thereof, and the like. Examples of the azide salt to be used include sodium azide, potassium azide, cesium azide, and the like. The present step is preferably carried out upon addition of ammonium chloride, triethylamine hydrochloride, zinc bromide, zinc chloride, and the like, as necessary. The reaction temperature is usually room temperature to solvent reflux temperature. The reaction time varies depending on a starting material to be used, a solvent to be used, a reaction temperature, or the like, but it is usually 30 minutes to 3 days.

Among the compounds (I) of the present invention, compounds (Ic) to (If) in which $R^1$ is the formulae:

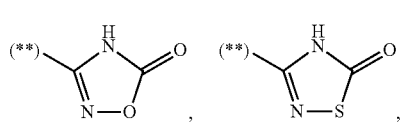

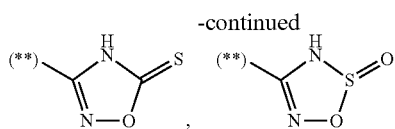

can be prepared by the method shown in Scheme 4 or a similar method thereto, or according to a method described in other literature or a similar method thereto. If a protective group is necessary, combinations of introduction and cleavage can be appropriately carried out in accordance with usual methods.

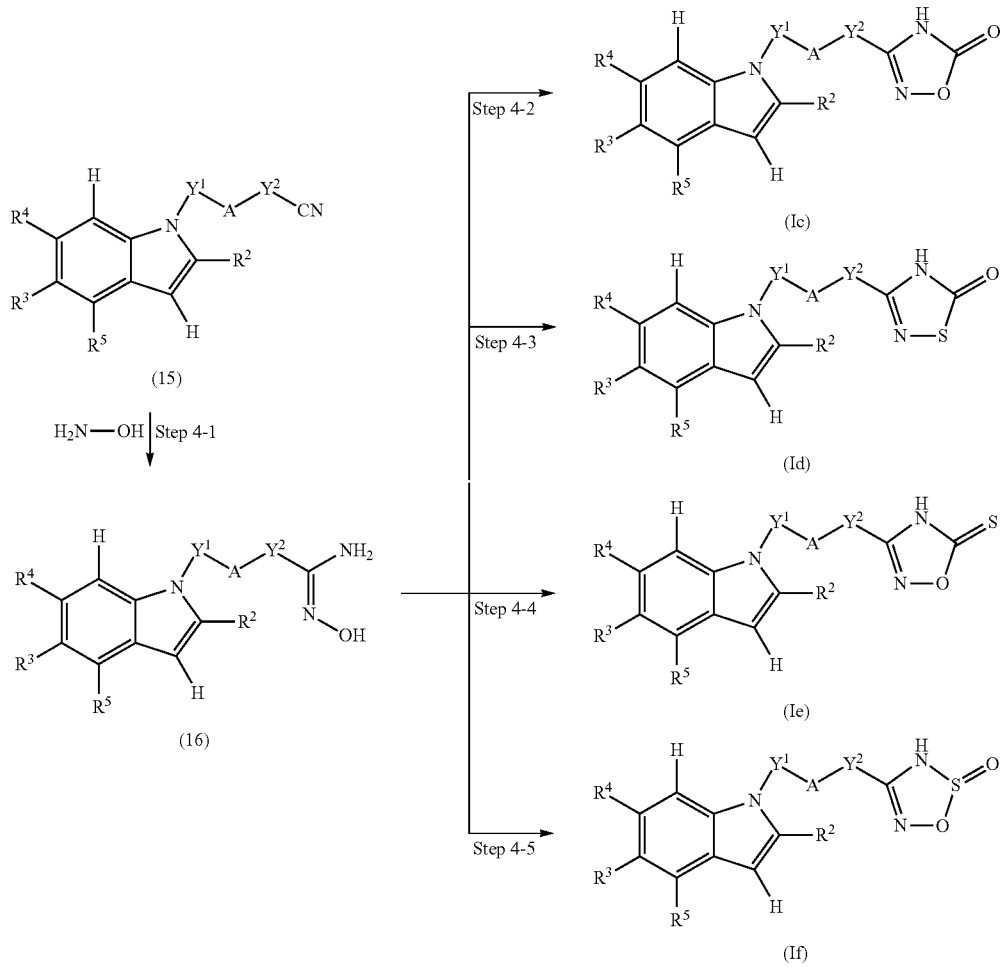

(wherein A, $R^2$, $R^3$, $R^4$, $R^5$, $Y^1$, and $Y^2$ have the same meanings as defined above.)

The compound (15) can be prepared by the method shown in Scheme 3 or a similar method thereto, or according to a method described in other literature or a similar method thereto.

Step 4-1

A compound (16) can be prepared by reacting the compound (15) with hydroxylamine in a solvent. Examples of the solvent to be used include dimethylsulfoxide, water, methanol, tetrahydrofuran, toluene, dichloromethane, a mixed solvent thereof, and the like. The reaction temperature is usually room temperature to solvent reflux temperature. The reaction time varies depending on a starting material to be used, a solvent to be used, a reaction temperature, or the like, but it is usually 30 minutes to 3 days.

Further, hydroxylamine used in the present step may be commercially available or can also be obtained by reacting hydroxylamine hydrochloride or hydroxylamine sulfate with a base. Examples of the base to be used include sodium hydrogen carbonate, potassium carbonate, potassium tert-butoxide, sodium hydroxide, potassium hydroxide, triethylamine, N,N-diisopropylethylamine, and the like.

Step 4-2

A compound (Ic) of the present invention can be prepared by reacting the compound (16) with a cyclizing agent in the presence of a base in a solvent. Examples of the solvent to be used include tetrahydrofuran, N,N-dimethylformamide, dimethylsulfoxide, dichloromethane, ethanol, a mixed solvent thereof, and the like. Examples of the base to be used include 1,8-diazabicyclo[5.4.0]undec-7-ene (DBU), triethylamine, N,N-diisopropylethylamine, pyridine, sodium ethoxide, and the like. Examples of the cyclizing agent to be used include 1,1'-carbonyldiimidazole, ethyl chloroformate, diethyl carbonate, and the like. The reaction temperature is usually 0° C. to solvent reflux temperature. The reaction time varies depending on a starting material to be used, a solvent to be used, a reaction temperature, or the like, but it is usually 30 minutes to 1 day.

Step 4-3

A compound (Id) of the present invention can be prepared by reacting the compound (16) with 1,1'-thiocarbonyldiimidazole in a solvent and then treating the product with an acid. Examples of the solvent to be used include tetrahydrofuran. Examples of the acid to be used include Lewis acids such as boron trifluoride diethyl ether complex and the like, a silica gel, and the like. The reaction temperature is usually 0° C. to solvent reflux temperature. The reaction time varies depending on a starting material to be used, a solvent to be used, a reaction temperature, or the like, but it is usually 30 minutes to 5 days.

Step 4-4

A compound (Ie) of the present invention can be prepared by reacting the compound (16) with 1,1'-thiocarbonyldiimidazole in the presence of a base in a solvent. Examples of the solvent to be used include tetrahydrofuran, 1,4-dioxane, acetonitrile, a mixed solvent thereof, and the like. Examples of the base to be used include 1,8-diazabicyclo[5.4.0]undec-7-ene (DBU), 1,5-diazabicyclo[4.3.0]non-5-ene (DBN), and the like. The reaction temperature is usually 0° C. to solvent reflux temperature. The reaction time varies depending on a starting material to be used, a solvent to be used, a reaction temperature, or the like, but it is usually 30 minutes to 3 days.

Step 4-5

A compound (If) of the present invention can be prepared by reacting the compound (16) with thionyl chloride in the presence of a base in a solvent. Examples of the solvent to be used include tetrahydrofuran, dichloromethane, toluene, a mixed solvent thereof, and the like. Examples of the base to be used include pyridine, triethylamine, N,N-diisopropylethylamine, and the like. The reaction temperature is usually 0° C. to solvent reflux temperature. The reaction time varies depending on a starting material to be used, a solvent to be used, a reaction temperature, or the like, but it is usually 30 minutes to 1 day.

Among the compounds (I) of the present invention, a compound (Ig) in which $R^1$ is —C(=O)—NH—OH can be prepared by the method shown in Scheme 5 or a similar method thereto, or according to a method described in other literature or a similar method thereto. If a protective group is necessary, combinations of introduction and cleavage can be appropriately carried out in accordance with usual methods.

Scheme 5

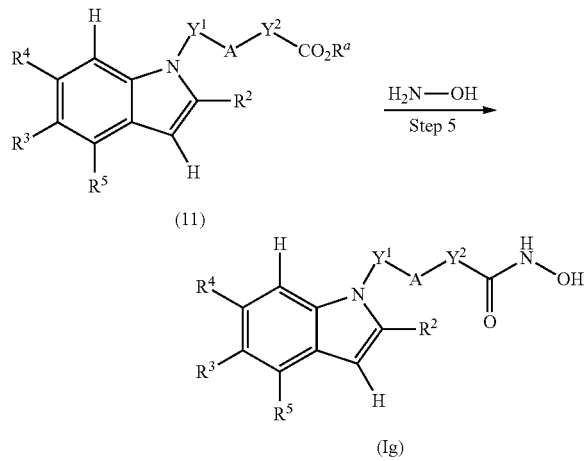

(wherein A, $R^2$, $R^3$, $R^4$, $R^5$, $Y^1$, $Y^2$, and $R^a$ have the same meanings as defined above.)

The compound (11) can be prepared by the method shown in Scheme 2 or a similar method thereto, or according to a method described in other literature or a similar method thereto.

Step 5

The compound (Ig) of the present invention can be prepared by reacting the compound (11) with hydroxylamine in a solvent. Examples of the solvent to be used include methanol, water, tetrahydrofuran, 1,4-dioxane, a mixed solvent thereof, and the like. The present step is preferably carried out upon addition of a base as necessary. Examples of the base to be used include sodium hydroxide, potassium hydroxide, sodium methoxide, potassium tert-butoxide, and the like. The reaction temperature is usually 0° C. to solvent reflux temperature. The reaction time varies depending on a starting material to be used, a solvent to be used, a reaction temperature, or the like, but it is usually 30 minutes to 3 days.

Further, hydroxylamine used in the present step may be commercially available or can also be obtained by reacting hydroxylamine hydrochloride or hydroxylamine sulfate with a base. Examples of the base to be used include sodium hydrogen carbonate, potassium carbonate, potassium tert-butoxide, sodium hydroxide, potassium hydroxide, triethylamine, N,N-diisopropylethylamine, and the like.

Among the compounds (I) of the present invention, a compound (Ih) in which $R^1$ is —C(=O)—NH—CN can be prepared by the method shown in Scheme 6 or a similar method thereto, or according to a method described in other literature or a similar method thereto. If a protective group is necessary, combinations of introduction and cleavage can be appropriately carried out in accordance with usual methods.

Scheme 6

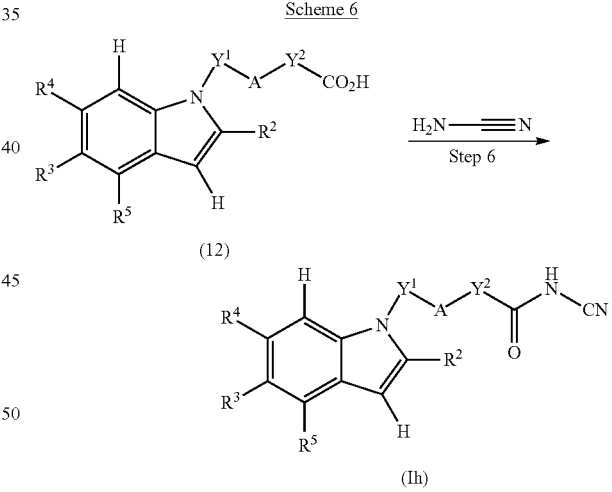

(wherein A, $R^2$, $R^3$, $R^4$, $R^5$, $Y^1$, and $Y^2$ have the same meanings as defined above.)

The compound (12) can be prepared by the method shown in Scheme 2 or a similar method thereto, or according to a method described in other literature or a similar method thereto.

Step 6

The compound (Ih) of the present invention can be prepared by reacting the compound (12) with cyanamide in the presence of a condensing agent in a solvent. Examples of the solvent to be used include dichloromethane, N,N-dimethylformamide, tetrahydrofuran, acetonitrile, a mixed solvent thereof, and the like. Examples of the condensing agent to be used include 1-ethyl-3-(3-dimethylaminopropyl)carbodiimide hydrochloride (EDC), N,N'-dicyclohexylcarbodiimide (DCC), and the like. The present step is preferably carried out upon addition of a tertiary amine, as necessary. Examples of the tertiary amine to be used include 4-dimethylaminopyridine, triethylamine, N,N-diisopropylethylamine, and the like. The reaction temperature is usually 0° C. to solvent reflux temperature. The reaction time varies depending on a starting material to be used, a solvent to be used, a reaction temperature, or the like, but it is usually 30 minutes to 3 days.

Among the compounds (I) of the present invention, a compound (Ii) in which $R^1$ is the formula:

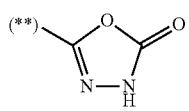

can be prepared by the method shown in Scheme 7 or a similar method thereto, or according to a method described in other literature or a similar method thereto. If a protective group is necessary, combinations of introduction and cleavage can be appropriately carried out in accordance with usual methods.

Scheme 7

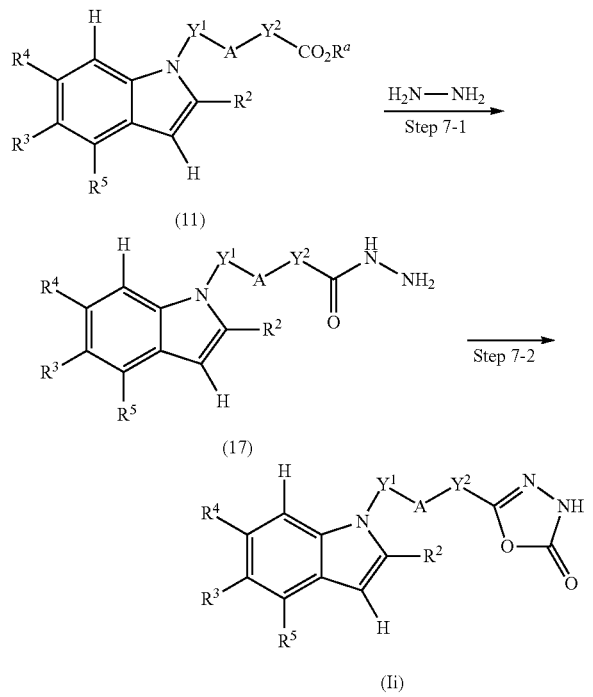

(wherein A, $R^2$, $R^3$, $R^4$, $R^5$, $Y^1$, $Y^2$, and $R^a$ have the same meanings as defined above.)

The compound (11) can be prepared by the method shown in Scheme 2 or a similar method thereto, or according to a method described in other literature or a similar method thereto.

Step 7-1

A compound (17) can be prepared by reacting the compound (11) with a hydrazine monohydrate in a solvent. Examples of the solvent to be used include water, methanol, ethanol, tetrahydrofuran, 1,4-dioxane, dichloromethane, toluene, a mixed solvent thereof, and the like. The reaction temperature is usually room temperature to solvent reflux temperature. The reaction time varies depending on a starting material to be used, a solvent to be used, a reaction temperature, or the like, but it is usually 30 minutes to 3 days.

Step 7-2

The compound (Ii) of the present invention can be prepared by reacting the compound (17) with a cyclizing agent in a solvent. Examples of the solvent to be used include tetrahydrofuran, 1,4-dioxane, N,N-dimethylformamide, dichloromethane, toluene, water, a mixed solvent thereof, and the like. Examples of the cyclizing agent to be used include 1,1'-carbonyldiimidazole, phosgene, diethyl carbonate, and the like. The present step can be carried in the presence of a base, as necessary. Examples of the base to be used include triethylamine, N,N-diisopropylethylamine, pyridine, potassium carbonate, sodium hydrogen carbonate, and the like. The reaction temperature is usually 0° C. to solvent reflux temperature. The reaction time varies depending on a starting material to be used, a solvent to be used, a reaction temperature, or the like, but it is usually 30 minutes to 1 day.

Among the compounds (I) of the present invention, a compound (Ij) in which $R^1$ is the formula:

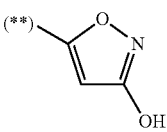

can be prepared by the method shown in Scheme 8 or a similar method thereto, or according to a method described in other literature or a similar method thereto. If a protective group is necessary, combinations of introduction and cleavage can be appropriately carried out in accordance with usual methods.

Scheme 8

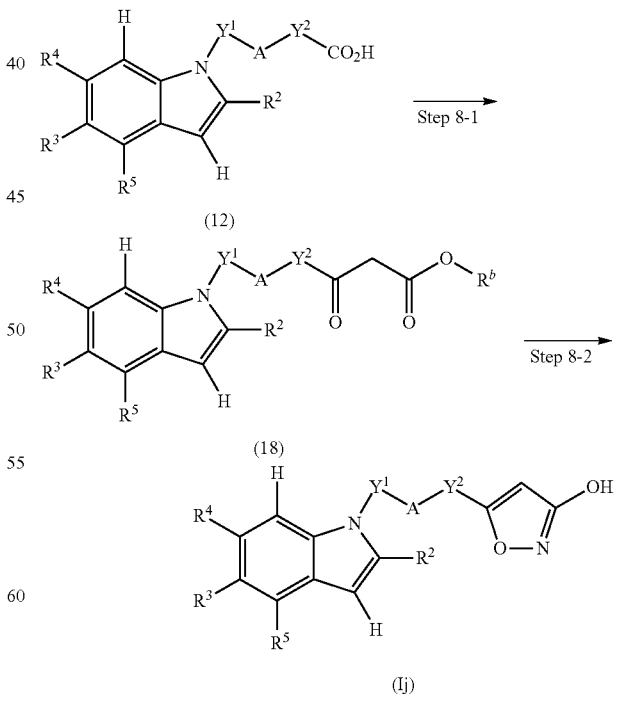

(wherein A, $R^2$, $R^3$, $R^4$, $R^5$, $Y^1$, and $Y^2$ have the same meanings as defined above, and $R^b$ represents a $C_{1-6}$ alkyl group.)

The compound (12) can be prepared by the method shown in Scheme 2 or a similar method thereto, or according to a method described in other literature or a similar method thereto.

Step 8-1

A compound (18) can be prepared by reacting a reactive derivative of the compound (12) with malonic acid monoester potassium salt that has been treated with magnesium chloride and a base in a solvent and then treating the product with an acid. Examples of the solvent to be used include acetonitrile, tetrahydrofuran, dichloromethane, ethyl acetate, a mixed solvent thereof, and the like. Examples of the base to be used include triethylamine, N,N-diisopropylethylamine, and the like. Examples of the acid to be used include hydrochloric acid, phosphoric acid, sulfuric acid, methanesulfonic acid, and the like. The reaction temperature is usually 0° C. to solvent reflux temperature. The reaction time varies depending on a starting material to be used, a solvent to be used, a reaction temperature, or the like, but it is usually 30 minutes to 3 days.

Examples of the reactive derivative of the compound (12) to be used in the present step include an acid halide (acid chloride, acid bromide, and the like), an acid amide (an acid amide with pyrazole, imidazole, benzotriazole and the like), and the like. The acid halide can be prepared by reacting the compound (12) with a halogenating agent such as oxalyl chloride, thionyl chloride, and the like. The acid amide can be prepared by reacting the compound (12) with, for example, 1,1'-carbonyldiimidazole. Further, the reactive derivative of the compound (12) can be prepared according to a method described in other literature or a similar method thereto.

Step 8-2

The compound (1j) of the present invention can be prepared by reacting the compound (18) with hydroxylamine in the presence of a base in a solvent and then treating the product with an acid. Examples of the solvent to be used include water, methanol, ethanol, tetrahydrofuran, a mixed solvent thereof, and the like. Examples of the base to be used include sodium hydroxide, potassium hydroxide, sodium methoxide, potassium tert-butoxide, and the like. Examples of the acid to be used include hydrochloric acid, sulfuric acid, and the like. The reaction temperature is usually −60° C. to solvent reflux temperature. The reaction time varies depending on a starting material to be used, a solvent to be used, a reaction temperature, or the like, but it is usually 30 minutes to 1 day.

Further, hydroxylamine used in the present step may be commercially available or can also be obtained by reacting hydroxylamine hydrochloride or hydroxylamine sulfate with a base. Examples of the base to be used include sodium hydrogen carbonate, potassium carbonate, potassium tert-butoxide, sodium hydroxide, potassium hydroxide, triethylamine, N,N-diisopropylethylamine, and the like.

Among the compounds (I) of the present invention, a compound (1k) in which $R^1$ is the formula:

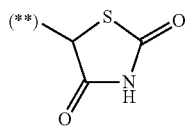

can be prepared by the method shown in Scheme 9 or a similar method thereto, or according to a method described in other literature or a similar method thereto. If a protective group is necessary, combinations of introduction and cleavage can be appropriately carried out in accordance with usual methods.

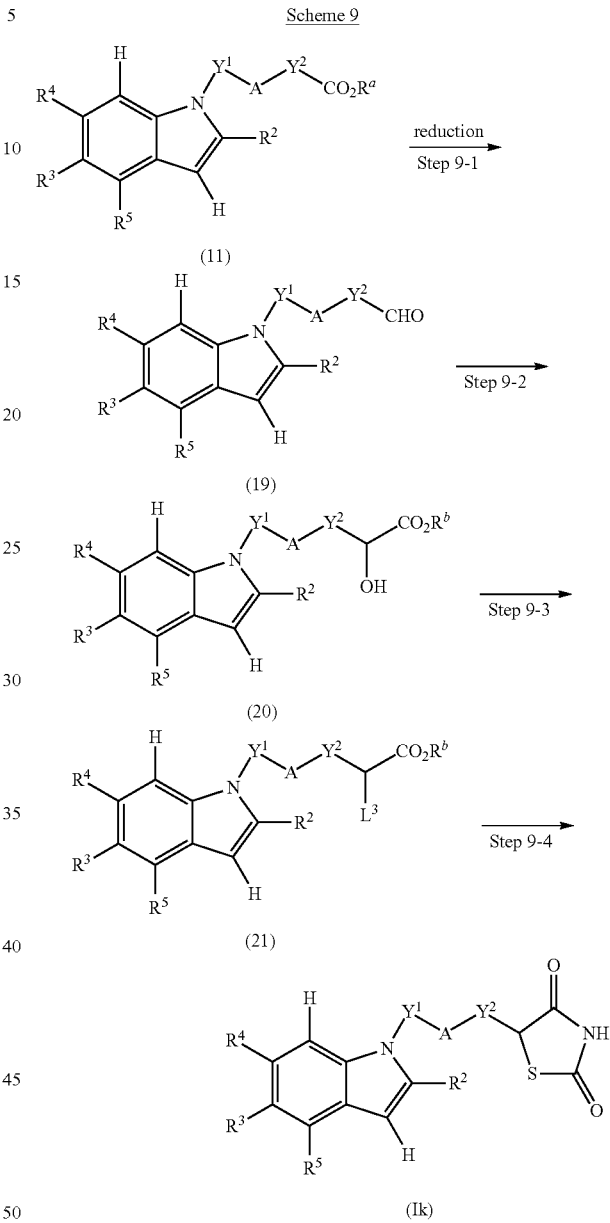

(wherein A, $R^2$, $R^3$, $R^4$, $R^5$, $Y^1$, $Y^2$, $R^a$, and $R^b$ have the same meanings as defined above, and $L^3$ represents a leaving group such as a chlorine atom, a bromine atom, an iodine atom, a methanesulfonyloxy group, and the like.)

The compound (11) can be prepared by the method shown in Scheme 2 or a similar method thereto, or according to a method described in other literature or a similar method thereto.

Step 9-1

A compound (19) can be prepared by treating the compound (11) according to a method for converting an ester group into an aldehyde group. For example, the compound (19) can be prepared by applying the method described below in detail, a method that would be obvious to a skilled person in the art, or by a variation of such methods.

The compound (19) can be prepared by reducing the compound (11) in the presence of a reducing agent in a solvent. Examples of the solvent to be used include tetrahydrofuran, diethyl ether, toluene, dichloromethane, a mixed solvent thereof, and the like. Examples of the reducing agent to be used include diisobutylaluminum hydride, sodium bis(2-methoxyethoxy)aluminumhydride (Red-Al), and the like. The reaction temperature is usually −78° C. to room temperature. The reaction time varies depending on a starting material to be used, a solvent to be used, a reaction temperature, or the like, but it is usually 30 minutes to 1 day.

Step 9-2

A compound (20) can be prepared by treating a corresponding cyanohydrin or 1-(trimethylsilyloxy)nitrile with an acid in a solvent. Examples of the solvent to be used include alcohols such as methanol, ethanol, and the like. Examples of the acid to be used include hydrochloric acid, hydrobromic acid, concentrated sulfuric acid, methanesulfonic acid, p-toluenesulfonic acid, and the like.

Further, in the present step, an ester corresponding to the solvent that is used can be prepared. For example, in the case where methanol is used as a solvent, an ester in which $R^b$ is a methyl group can be prepared. The reaction temperature is usually room temperature to solvent reflux temperature. The reaction time varies depending on a starting material to be used, a solvent to be used, a reaction temperature, or the like, but it is usually 30 minutes to 3 days.

The cyanohydrin used in the present step can be prepared by reacting the compound (19) with a cyanating agent in the presence of an acid in a solvent. Examples of the solvent to be used include water, methanol, ethanol, tetrahydrofuran, diethyl ether, dichloromethane, ethyl acetate, a mixed solvent thereof, and the like. Examples of the cyanating agent include sodium cyanide, potassium cyanide, trimethylsilyl cyanide, and the like. Examples of the acid to be used include hydrochloric acid, sulfuric acid, acetic acid, ammonium chloride, Lewis acids such as zinc iodide, and the like. The reaction temperature is usually −78° C. to room temperature. The reaction time varies depending on a starting material to be used, a solvent to be used, a reaction temperature, or the like, but it is usually 30 minutes to 3 days. On the other hand, the 1-(trimethylsilyloxy)nitrile can be prepared by reacting the compound (19) with trimethylsilyl cyanide in the presence of an acid or a base in a solvent. Examples of the solvent to be used include tetrahydrofuran, diethyl ether, dichloromethane, N,N-dimethylformamide, acetonitrile, a mixed solvent thereof, and the like. Examples of the acid to be used include Lewis acids such as zinc iodide, and the like. Examples of the base to be used include triethylamine, N,N-diisopropylethylamine, potassium carbonate, and the like. The reaction temperature is usually −78° C. to solvent reflux temperature. The reaction time varies depending on a starting material to be used, a solvent to be used, a reaction temperature, or the like, but it is usually 30 minutes to 3 days.

Step 9-3

A compound (21) can be prepared by treating the compound (20) according to a method for converting a hydroxy group to a chlorine atom, a bromine atom, an iodine atom, or a methanesulfonyloxy group. For example, the compound (21) can be prepared by applying the method described below in detail, a method that would be obvious to a skilled person in the art, or by a variation of such methods.

The compound (21) in which $L^3$ is a chlorine atom can be prepared by reacting the compound (20) with thionyl chloride in a solvent. Examples of the solvent to be used include tetrahydrofuran, diethyl ether, toluene, dichloromethane, pyridine, a mixed solvent thereof, and the like. The present step can be carried out upon addition of a base, as necessary. Examples of the base to be used include pyridine, triethylamine, N,N-diisopropylethylamine, and the like. The reaction temperature is usually −78° C. to solvent reflux temperature. The reaction time varies depending on a starting material to be used, a solvent to be used, a reaction temperature, or the like, but it is usually 30 minutes to 1 day.

Step 9-4

The compound (Ik) of the present invention can be prepared by reacting the compound (21) with thiourea in the presence of a base in a solvent and then treating the product with an acid. Examples of the solvent to be used include water, methanol, ethanol, isopropyl alcohol, acetone, 1,4-dioxane, a mixed solvent thereof, and the like. Examples of the base to be used include sodium acetate, potassium carbonate, triethylamine, N,N-diisopropylethylamine, pyridine, and the like. Examples of the acid to be used include hydrochloric acid, sulfuric acid, p-toluenesulfonic acid, and the like. The reaction temperature is usually 0° C. to solvent reflux temperature. The reaction time varies depending on a starting material to be used, a solvent to be used, a reaction temperature, or the like, but it is usually 30 minutes to 3 days.

The compound (15) can be prepared by the method shown in Scheme 10 or a similar method thereto, or according to a method described in other literature or a similar method thereto. If a protective group is necessary, combinations of introduction and cleavage can be appropriately carried out in accordance with usual methods.

Scheme 10

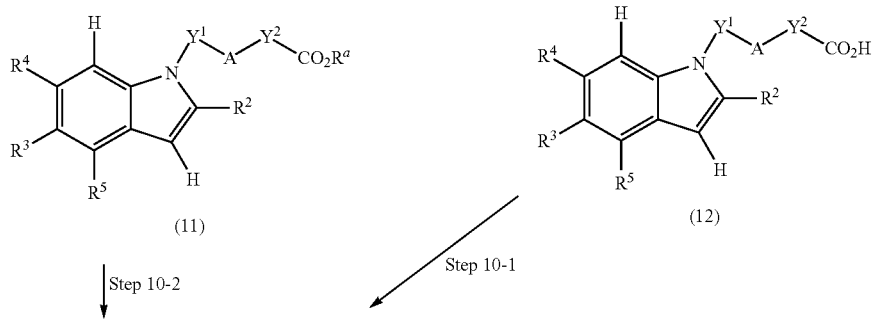

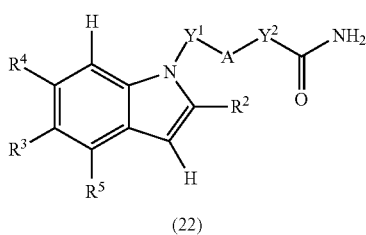 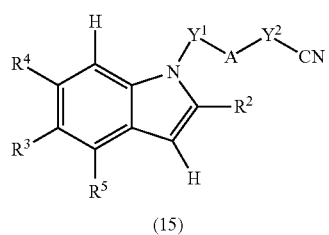

(22) Step 10-3 (15)

(wherein A, $R^2$, $R^3$, $R^4$, $R^5$, $Y^1$, $Y^2$, and $R^a$ have the same meanings as defined above.)

Step 10-1

A compound (22) can be prepared by treating the compound (12) according to a method for converting a carboxyl group to a carbamoyl group. An example of this method is a method in which a carboxyl group is activated by a condensing agent in the presence or absence of a base in a solvent to undergo a reaction with ammonia or ammonium chloride. Examples of the solvent to be used include tetrahydrofuran, N,N-dimethylformamide, dichloromethane, a mixed solvent thereof, and the like. Examples of the base to be used include 4-dimethylaminopyridine, pyridine, triethylamine, N,N-diisopropylethylamine, and the like. Examples of the condensing agent to be used include 1-ethyl-3-(3-dimethylaminopropyl)carbodiimide hydrochloride (EDC), N,N'-dicyclohexylcarbodiimide (DCC), 1,1'-carbonyldiimidazole, diphenylphosphorylazide, and the like. The reaction temperature is usually −20° C. to solvent reflux temperature. The reaction time varies depending on a starting material to be used, a solvent to be used, a reaction temperature, or the like, but it is usually 30 minutes to 3 days.

Step 10-2

The compound (22) can be prepared by reacting the compound (11) with ammonia in a solvent. Examples of the solvent to be used include water, methanol, ethanol, tetrahydrofuran, a mixed solvent thereof, and the like. The reaction temperature is usually 0° C. to solvent reflux temperature. The reaction time varies depending on a starting material to be used, a solvent to be used, a reaction temperature, or the like, but it is usually 30 minutes to 3 days.

Step 10-3

The compound (15) can be prepared by reacting the compound (22) with a dehydrating reagent in the presence or absence of a base in a solvent. Examples of the solvent to be used include dichloromethane, chloroform, toluene, N,N-dimethylformamide, a mixed solvent thereof, and the like. Examples of the base to be used include pyridine, triethylamine, N,N-diisopropylethylamine, and the like. Examples of the dehydrating reagent to be used include phosphoryl chloride, trifluoromethanesulfonic anhydride, phosphorus pentachloride, trifluoroacetic anhydride, and the like. The reaction temperature is usually −20° C. to solvent reflux temperature. The reaction time varies depending on a starting material to be used, a solvent to be used, a reaction temperature, or the like, but it is usually 30 minutes to 3 days.

The schemes shown above are examples of the method for preparing the compound (I) of the present invention or an intermediate for preparation thereof. They can be modified into various schemes that can be easily understood by a skilled person in the art.

Also, in the case that a protective group is necessary according to the kind of the functional group, combinations of introduction and cleavage can be appropriately carried out in accordance with usual methods. The type, introduction, and cleavage of the protective group is exemplified by the descriptions in, for example, "Greene's Protective Groups in Organic Synthesis", edited by Theodra W. Greene & Peter G. M. Wuts, fourth edition, Wiley-Interscience, 2006.

The compound (I) of the present invention or a pharmaceutically acceptable salt thereof, and an intermediate for preparation thereof used to prepare the compound (I) can be isolated/purified, as necessary, by solvent extraction, crystallization/recrystallization, chromatography, preparative high performance liquid chromatography, or the like, which are isolation/purification means known to a skilled person in the art of the relevant field.

Pharmaceutical Composition comprising Compound (I) of the Present Invention or Pharmaceutically Acceptable Salt thereof.

The pharmaceutical composition comprising the compound (I) of the present invention or a pharmaceutically acceptable salt thereof as an active ingredient is used in various dosage forms according to the usage. Examples of the dosage forms include powders, granules, fine granules, dry syrups, tablets, capsules, injections, liquids, ointments, suppositories, plasters, sublinguals, and the like, which are administered orally or parenterally.

These pharmaceutical compositions can be prepared by appropriately mixing or diluting/dissolving with appropriate pharmaceutical additives such as an excipient, a disintegrant, a binder, a lubricant, a diluent, a buffering agent, a tonicity agent, a preservative, a wetting agent, an emulsifier, a dispersant, a stabilizer, a solubilizing aid, and the like by a known method according to the dosage form. In addition, when the compound (I) of the present invention or a pharmaceutically acceptable salt thereof is used in combination with agents other than the $EP_1$ receptor antagonist, the pharmaceutical compositions can be prepared by formulating the respective active ingredients simultaneously or separately in the same way as described above.

Pharmaceutical Use of Compound (I) of the Present Invention or Pharmaceutically Acceptable Salt thereof The compound (I) of the present invention or a pharmaceutically acceptable salt thereof exhibits a potent $EP_1$ receptor antagonism in a test for confirmation of an $EP_1$ receptor antagonism and the like. Therefore, the compound (I) of the present invention can decrease the intracellular calcium concentration. Accordingly, a pharmaceutical composition comprising the compound (I) of the present invention or a pharmaceutically acceptable salt thereof as an active ingredient can be used as an agent for treating or preventing diseases or symptoms caused by activation of the $EP_1$ receptor due to stimulus of a $PGE_2$.

In addition, examples of diseases in which the $EP_1$ receptor is activated due to the $PGE_2$ stimulus include lower urinary tract symptoms (LUTS), inflammatory diseases, pain diseases, osteoporosis, cancer, and the like. The pharmaceutical composition comprising the compound (I) of the present invention or a pharmaceutically acceptable salt thereof as an active ingredient is preferably used as an agent for treating or preventing LUTS, inflammatory diseases, or pain diseases, and more preferably LUTS.

Examples of diseases that cause lower urinary tract symptoms include overactive bladder (OAB), benign prostatic hyperplasia (BPH), cystitis such as interstitial cystitis and the like, or prostatitis, and the like.

The "lower urinary tract symptoms" mean storage symptoms, voiding symptoms, post micturition symptoms, or the like. The compound (I) of the present invention or a pharmaceutically acceptable salt thereof is preferably used for treatment or prevention of storage symptoms.

Examples of the "storage symptoms" include urinary urgency, increased daytime frequency, nocturia, urinary incontinence (stress urinary incontinence, urge urinary incontinence, mixed urinary incontinence, enuresis, nocturnal enuresis, continuous urinary incontinence, and the like), and bladder sensation (increased bladder sensation, reduced bladder sensation, absent bladder sensation, non-specific bladder sensation, and the like). The compound (I) of the present invention or a pharmaceutically acceptable salt thereof is preferably used for treatment or prevention of urinary urgency, increased daytime frequency, nocturia, urge urinary incontinence, mixed urinary incontinence, enuresis, nocturnal enuresis, increased bladder sensation, or non-specific bladder sensation. It is more preferably urinary urgency, increased daytime frequency, nocturia, urge urinary incontinence, or increased bladder sensation. Further, the compound (I) of the present invention or a pharmaceutically acceptable salt thereof is particularly preferably used for treatment or prevention of OABs.

Combinations or Mixtures of Compound (I) of the Present Invention or Pharmaceutically Acceptable Salt thereof The compound (I) of the present invention or a pharmaceutically acceptable salt thereof can also be appropriately used in combination with at least one agent other than the $EP_1$ receptor antagonist.

Examples of the agent that can be used in combination with the compound (I) of the present invention or a pharmaceutically acceptable salt thereof include agents for treatment of overactive bladder (OAB), benign prostatic hyperplasia (BPH), cystitis such as interstitial cystitis and the like, prostatitis, and the like, which have different action mechanisms from that of the $EP_1$ receptor antagonist. Examples of such agents include an anticholinergic agent, an $\alpha_1$ antagonist, a $\beta$ agonist, a 5α-reductase inhibitor, a PDE inhibitor, an acetylcholine esterase inhibitor, an anti-androgen, a progesterone-based hormone, an LH-RH analog, a neurokinin inhibitor, an anti-diuretic, a calcium channel blocker, a direct smooth muscle agonist, a tricyclic antidepressant, a potassium channel modulator, a sodium channel blocker, an $H_1$ blocker, a serotonin reuptake inhibitor, a norepinephrine reuptake inhibitor, a dopamine reuptake inhibitor, a GABA agonist, a TRPV 1 modulator, an endothelin antagonist, a $5-HT_{1A}$ antagonist, an $\alpha_1$ agonist, an opioid agonist, a $P_2X$ antagonist, a COX inhibitor, a σ agonist, a muscarinic agonist, and the like. Such agents are preferably an anticholinergic agent, an $\alpha_1$ antagonist, a β agonist, a 5α-reductase inhibitor, a PDE inhibitor, a progesterone-based hormone, an anti-diuretic, a direct smooth muscle agonist, or a tricyclic antidepressant; more preferably an anticholinergic agent, an $\alpha_1$ antagonist, a β agonist, a direct smooth muscle agonist, or a tricyclic antidepressant; further more preferably an anticholinergic agent, an $\alpha_1$ antagonist, or a tricyclic antidepressant; and most preferably an anticholinergic agent.

Furthermore, concrete examples of the agent that is used in combination are illustrated as below, but the content of the present invention is not limited thereto. Further, examples of the concrete compounds include a free form thereof and other pharmaceutically acceptable salts.

Examples of the "anticholinergic agents" include oxybutynin, propiverine, solifenacin, tolterodine, imidafenacin, temiverine, darifenacin, fesoterodine, trospium, propantheline, and the like. It is preferably oxybutynin, propiverine, solifenacin, tolterodine, or imidafenacin; and more preferably solifenacin or imidafenacin.

Examples of the "$\alpha_1$ antagonist" include urapidil, naftopidil, tamsulosin, silodosin, prazosin, terazosin, alfuzosin, doxazosin, CR-2991, fiduxosin, and the like; preferably urapidil, naftopidil, tamsulosin, silodosin, prazosin, terazosin, or fiduxosin. It is more preferably tamsulosin, silodosin, or prazosin; and further preferably tamsulosin or silodosin. Silodosin is the most preferable.

Examples of the "β agonist" include mirabegron, KUC-7483, KRP-204, SM-350300, TRK-380, amibegron, clenbuterol, SAR-150640, solabegron, and the like. It is preferably mirabegron or KUC-7483; and more preferably mirabegron.

Examples of the "5α-reductase inhibitor" include dutasteride, TF-505, finasteride, izonsteride, and the like. It is preferably dutasteride or izonsteride.

The "PDE inhibitor" means a phosphodiesterase inhibitor. Examples of the "PDE inhibitor" include tadalafil, vardenafil, sildenafil, avanafil, UK-369003, T-0156, AKP-002, etazolate, and the like. It is preferably tadalafil, vardenafil, sildenafil, or avanafil.

Examples of the "acetylcholine esterase inhibitor" include distigmine, donepezil, Z-338, rivastigmine, ganstigmine, BGC-20-1259, galantamine, itopride, NP-61, SPH-1286, tolserine, ZT-1, and the like.

Examples of the "anti-androgen" include gestonorone, oxendolone, bicalutamide, BMS-641988, CB-03-01, CH-4892789, flutamide, MDV-3100, nilutamide, TAK-700, YM-580, and the like.

Examples of the "progesterone-based hormone" include chlormadinone, allylestrenol, and the like.

The "LH-RH analog" means a gonadotropin-releasing hormone analog. In addition, gonadotropin-releasing hormone is also called "luteinizing hormone-releasing hormone". Examples of the "LH-RH analog" include AEZS-108, buserelin, deslorelin, goserelin, histrelin, leuprorelin, lutropin, nafarelin, triptorelin, AEZS-019, cetrorelix, degarelix, elagolix, ganirelix, ozarelix, PTD-634, TAK-385, teverelix, TAK-448, TAK-683, and the like.

Examples of the "neurokinin inhibitor" include KRP-103, aprepitant, AV-608, casopitant, CP-122721, DNK-333, fosaprepitant, LY-686017, netupitant, orvepitant, rolapitant, TA-5538, T-2328, vestipitant, AZD-2624, Z-501, 1144814, MEN-15596, MEN-11420, SAR-102779, SAR-102279, saredutant, SSR-241586, and the like.

Examples of the "anti-diuretic" include desmopressin, VA-106483, and the like.

Examples of the "calcium channel blocker" include amlodipine, cilnidipine, propiverine, temiverine, PD-299685, aranidipine, azelnidipine, barnidipine, benidipine, bevantolol, clevidipine, CYC-381, diltiazem, efonidipine, fasudil, felodipine, gabapentin, gallopamil, isradipine, lacidipine, lercanidipine, lomerizine, manidipine, MEM-1003, nicardipine, nifedipine, nilvadipine, nimodipine, nisoldipine, SB-751689, verapamil, YM-58483, ziconotide, and the like.

Examples of the "direct smooth muscle agonist" include flavoxate and the like.

Examples of the "tricyclic antidepressant" include imipramine, clomipramine, amitriptyline, and the like. It is preferably imipramine Examples of the "potassium channel modulator" include nicorandil, NIP-141, NS-4591, NS-1643, andolast, diazoxide, ICA-105665, minoxidil, pinacidil, tilisolol, VRX-698, and the like.

Examples of the "sodium channel blocker" include bepridil, dronedarone, propafenone, safinamide, SUN-N8075, SMP-986, 1014802, 552-02, A-803467, brivaracetam, cibenzoline, eslicarbazepine, F-15845, flecamide, fosphenyloin, lacosamide, lamotrigine, levobupivacaine, M-58373, mexiletine, moracizine, nerispirdine, NW-3509, oxcarbazepine, pilsicamide, pirmenol, propafenone, NW-1029, ropivacaine, vernakalant, and the like.

Examples of the "$H_1$ blocker" include acrivastine, alcaftadine, bepotastine, bilastine, cetirizine, desloratadine, ebastine, efletirizine, epinastine, fexofenadine, GSK-835726, levocabastine, levocetirizine, loratadine, mequitazine, mizolastine, NBI-75043, ReN-1869, terfenadine, UCB-35440, vapitadine, YM-344484, diphenhydramine, chlorpheniramine, and the like.

Examples of the "serotonin reuptake inhibitor" include UCB-46331, 424887, AD-337, BGC-20-1259, BMS-505130, citalopram, dapoxetine, desvenlafaxine, DOV-102677, DOV-216303, DOV-21947, duloxetine, escitalopram, F-2695, F-98214-TA, fluoxetine, fluvoxamine, IDN-5491, milnacipran, minaprine, NS-2359, NSD-644, paroxetine, PF-184298, SD-726, SEP-225289, SEP-227162, SEP-228425, SEP-228432, sertraline, sibutramine, tesofensine, tramadol, trazodone, UCB-46331, venlafaxine, vilazodone, WAY-426, WF-516, and the like.

Examples of the "norepinephrine reuptake inhibitor" include AD-337, desvenlafaxine, DOV-102677, DOV-216303, DOV-21947, duloxetine, F-2695, F-98214-TA, milnacipran, NS-2359, NSD-644, PF-184298, SD-726, SEP-225289, SEP-227162, SEP-228425, SEP-228432, sibutramine, tesofensine, tramadol, venlafaxine, bupropion, radafaxine, atomoxetine, DDP-225, LY-2216684, neboglamine, NRI-193, reboxetine, tapentadol, WAY-256805, WAY-260022, and the like.

Examples of the "dopamine reuptake inhibitor" include DOV-102677, DOV-216303, DOV-21947, IDN-5491, NS-2359, NSD-644, SEP-225289, SEP-228425, SEP-228432, sibutramine, tesofensine, tramadol, brasofensine, bupropion, NS-27100, radafaxine, safinamide, and the like.

Examples of the "GABA agonist" include retigabine, eszopiclone, indiplon, pagoclone, SEP-225441, acamprosate, baclofen, AZD-7325, BL-1020, brotizolam, DP-VPA, progabide, propofol, topiramate, zopiclone, EVT-201, AZD-3043, ganaxolone, NS-11394, arbaclofen, AZD-3355, GS-39783, ADX-71441, ADX-71943, and the like.

Examples of the "TRPV1 modulator" include capsaicin, resiniferatoxin, DE-096, GRC-6211, AMG-8562, JTS-653, SB-705498, A-425619, A-784168, ABT-102, AMG-628, AZD-1386, JNJ-17203212, NGD-8243, PF-3864086, SAR-115740, SB-782443, and the like.

Examples of the "endothelin antagonist" include SB-234551, ACT-064992, ambrisentan, atrasentan, bosentan, clazosentan, darusentan, fandosentan, S-0139, TA-0201, TBC-3711, zibotentan, BMS-509701, PS-433540, and the like.

Examples of the "5-$HT_{1A}$ antagonist" include espindolol, lecozotan, lurasidone, E-2110, REC-0206, SB-649915, WAY-426, WF-516, and the like.

Examples of the "$\alpha_1$ agonist" include CM-2236, armodafinil, midodrine, modafinil, and the like.

Examples of the "opioid agonist" include morphine, TRK-130, DPI-125, DPI-3290, fentanyl, LIF-301, loperamide, loperamide oxide, remifentanil, tapentadol, WY-16225, oxycodone, PTI-202, PTI-721, ADL-5747, ADL-5859, DPI-221, DPI-353, IPP-102199, SN-11, ADL-10-0101, ADL-10-0116, asimadoline, buprenorphine, CR-665, CR-845, eptazocine, nalbuphine, nalfurafine, pentazocine, XEN-0548, W-212393, ZP-120, nalmefene, and the like.

Examples of the "$P_2X$ antagonist" include A-740003, AZ-11657312, AZD-9056, GSK-1482160, GSK-31481A, and the like.

The "COX inhibitor" means a cyclooxygenase inhibitor. Examples of the "COX inhibitor" include aceclofenac, ST-679, aspirin, bromfenac, dexketoprofen, flurbiprofen, FYO-750, ibuprofen, ketoprofen, ketorolac, licofelone, lornoxicam, loxoprofen, LT-NS001, diclofenac, mofezolac, nabumetone, naproxen, oxaprozin, piroxicam, pranoprofen, suprofen, tenoxicam, tiaprofenic acid, tolfenamic acid, zaltoprofen, 644784, ABT-963, ajulemic acid, apricoxib, celecoxib, cimicoxib, etoricoxib, iguratimod, lumiracoxib, meloxicam, nimesulide, parecoxib, RO-26-2198, valdecoxib, and the like.

Examples of the "σ agonist" include ANAVEX-27-1041, PRS-013, SA-4503, ANAVEX-2-73, siramesine, ANAVEX-7-1037, ANAVEX-1-41, and the like.

Examples of the "muscarinic agonist" include AC-260584, cevimeline, MCD-386, NGX-267, NGX-292, sabcomeline, pilocarpine, bethanechol, and the like.

When the compound (I) of the present invention or a pharmaceutically acceptable salt thereof is used in combination with one or more of the above-described agents, the pharmaceutical composition of the present invention includes one administration method selected from 1) to 5) below:

1) simultaneous administration by a combination preparation, 2) simultaneous administration by the same administration pathway as a separate formulation, 3) simultaneous administration by a different administration pathway as a separate formulation, 4) administration at different times by the same administration pathway as a separate formulation, and 5) administration at different times by a different administration pathway as a separate formulation. Further, in the case of administration at different times as a separate formulation as in 4) or 5), the order of administration of the compound (I) of the present invention and the above-described agents is not particularly limited.

Furthermore, the compound (I) of the present invention or a pharmaceutically acceptable salt thereof can be used appropriately in combination with one or more of the above-described agents to achieve an advantageous effect that is equal to or more than an additive effect in prevention or treatment of the above-described diseases. Alternatively, as compared with a case of being used alone, the amount used can be reduced, or the side effects of the agent(s) used together can be avoided or mitigated.

Usage/Dose of Compound (I) of the Present Invention

The pharmaceutical composition of the present invention can be administered systemically or locally, orally or parenterally (nasal, pulmonary, intravenous, rectal, subcutaneous, intramuscular, transdermal routes, and the like).

When the pharmaceutical composition of the present invention is used for practical treatments, the dose of the compound (I) of the present invention or a pharmaceutically acceptable salt thereof that is the active ingredient is appropriately determined by taking the patient's age, gender, weight, medical condition, degree of the treatment, and the like into consideration. For example, in a case of oral administration, administration can be conducted appropriately at a daily dose in the range from about 3 to 1000 mg for an adult (regarded as a body weight of 60 kg) in one portion or in several divided portions. The daily dose as an oral administration agent is preferably from 6 to 540 mg, and more preferably from 18 to 180 mg. In a case of parenteral administration, administration can be conducted appropriately at a daily dose in the range from about 0.01 to 300 mg for an adult in one portion or in several divided portions. The daily dose as a parenteral administration agent is preferably from 1 to 100 mg, and more preferably from 6 to 60 mg. In addition, the dose of the compound (I) of the present invention or a pharmaceutically acceptable salt thereof can be reduced according to the amount of the agent(s) other than an $EP_1$ receptor antagonist.

Hereinbelow, the present invention is illustrated in detail with reference to Examples, Reference Examples, and Test Examples, but the scope of the present invention is not limited thereto.

Among the symbols used in each of the Reference Examples, Examples, and Tables, Ex. No. means Example Number, Strc means a chemical structural formula, Physical Data means physical property values, $^1$H-NMR means a proton nuclear magnetic resonance spectrum, $CDCl_3$ means chloroform-d, and $DMSO-d_6$ means dimethylsulfoxide-$d_6$. Further, ESI-MS means mass spectroscopic spectrum data measured by an electrospray ionization method.

REFERENCE EXAMPLE 1

Methyl 6-(5-methoxy-2-phenylindol-1-ylmethyl)pyridine-2-carboxylate

Under an argon atmosphere, to a solution of 5-methoxy-2-phenyl-1H-indole (582 mg) in N,N-dimethylformamide (13 mL) was added sodium hydride (dispersed in liquid paraffin, 55% or more, 171 mg) under ice-cooling. This mixture was stirred for 5 minutes under ice-cooling, and then stirred for 30 minutes at room temperature. Subsequently, methyl 6-chloromethylpyridine-2-carboxylate (483 mg) was added thereto, followed by stirring at 80° C. for 18 hours. The reaction mixture was poured into an ice-cooled saturated aqueous ammonium chloride solution, and then ethyl acetate was added to the mixture to separate the organic layer. The aqueous layer was extracted twice with ethyl acetate. The combined organic layer was washed with saturated brine, dried over anhydrous sodium sulfate, and then concentrated under reduced pressure. The residue was purified by silica gel column chromatography (eluting solvent: ethyl acetate-hexane) to obtain the title compound (91 mg). $^1$H-NMR ($CDCl_3$) δ ppm: 3.87 (3H, s), 4.02 (3H, s), 5.58 (2H, s), 6.60-6.75 (2H, m), 6.81 (1H, dd, J=2.5, 8.8 Hz), 7.02 (1H, d, J=8.8 Hz), 7.15 (1H, d, J=2.5 Hz), 7.30-7.45 (5H, m), 7.60-7.70 (1H, m), 7.95-8.05 (1H, m).

REFERENCE EXAMPLE 2

6-(5-Methoxy-2-phenylindol-1-ylmethyl)pyridine-2-carboxylic acid

To a mixture of methyl 6-(5-methoxy-2-phenylindol-1-ylmethyl) pyridine-2-carboxylate (90 mg), tetrahydrofuran (1.8 mL), and methanol (0.9 mL), 1 mol/L aqueous sodium hydroxide solution (0.73 mL) was added at room temperature. The mixture was stirred at 50° C. for 2 hours. The reaction mixture was then concentrated under reduced pressure. The residue was diluted with water, and then 1 mol/L hydrochloric acid (0.75 mL) was added under ice-cooling. The obtained precipitate was collected by filtration, washed with water, and then dried under reduced pressure to obtain the title compound (84 mg). $^1$H-NMR ($DMSO-d_6$) δ ppm: 3.77 (3H, s), 5.53 (2H, s), 6.62 (1H, s), 6.65-6.80 (2H, m), 7.13 (1H, d, J=2.3 Hz), 7.24 (1H, d, J=9.0 Hz), 7.30-7.50 (3H, m), 7.50-7.65 (2H, m), 7.75-7.95 (2H, m), 12.85-13.65 (1H, br).

REFERENCE EXAMPLE 3

Ethyl 5-(5-methoxy-2-phenylindol-1-ylmethyl)furan-2-carboxylate

In the same method as in Reference Example 1 using the corresponding starting material and reaction agents, the title compound was synthesized. $^1$H-NMR ($CDCl_3$) δ ppm: 1.37 (3H, t, J=7.2 Hz), 3.87 (3H, s), 4.35 (2H, q, J=7.2 Hz), 5.29 (2H, s), 5.95-6.05 (1H, m), 6.50-6.60 (1H, m), 6.87 (1H, dd, J=2.4, 9.0 Hz), 7.05 (1H, d, J=3.5 Hz), 7.12 (1H, d, J=2.4 Hz), 7.19 (1H, d, J=9.0 Hz), 7.35-7.55 (5H, m).

REFERENCE EXAMPLE 4

5-(5-Methoxy-2-phenylindol-1-ylmethyl)furan-2-carboxylic acid

In the same method as in Reference Example 2 using the corresponding starting material and reaction agents, the title compound was synthesized. $^1$H-NMR ($DMSO-d_6$) δ ppm: 3.77 (3H, s), 5.41 (2H, s), 6.18 (1H, d, J=3.5 Hz), 6.54 (1H, s), 6.81 (1H, dd, J=2.5, 9.0 Hz), 7.07 (1H, d, J=3.5 Hz), 7.09 (1H, d, J=2.5 Hz), 7.40-7.65 (6H, m), 13.04 (1H, br s).

REFERENCE EXAMPLE 5

N-(2-Bromo-5-chloro-4-methoxyphenyl)-2,2,2-trifluoroacetamide

To a solution of 2-bromo-5-chloro-4-methoxyaniline (8.97 g) in pyridine (25.3 mL) was added dropwise trifluoroacetic anhydride (2.81 mL) under ice-cooling. This mixture was stirred at room temperature for 30 hours. To the reaction mixture was added methanol (1.5 mL), followed by stirring for 40 minutes. The reaction mixture was concentrated under reduced pressure. 1 mol/L hydrochloric acid was added to the residue, followed by extraction with ethyl acetate. The organic layer was washed with 1 mol/L hydrochloric acid, saturated aqueous sodium hydrogen carbonate solution, and saturated brine, and then dried over anhydrous sodium sulfate and concentrated under reduced pressure to obtain the title compound (3.45 g). $^1$H-NMR ($DMSO-d_6$) δ ppm: 3.92 (3H, s), 7.51 (1H, s), 7.61 (1H, s), 11.21 (1H, s).

REFERENCE EXAMPLE 6

6-Chloro-5-methoxy-2-phenyl-1H-indole

To a mixture of N-(2-bromo-5-chloro-4-methoxyphenyl)-2,2,2-trifluoroacetamide (512 mg), phenylacetylene (0.254 mL), copper(I) iodide (17.5 mg), triethylamine (0.549 mL), and acetonitrile (12.3 mL) was added bis(triphenylphosphine) palladium(II) dichloride (32.5 mg). The mixture was stirred at 120° C. for 2 hours under microwave irradiation. The reaction mixture was left to cool. To the reaction mixture was added potassium carbonate (532 mg). The mixture was stirred at 120° C. for 2 more hours under microwave irradiation. The reaction mixture was left to cool, and filtered through Celite (registered trademark). The filtrate was concentrated under reduced pressure. The residue was purified by aminopropylated silica gel column chromatography (eluting solvent: ethyl acetate-hexane) to obtain the title compound (255 mg). $^1$H-NMR (CDCl$_3$) δ ppm: 3.95 (3H, s), 6.70-6.80 (1H, m), 7.13 (1H, s), 7.30-7.50 (4H, m), 7.60-7.70 (2H, m), 8.00-8.40 (1H, br).

REFERENCE EXAMPLE 7

Methyl 6-(6-chloro-5-methoxy-2-phenylindol-1-ylmethyl)pyridine-2-carboxylate

In the same method as in Reference Example 1 using the corresponding starting material and reaction agents, the title compound was synthesized. $^1$H-NMR (CDCl$_3$) δ ppm: 3.96 (3H, s), 4.03 (3H, s), 5.54 (2H, s), 6.55-6.75 (2H, m), 7.15-7.25 (2H, m), 7.30-7.45 (5H, m), 7.69 (1H, t, J=7.8 Hz), 7.95-8.05 (1H, m).

REFERENCE EXAMPLE 8

6-(6-Chloro-5-methoxy-2-phenylindol-1-ylmethyl)pyridine-2-carboxylic acid

In the same method as in Reference Example 2 using the corresponding starting material and reaction agents, the title compound was synthesized. $^1$H-NMR (DMSO-d$_6$) δ ppm: 3.87 (3H, s), 5.55 (2H, s), 6.60-6.80 (2H, m), 7.32 (1H, s), 7.35-7.50 (3H, m), 7.50-7.60 (3H, m), 7.75-7.95 (2H, m), 12.80-13.70 (1H, br).

REFERENCE EXAMPLE 9

N-(2-Bromo-5-fluoro-4-methoxyphenyl)-2,2,2-trifluoroacetamide

In the same method as in Reference Example 5 using the corresponding starting material and reaction agents, the title compound was synthesized. $^1$H-NMR (DMSO-d$_6$) δ ppm: 3.90 (3H, s), 7.47 (1H, d, J=11.8 Hz), 7.54 (1H, d, J=8.8 Hz), 11.21 (1H, s).

REFERENCE EXAMPLE 10

6-Fluoro-5-methoxy-2-(thiophen-3-yl)-1H-indole

In the same method as in Reference Example 6 using the corresponding starting material and reaction agents, the title compound was synthesized.
$^1$H-NMR (CDCl$_3$) δ ppm: 3.93 (3H, s), 6.55-6.65 (1H, m), 7.05-7.15 (2H, m), 7.35-7.45 (3H, m), 8.16 (1H, br s).

REFERENCE EXAMPLE 11

Methyl 6-[6-fluoro-5-methoxy-2-(thiophen-3-yl)indol-1-ylmethyl]pyridine-2-carboxylate In the same method as in Reference Example 1 using the corresponding starting material and reaction agents, the title compound was synthesized. $^1$H-NMR (CDCl$_3$) δ ppm: 3.94 (3H, s), 4.04 (3H, s), 5.57 (2H, s), 6.63 (1H, d, J=0.5 Hz), 6.70-6.80 (1H, m), 6.89 (1H, d, J=11.4 Hz), 7.14 (1H, dd, J=1.3, 5.0 Hz), 7.18 (1H, d, J=8.2 Hz), 7.24 (1H, dd, J=1.3, 3.0 Hz), 7.36 (1H, dd, J=3.0, 5.0 Hz), 7.69 (1H, t, J=7.8 Hz), 8.00-8.05 (1H, m).

REFERENCE EXAMPLE 12

6-[6-Fluoro-5-methoxy-2-(thiophen-3-yl)indol-1-ylmethyl]pyridine-2-carboxylic acid In the same method as in Reference Example 2 using the corresponding starting material and reaction agents, the title compound was synthesized. $^1$H-NMR (DMSO-d$_6$) δ ppm: 3.85 (3H, s), 5.59 (2H, s), 6.68 (1H, s), 6.75-6.85 (1H, m), 7.29 (1H, d, J=8.5 Hz), 7.35 (1H, dd, J=1.3, 5.0 Hz), 7.39 (1H, d, J=12.2 Hz), 7.64 (1H, dd, J=2.9, 5.0 Hz), 7.75 (1H, dd, J=1.3, 2.9 Hz), 7.80-7.95 (2H, m), 13.05-13.40 (1H, br).

REFERENCE EXAMPLE 13 tert-Butyl (4-cyclopropyl-2-methylphenyl)carbamate

A mixture of tert-butyl (4-iodo-2-methylphenyl)carbamate (1.04 g), cyclopropylboronic acid monohydrate (422 mg), palladium(II) acetate (35.1 mg), tricyclohexylphosphine (87.5 mg), tripotassium phosphate monohydrate (2.52 g), toluene (8.7 mL), and water (0.87 mL) was stirred at 100° C. for 15 hours. The reaction mixture was left to cool and then diluted with ethyl acetate and filtered through Celite (registered trademark). The filtrate was washed with brine and dried over anhydrous sodium sulfate, and then concentrated under reduced pressure. The residue was purified by silica gel column chromatography (eluting solvent: ethyl acetate-hexane) to obtain the title compound (668 mg). $^1$H-NMR (CDCl$_3$) δ ppm: 0.55-0.70 (2H, m), 0.80-1.00 (2H, m), 1.51 (9H, s), 1.75-1.90 (1H, m), 2.21 (3H, s), 5.85-6.45 (1H, br), 6.75-7.00 (2H, m), 7.45-7.75 (1H, m).

REFERENCE EXAMPLE 14 tert-Butyl[4-cyclopropyl-2-(2-oxo-2-phenylethyl)phenyl]carbamate

Under an argon atmosphere, to a solution of tert-butyl (4-cyclopropyl-2-methylphenyl)carbamate (666 mg) in tetrahydrofuran (13.5 mL) was added dropwise sec-butyllithium (1.08 mol/L hexane-cyclohexane solution, 5.5 mL) at −45° C., and the mixture was stirred for 30 minutes. Next, a solution of N-methoxy-N-methylbenzamide (489 mg) in tetrahydrofuran (1.4 mL) was added dropwise thereto, and the mixture was stirred at −45° C. for 35 minutes and then stirred at room temperature for 2 more hours. The reaction mixture was quenched with saturated aqueous ammonium chloride solution/water (2/1, 30 mL), followed by extraction with ethyl acetate. The organic layer was washed with saturated brine, dried over anhydrous sodium sulfate, and then concentrated under reduced pressure. The residue was purified by silica gel column chromatography (eluting solvent: ethyl acetate-hexane) to obtain the title compound (563 mg). $^1$H-NMR (CDCl$_3$) δ ppm: 0.55-0.70 (2H, m), 0.80-1.00 (2H, m), 1.49 (9H, s), 1.75-1.90 (1H, m), 4.25 (2H, s), 6.85-7.00 (2H, m), 7.20-7.75 (5H, m), 8.00-8.15 (2H, m).

REFERENCE EXAMPLE 15

5-Cyclopropyl-2-phenyl-1H-indole

To a solution of tert-butyl[4-cyclopropyl-2-(2-oxo-2-phenylethyl)phenyl]carbamate (561 mg) in dichloromethane (8 mL) was added dropwise trifluoroacetic acid (1.6 mL) under ice-cooling. The mixture was heated to room temperature, and then stirred for 23 hours. The reaction mixture was concentrated under reduced pressure. To the residue were added ethyl acetate and saturated aqueous sodium hydrogen carbonate solution to separate the organic layer. The organic layer was washed with saturated brine, dried over anhydrous sodium sulfate, and then concentrated under reduced pressure. The residue was purified by silica gel column chromatography (eluting solvent: ethyl acetate-hexane) to obtain the title compound (317 mg). $^1$H-NMR (CDCl$_3$) δ ppm: 0.65-0.75 (2H, m), 0.85-1.00 (2H, m), 1.95-2.10 (1H, m), 6.70-6.80 (1H, m), 6.90-7.00 (1H, m), 7.25-7.50 (5H, m), 7.60-7.70 (2H, m), 8.24 (1H, br s).

REFERENCE EXAMPLE 16

Methyl 6-(5-cyclopropyl-2-phenylindol-1-ylmethyl)pyridine-2-carboxylate

In the same method as in Reference Example 1 using the corresponding starting material and reaction agents, the title compound was synthesized. $^1$H-NMR (CDCl$_3$) δ ppm: 0.65-0.75 (2H, m), 0.85-1.00 (2H, m), 1.95-2.10 (1H, m), 4.02 (3H, s), 5.58 (2H, s), 6.55-6.65 (1H, m), 6.65-6.75 (1H, m), 6.91 (1H, dd, J=1.9, 8.5 Hz), 7.01 (1H, d, J=8.5 Hz), 7.30-7.45 (6H, m), 7.65 (1H, t, J=7.9 Hz), 7.90-8.05 (1H, m).

REFERENCE EXAMPLE 17

6-(5-Cyclopropyl-2-phenylindol-1-ylmethyl)pyridine-2-carboxylic acid

In the same method as in Reference Example 2 using the corresponding starting material and reaction agents, the title compound was synthesized. $^1$H-NMR (DMSO-d$_6$) δ ppm: 0.55-0.70 (2H, m), 0.85-0.95 (2H, m), 1.90-2.05 (1H, m), 5.52 (2H, s), 6.60 (1H, s), 6.72 (1H, d, J=7.6 Hz), 6.86 (1H, dd, J=1.6, 8.5 Hz), 7.20 (1H, d, J=8.5 Hz), 7.25-7.65 (6H, m), 7.75-7.90 (2H, m), 12.00-14.50 (1H, br).

REFERENCE EXAMPLE 18

Methyl 6-(5-chloro-2-phenylindol-1-ylmethyl)pyridine-2-carboxylate

In the same method as in Reference Example 1 using the corresponding starting material and reaction agents, the title compound was synthesized. $^1$H-NMR (CDCl$_3$) δ ppm: 4.03 (3H, s), 5.59 (2H, s), 6.60-6.70 (2H, m), 7.00-7.15 (2H, m), 7.35-7.45 (5H, m), 7.60-7.75 (2H, m), 7.95-8.05 (1H, m).

REFERENCE EXAMPLE 19

6-(5-Chloro-2-phenylindol-1-ylmethyl)pyridine-2-carboxylic acid

In the same method as in Reference Example 2 using the corresponding starting material and reaction agents, the title compound was synthesized. $^1$H-NMR (CDCl$_3$) δ ppm: 5.52 (2H, s), 6.63 (1H, s), 6.85-7.25 (3H, m), 7.30-7.50 (5H, m), 7.55-7.90 (2H, m), 8.00-8.15 (1H, m).

REFERENCE EXAMPLE 20

Ethyl 5-(6-chloro-5-methoxy-2-phenylindol-1-ylmethyl)furan-2-carboxylate

In the same method as in Reference Example 1 using the corresponding starting material and reaction agents, the title compound was synthesized. $^1$H-NMR (CDCl$_3$) δ ppm: 1.37 (3H, t, J=7.1 Hz), 3.95 (3H, s), 4.35 (2H, q, J=7.1 Hz), 5.25 (2H, s), 5.95-6.05 (1H, m), 6.50-6.60 (1H, m), 7.06 (1H, d, J=3.5 Hz), 7.15 (1H, s), 7.30-7.55 (6H, m).

REFERENCE EXAMPLE 21

5-(6-Chloro-5-methoxy-2-phenylindol-1-ylmethyl)furan-2-carboxylic acid

In the same method as in Reference Example 2 using the corresponding starting material and reaction agents, the title compound was synthesized. $^1$H-NMR (DMSO-d$_6$) δ ppm: 3.86 (3H, s), 5.44 (2H, s), 6.16 (1H, d, J=3.3 Hz), 6.55-6.65 (1H, m), 7.05 (1H, d, J=3.3 Hz), 7.28 (1H, s), 7.40-7.65 (5H, m), 7.72 (1H, s), 12.50-13.50 (1H, br).

REFERENCE EXAMPLE 22

Methyl 3-(5-methoxy-2-phenylindol-1-ylmethyl)benzoate

In the same method as in Reference Example 1 using the corresponding starting material and reaction agents, the title compound was synthesized. $^1$H-NMR (CDCl$_3$) δ ppm: 3.86 (3H, s), 3.89 (3H, s), 5.36 (2H, s), 6.55-6.65 (1H, m), 6.80 (1H, dd, J=2.5, 8.8 Hz), 7.03 (1H, d, J=8.8 Hz), 7.05-7.20 (2H, m), 7.25-7.50 (6H, m), 7.75-7.85 (1H, m), 7.85-7.95 (1H, m).

REFERENCE EXAMPLE 23

3-(5-Methoxy-2-phenylindol-1-ylmethyl)benzoic acid

In the same method as in Reference Example 2 using the corresponding starting material and reaction agents, the title compound was synthesized. $^1$H-NMR (DMSO-d$_6$) δ ppm: 3.77 (3H, s), 5.50 (2H, s), 6.60 (1H, s), 6.76 (1H, dd, J=2.5, 8.8 Hz), 7.05-7.15 (2H, m), 7.26 (1H, d, J=8.8 Hz), 7.30-7.55 (7H, m), 7.70-7.80 (1H, m), 12.95 (1H, s).

REFERENCE EXAMPLE 24

6-(5-Methoxy-2-phenylindol-1-ylmethyl)pyridine-2-carbonitrile

To a solution of 5-methoxy-2-phenyl-1H-indole (200 mg) in N,N-dimethylformamide (5 mL) was added sodium hydride (dispersed in liquid paraffin, 50% or more, 45 mg) under ice-cooling. This mixture was stirred for 30 minutes at room temperature. Subsequently, 6-chloromethylpyridine-2-carbonitrile (216 mg) was added thereto, followed by stirring at 80° C. overnight. Water was added to the reaction mixture, followed by extraction with ethyl acetate. The organic layer was washed with water and saturated brine, dried over anhydrous magnesium sulfate, and then concentrated under reduced pressure. The residue was purified by silica gel column chromatography (eluting solvent: ethyl acetate-hexane) to obtain the title compound (228 mg). $^1$H-NMR (DMSO-d$_6$) δ ppm: 3.77 (3H, s), 5.55 (2H, s), 6.55-6.65 (1H, m), 6.77 (1H, dd, J=2.4, 8.8 Hz), 6.91 (1H, dd, J=1.5, 7.4 Hz), 7.13 (1H, d, J=2.4 Hz), 7.26 (1H, d, J=8.8 Hz), 7.35-7.55 (5H, m), 7.85-7.95 (2H, m).

REFERENCE EXAMPLE 25

5-(5-Methoxy-2-phenylindol-1-ylmethyl)furan-2-carbonitrile

In the same method as in Reference Example 24 using the corresponding starting material and reaction agents, the title compound was synthesized. $^1$H-NMR (CDCl$_3$) δ ppm: 3.87 (3H, s), 5.26 (2H, s), 6.00-6.05 (1H, m), 6.55 (1H, d, J=0.7 Hz), 6.89 (1H, dd, J=2.5, 8.8 Hz), 6.97 (1H, d, J=3.6 Hz), 7.12 (1H, d, J=2.5 Hz), 7.18 (1H, d, J=8.8 Hz), 7.35-7.55 (5H, m).

REFERENCE EXAMPLE 26

6-(6-Chloro-5-methoxy-2-phenylindol-1-ylmethyl)pyridine-2-carbonitrile

In the same method as in Reference Example 24 using the corresponding starting material and reaction agents, the title compound was synthesized. $^1$H-NMR (CDCl$_3$) δ ppm: 3.96 (3H, s), 5.44 (2H, s), 6.55-6.65 (1H, m), 6.70-6.80 (1H, m), 7.16 (1H, s), 7.18 (1H, s), 7.30-7.45 (5H, m), 7.50-7.75 (2H, m).

REFERENCE EXAMPLE 27

6-[6-Fluoro-5-methoxy-2-(thiophen-3-yl)indol-1-ylmethyl]pyridine-2-carboxamide

A mixture of methyl 6-[6-fluoro-5-methoxy-2-(thiophen-3-yl)indol-1-ylmethyl]pyridine-2-carboxylate (168 mg) and ammonia (about 7 mol/L methanol solution, 4.2 mL) was stirred at room temperature for 6 hours. The reaction mixture was diluted with tetrahydrofuran (4.2 mL), followed by stirring for 66 more hours. The reaction mixture was then concentrated under reduced pressure to obtain the title compound (166 mg). $^1$H-NMR (CDCl$_3$) δ ppm: 3.94 (3H, s), 5.45 (2H, s), 5.51 (1H, br s), 6.61 (1H, d, J=0.4 Hz), 6.90-7.00 (2H, m). 7.15 (1H, dd, J=1.3, 5.0 Hz), 7.18 (1H, d, J=8.3 Hz), 7.24 (1H, dd, J=1.3, 2.9 Hz), 7.39 (1H, dd, J=2.9, 5.0 Hz), 7.65 (1H, br s), 7.75 (1H, t. J=7.8 Hz), 8.09 (1H, d, J=7.8 Hz).

REFERENCE EXAMPLE 28

6-[6-Fluoro-5-methoxy-2-(thiophen-3-yl)indol-1-ylmethyl]pyridine-2-carbonitrile

To a solution of 6-[6-fluoro-5-methoxy-2-(thiophen-3-yl)indol-1-ylmethyl]pyridine-2-carboxamide (165 mg) in N,N-dimethylformamide (2.1 mL) was added phosphoryl chloride (0.058 mL) under ice-cooling. This mixture was stirred for 50 minutes. The reaction mixture was quenched with a saturated aqueous sodium hydrogen carbonate solution (10 mL). Ethyl acetate and water were then added to the mixture to separate the organic layer. The organic layer was washed with saturated brine, dried over anhydrous sodium sulfate, and then concentrated under reduced pressure. The residue was purified by silica gel column chromatography (eluting solvent: ethyl acetate-hexane) to obtain the title compound (67 mg). $^1$H-NMR (CDCl$_3$) δ ppm: 3.94 (3H, s), 5.47 (2H, s), 6.62 (1H, s), 6.80 (1H, d, J=8.3 Hz), 6.87 (1H, d, J=11.3 Hz), 7.10-7.30 (3H, m), 7.35-7.45 (1H, m), 7.59 (1H, d, J=7.7 Hz), 7.65-7.75 (1H, m).

REFERENCE EXAMPLE 29

6-(5-Methoxy-2-phenylindol-1-ylmethyl)pyridine-2-carboxamidoxime

To a suspension of hydroxylamine hydrochloride (233 mg) in dimethylsulfoxide (1.7 mL) was added sodium hydrogen carbonate (338 mg), and this mixture was stirred at 50° C. for 1 hour. Subsequently, 6-(5-methoxy-2-phenylindol-1-ylmethyl)pyridine-2-carbonitrile (114 mg) was added thereto, followed by stirring at 80° C. overnight. Water was added to the reaction mixture, followed by extraction with ethyl acetate. The organic layer was washed with water and saturated brine, dried over anhydrous magnesium sulfate, and then concentrated under reduced pressure to obtain the title compound (124 mg). $^1$H-NMR (DMSO-d$_6$) δ ppm: 3.76 (3H, s), 5.51 (2H, s), 5.65 (2H, br s), 6.59 (1H, s), 6.70-6.85 (2H, m), 7.11 (1H, d, J=2.4 Hz), 7.32 (1H, d, J=8.9 Hz), 7.35-7.70 (7H, m), 9.92 (1H, s).

EXAMPLE 1-1

N-(Methanesulfonyl)-6-(5-methoxy-2-phenylindol-1-ylmethyl)pyridine-2-carboxamide

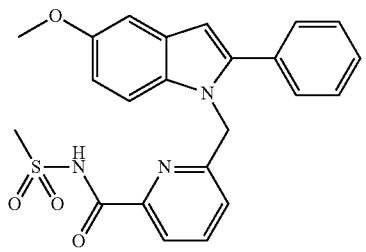 [SMILES: COc1ccc2c(c1)cc(-c1ccccc1)n2Cc1cccc(C(=O)NS(C)(=O)=O)n1]

Under an argon atmosphere, to a solution of 6-(5-methoxy-2-phenylindol-1-ylmethyl)pyridine-2-carboxylic acid (84 mg) in dichloromethane (2.3 mL) were added methanesulfonamide (22 mg), 1-ethyl-3-(3-dimethylaminopropyl)carbodiimide hydrochloride (45 mg), and 4-dimethylaminopyridine (29 mg). This mixture was stirred for 66 hours at room temperature. To the reaction mixture, 1 mol/L hydrochloric acid was added and stirred vigorously. The organic layer was separated, dried over anhydrous sodium sulfate, and then concentrated under reduced pressure. The residue was purified by silica gel column chromatography (eluting solvent: dichloromethane-methanol). The solvent was removed under reduced pressure. The residue was recrystallized from ethanol to obtain the title compound (16 mg). $^1$H-NMR (CDCl$_3$) δ ppm: 3.38 (3H, s), 3.87 (3H, s), 5.49 (2H, s), 6.64 (1H, d, J=0.5 Hz), 6.84 (1H, dd, J=2.4, 8.9 Hz), 6.90-6.95 (1H, m), 7.05 (1H, d, J=8.9 Hz), 7.16 (1H, d, J=2.4 Hz), 7.30-7.50 (5H, m), 7.76 (1H, t, J=7.8 Hz), 8.00-8.10 (1H, m), 10.01 (1H, br s).

EXAMPLES 1-2 to 1-14

In the same method as in Example 1-1 using the corresponding starting material and reaction agents, the groups of the compounds shown in Tables 1 to 3 were synthesized.

EXAMPLE 2-1

5-Methoxy-2-phenyl-1-[6-(1H-1,2,3,4-tetrazol-5-yl)pyridin-2-ylmethyl]-1H-indole

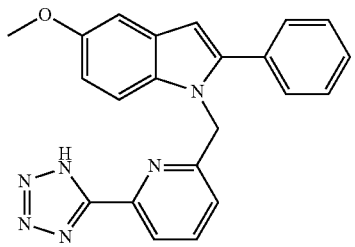 [SMILES: COc1ccc2c(c1)cc(-c1ccccc1)n2Cc1cccc(-c2nnn[nH]2)n1]

To a mixture of 6-(5-methoxy-2-phenylindol-1-ylmethyl)pyridine-2-carbonitrile (95 mg), isopropyl alcohol (6 mL), and water (4 mL) were added sodium azide (36 mg) and zinc bromide (32 mg). This mixture was stirred overnight while heated to reflux. The reaction mixture was left to cool to room temperature, and then diluted with ethyl acetate. To the mixture was added 2 mol/L hydrochloric acid (4 mL), followed by stirring at room temperature for 30 minutes. The organic layer was separated, and the aqueous layer was extracted with ethyl acetate. The combined organic layer was washed with saturated brine, dried over anhydrous magnesium sulfate, and then concentrated under reduced pressure. The residue was purified by silica gel column chromatography (eluting solvent: dichloromethane-methanol) to obtain the title compound (88 mg). $^1$H-NMR (DMSO-$d_6$) δ ppm: 3.78 (3H, s), 5.61 (2H, s), 6.54 (1H, d, J=7.8 Hz), 6.66 (1H, d, J=0.4 Hz), 6.78 (1H, dd, J=2.5, 8.9 Hz), 7.16 (1H, d, J=2.5 Hz), 7.29 (1H, d, J=8.9 Hz), 7.35-7.55 (5H, m), 7.90 (1H, t, J=7.8 Hz), 8.05 (1H, d, J=7.8 Hz). ESI-MS (m/z): 383 (M+H)$^+$

Examples 2-2 to 2-4

In the same method as in Example 2-1 using the corresponding starting material and reaction agents, the groups of the compounds shown in Table 4 were synthesized.

EXAMPLE 3

3-[6-(5-Methoxy-2-phenylindol-1-ylmethyl)pyridin-2-yl]-4,5-dihydro-1,2,4-oxadiazol-5-one

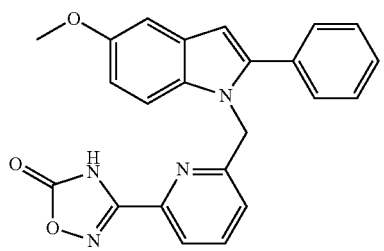 [SMILES: COc1ccc2c(c1)cc(-c1ccccc1)n2Cc1cccc(-c2noc(=O)[nH]2)n1]

To a solution of 6-(5-methoxy-2-phenylindol-1-ylmethyl)pyridine-2-carboxamidoxime (124 mg) in tetrahydrofuran (1.7 mL) were added 1,1'-carbonyldiimidazole (57 mg) and 1,8-diazabicyclo[5.4.0]undec-7-ene (53 μL). This mixture was stirred at room temperature for 2 hours. To the reaction mixture were added 1,1'-carbonyldiimidazole (27 mg) and 1,8-diazabicyclo[5.4.0]undec-7-ene (25 μL), followed by stirring at room temperature for 1 hour. To the reaction mixture was added 1 mol/L hydrochloric acid, followed by extraction with ethyl acetate. The organic layer was washed with water and saturated brine, dried over anhydrous magnesium sulfate, and then concentrated under reduced pressure. The residue was recrystallized from ethanol to obtain the title compound (116 mg). $^1$H-NMR (DMSO-$d_6$) δ ppm: 3.78 (3H, s), 5.55 (2H, s), 6.55-6.70 (2H, m), 6.77 (1H, dd, J=2.4, 8.9 Hz), 7.15 (1H, d, J=2.4 Hz), 7.26 (1H, d, J=8.9 Hz), 7.35-7.55 (5H, m), 7.75-7.90 (2H, m), 13.07 (1H, br s).

TABLE 1

| Ex. No. | Str | Physical Data |
|---|---|---|
| 1-2 | | $^1$H-NMR (DMSO-$d_6$) δ ppm: 3.22 (3H, s), 3.77 (3H, s), 5.41 (2H, s), 6.18 (1H, d, J = 3.6 Hz), 6.55 (1H, d, J = 0.5 Hz), 6.80 (1H, dd, J = 2.5, 8.9 Hz), 7.09 (1H, d, J = 2.5 Hz), 7.25-7.65 (7H, m), 12.03 (1H, br s). |
| 1-3 | | $^1$H-NMR (CDCl$_3$) δ ppm: 3.38 (3H, s), 3.96 (3H, s), 5.46 (2H, s), 6.64 (1H, d, J = 0.7 Hz), 6.90-7.00 (1H, m), 7.15-7.25 (2H, m), 7.35-7.50 (5H, m), 7.79 (1H, d, J = 7.8 Hz), 8.00-8.10 (1H, m), 9.92 (1H, br s). |

TABLE 1-continued

| Ex. No. | Str | Physical Data |
| --- | --- | --- |
| 1-4 | | $^1$H-NMR (DMSO-$d_6$) δ ppm: 3.86 (3H, s), 5.51 (2H, s), 6.66 (1H, s), 7.30-7.95 (15H, m), 11.50-11.80 (1H, br). |
| 1-5 | | $^1$H-NMR (DMSO-$d_6$) δ ppm: 3.40 (3H, s), 3.85 (3H, s), 5.68 (2H, s), 6.70-6.75 (1H, m), 6.80-6.90 (1H, m), 7.29 (1H, d, J = 8.5 Hz), 7.35 (1H, dd, J = 2.0, 4.3 Hz), 7.43 (1H, d, J = 11.9 Hz), 7.60-7.70 (2H, m), 7.85-7.95 (2H, m), 11.31 (1H, br s). |
| 1-6 | | $^1$H-NMR (DMSO-$d_6$) δ ppm: 1.23 (3H, t, J = 7.3 Hz), 3.50 (2H, q, J = 7.3 Hz), 3.86 (3H, s), 5.64 (2H, s), 6.67 (1H, d, J = 0.5 Hz), 6.85-6.95 (1H, m), 7.31 (1H, s), 7.35-7.60 (5H, m), 7.63 (1H, s), 7.80-7.95 (2H, m), 10.99 (1H, br s). |

TABLE 2

| Ex. No. | Strc | Physical Data |
| --- | --- | --- |
| 1-7 | | $^1$H-NMR (DMSO-$d_6$) δ ppm: 0.60-0.70 (2H, m), 0.85-0.95 (2H, m), 1.90-2.05 (1H, m), 3.38 (3H, s), 5.60 (2H, s), 6.62 (1H, s), 6.75-6.90 (2H, m), 7.26 (1H, d, J = 8.5 Hz), 7.33 (1H, d, J = 1.5 Hz), 7.35-7.60 (5H, m), 7.85-7.95 (2H, m), 11.30 (1H, br s). |
| 1-8 | | $^1$H-NMR (DMSO-$d_6$) δ ppm: 0.60-0.70 (2H, m), 0.85-0.95 (2H, m), 1.23 (3H, t, J = 7.4 Hz), 1.90-2.05 (1H, m), 3.50 (2H, q, J = 7.4 Hz), 5.61 (2H, s), 6.61 (1H, d, J = 0.5 Hz), 6.80-6.90 (2H, m), 7.28 (1H, d, J = 8.5 Hz), 7.32 (1H, d, J = 1.6 Hz), 7.35-7.60 (5H, m), 7.80-7.95 (2H, m), 11.15 (1H, br s). |

TABLE 2-continued

| Ex. No. | Strc | Physical Data |
| --- | --- | --- |
| 1-9 | 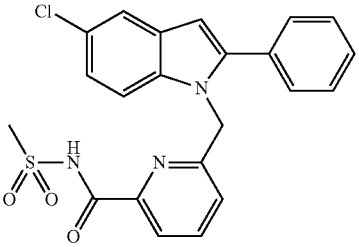 [SMILES: CS(=O)(=O)NC(=O)c1cccc(Cn2c(-c3ccccc3)cc3cc(Cl)ccc32)n1] | ¹H-NMR (DMSO-d$_6$) δ ppm:<br>3.38 (3H, s), 5.65 (2H, s), 6.71 (1H, s), 6.80-6.90 (1H, m), 7.14 (1H, dd, J = 2.1, 8.7 Hz), 7.40-7.60 (6H, m), 7.69 (1H, d, J = 2.1 Hz), 7.85-7.95 (2H, m), 11.24 (1H, br s). |
| 1-10 | 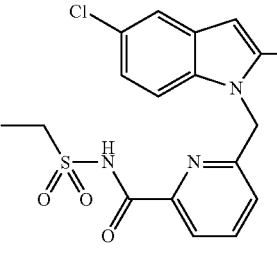 | ¹H-NMR (DMSO-d$_6$) δ ppm:<br>1.22 (3H, t, J = 7.3 Hz), 3.50 (2H, q, J = 7.3 Hz), 5.67 (2H, s), 6.71 (1H, s), 6.85-6.95 (1H, m), 7.13 (1H, dd, J = 2.1, 8.7 Hz), 7.40-7.60 (6H, m), 7.68 (1H, d, J = 2.1 Hz), 7.80-7.95 (2H, m), 11.06 (1H, br s). |
| 1-11 | 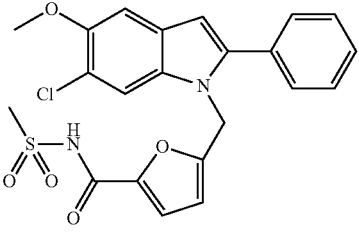 [SMILES: COc1cc2cc(-c3ccccc3)n(Cc3ccc(C(=O)NS(C)(=O)=O)o3)c2cc1Cl] | ¹H-NMR (DMSO-d$_6$) δ ppm:<br>3.24 (3H, s), 3.85 (3H, s), 5.45 (2H, s), 6.18 (1H, d, J = 3.5 Hz), 6.59 (1H, d, J = 0.5 Hz), 7.28 (1H, s), 7.30-7.65 (6H, m), 7.71 (1H, s), 12.05 (1H, br s). |

TABLE 3

| Ex. No. | Strc | Physical Data |
| --- | --- | --- |
| 1-12 | 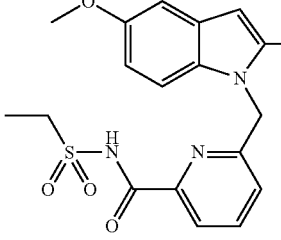 | ¹H-NMR (DMSO-d$_6$) δ ppm:<br>1.24 (3H, t, J = 7.4 Hz), 3.50 (2H, q, J = 7.4 Hz), 3.76 (3H, s), 5.61 (2H, s), 6.60-6.65 (1H, m), 6.75 (1H, dd, J = 2.5, 8.9 Hz), 6.87 (1H, dd, J = 1.2, 7.4 Hz), 7.13 (1H, d, J = 2.5 Hz), 7.31 (1H, d, J = 8.9 Hz), 7.35-7.60 (5H, m), 7.80-7.95 (2H, m), 11.06 (1 H, br s). |
| 1-13 | 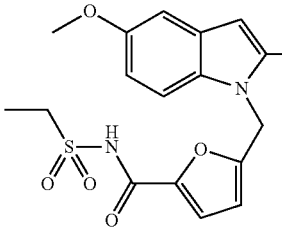 | ¹H-NMR (DMSO-d$_6$) δ ppm:<br>1.10 (3H, t, J = 7.4 Hz), 3.11 (2H, q, J = 7.4 Hz), 3.77 (3H, s), 5.34 (2H, s), 6.05 (1H, d, J = 3.3 Hz), 6.53 (1H, d, J = 0.5 Hz), 6.80 (1H, dd, J = 2.4, 8.9 Hz), 6.86 (1H, br s), 7.09 (1H, d, J = 2.4 Hz), 7.35-7.70 (6H, m).<br>ESI-MS (m/z): 439 (M + H)⁺ |

TABLE 3-continued

| Ex. No. | Strc | Physical Data |
|---|---|---|
| 1-14 | | ¹H-NMR (DMSO-d₆) δ ppm: 2.93 (3H, s), 3.76 (3H, s), 5.43 (2H, s), 6.55-6.65 (1H, m), 6.74 (1H, dd, J = 2.4, 8.9 Hz), 6.88 (1H, d, J = 7.6 Hz), 7.11 (1H, d, J = 2.4 Hz), 7.18 (1H, d, J = 8.9 Hz), 7.23 (1H, t, J = 7.6 Hz), 7.35-7.55 (5H, m), 7.60-7.80 (2H, m), 11.80-12.30 (1H, br). ESI-MS (m/z): 435 (M + H)⁺ |

TABLE 4

| Ex. No. | Strc | Physical Data |
|---|---|---|
| 2-2 | | ¹H-NMR (DMSO-d₆) δ ppm: 3.77 (3H, s), 5.47 (2H, s), 6.29 (1H, d, J = 3.6 Hz), 6.50-6.60 (1H, m), 6.82 (1H, dd, J = 2.5, 8.9 Hz), 7.05-7.15 (2H, m), 7.40-7.65 (6H, m). ESI-MS (m/z): 372 (M + H)⁺ |
| 2-3 | | ¹H-NMR (DMSO-d₆) δ ppm: 3.88 (3H, s), 5.63 (2H, s), 6.52 (1H, d, J = 7.9 Hz), 6.70 (1H, d, J = 0.4 Hz), 7.30-7.55 (6H, m), 7.61 (1H, s), 7.91 (1H, t, J = 7.9 Hz), 8.05 (1H, d, J = 7.9 Hz). ESI-MS (m/z): 417 (M + H)⁺ |
| 2-4 | | ¹H-NMR (DMSO-d₆) δ ppm: 3.86 (3H, s), 5.63 (2H, s), 6.52 (1H, d, J = 7.8 Hz), 6.72 (1H, s), 7.25-7.40 (2H, m), 7.44 (1H, d, J = 12.1 Hz), 7.60-7.75 (2H, m), 7.82 (1H, t, J = 7.8 Hz), 8.00 (1H, d, J = 7.8 Hz). ESI-MS (m/z): 407 (M + H)⁺ |

REFERENCE EXAMPLE 30 tert-Butyl (5-chloro-4-methoxy-2-methylphenyl)carbamate

A solution of 5-chloro-4-methoxy-2-methylaniline (2.19 g) and di-tert-butyl dicarbonate (3.06 g) in tetrahydrofuran (25.5 mL) was refluxed for 14 hours. The reaction mixture was left to cool to room temperature and concentrated under reduced pressure. The residue was purified by silica gel column chromatography (eluting solvent: ethyl acetate-hexane) to obtain the title compound (3.43 g). ¹H-NMR (CDCl₃) δ ppm: 1.51 (9H, s), 2.23 (3H, s), 3.86 (3H, s), 5.65-6.40 (1H, br), 6.72 (1H, s), 7.40-8.10 (1H, br).

REFERENCE EXAMPLE 31 tert-Butyl[5-chloro-2-(2-hydroxy-3-methylpentyl)-4-methoxyphenyl]carbamate

Under an argon atmosphere, to a solution of tert-butyl (5-chloro-4-methoxy-2-methylphenyl)carbamate (1.00 g) in tetrahydrofuran (18.4 mL) was added dropwise sec-butyl-lithium (1.08 mol/L hexane-cyclohexane solution, 7.5 mL) at −45° C., and the mixture was stirred for 30 minutes. Next, a solution of 2-methylbutyl aldehyde (0.430 mL) in tetrahydrofuran (1.84 mL) was added dropwise thereto, and the mixture was stirred at −45° C. for 35 minutes and then stirred at room temperature for 90 more minutes. To the reaction mixture was added saturated aqueous ammonium chloride solution/water (3/1, 40 mL), followed by extraction with ethyl acetate. The organic layer was washed with saturated brine, dried over anhydrous sodium sulfate, and then concentrated under reduced pressure. The residue was purified by silica gel column chromatography (eluting solvent: ethyl acetate-hexane) to obtain the title compound (876 mg). $^1$H-NMR (CDCl$_3$) δ ppm: 0.50-2.30 (19H, m), 2.45-2.95 (2H, m), 3.55-4.05 (4H, m), 6.60-6.80 (1H, m), 7.20-8.00 (2H, m).

REFERENCE EXAMPLE 32

1-(2-Amino-4-chloro-5-methoxyphenyl)-3-methylpentan-2-ol

To a solution of tert-butyl[5-chloro-2-(2-hydroxy-3-methylpentyl)-4-methoxyphenyl]carbamate (873 mg) in dichloromethane (12.2 mL) was added dropwise trifluoroacetic acid (3.76 mL) under ice-cooling, and this mixture was stirred for 9 hours. The reaction mixture was concentrated under reduced pressure. To the residue were added ethyl acetate and saturated aqueous sodium hydrogen carbonate solution to separate the organic layer. The organic layer was washed with saturated brine, dried over anhydrous sodium sulfate, and then concentrated under reduced pressure. The residue was purified by silica gel column chromatography (eluting solvent: ethyl acetate-hexane) to obtain the title compound (603 mg). $^1$H-NMR (CDCl$_3$) δ ppm: 0.75-1.75 (9H, m), 2.45-2.85 (2H, m), 3.30-4.10 (6H, m), 6.60-6.80 (2H, m). ESI-MS (m/z): 258, 260 (M+H)$^+$

REFERENCE EXAMPLE 33

2-(Butan-2-yl)-6-chloro-5-methoxy-1H-indole

A mixture of 1-(2-amino-4-chloro-5-methoxyphenyl)-3-methylpentan-2-ol (602 mg), tetrakis(triphenylphosphine)palladium(0) (135 mg), potassium carbonate (646 mg), 2-bromomesitylene (0.420 mL), and N,N-dimethylformamide (11.7 mL) was stirred at 160° C. for 1 hour under microwave irradiation. To the reaction mixture were added ethyl acetate and water to separate the organic layer. The organic layer was washed with saturated brine, dried over anhydrous sodium sulfate, and then concentrated under reduced pressure. The residue was purified by silica gel column chromatography (eluting solvent: ethyl acetate-hexane) to obtain the title compound (514 mg). $^1$H-NMR (CDCl$_3$) δ ppm: 0.91 (3H, t, J=7.4 Hz), 1.32 (3H, d, J=6.8 Hz), 1.55-1.80 (2H, m), 2.70-2.90 (1H, m), 3.91 (3H, s), 6.10-6.20 (1H, m), 7.05 (1H, s), 7.25-7.35 (1H, m), 7.50-8.00 (1H, br).

REFERENCE EXAMPLE 34

Methyl 6-[2-(butan-2-yl)-6-chloro-5-methoxyindol-1-ylmethyl]pyridine-2-carboxylate To a solution of 2-(butan-2-yl)-6-chloro-5-methoxy-1H-indole (289 mg) in N,N-dimethylformamide (6.1 mL) was added sodium hydride (dispersed in liquid paraffin, 55% or more, 73 mg) under ice-cooling. This mixture was stirred for 1 hour under ice-cooling. Subsequently, methyl 6-chloromethylpyridine-2-carboxylate (271 mg) was added thereto, followed by stirring at 80° C. for 21 hours. The reaction mixture was cooled to room temperature, and then saturated aqueous ammonium chloride solution/water (2/1, 30 mL) was added thereto, followed by extraction with ethyl acetate. The organic layer was washed with water and saturated brine successively, dried over anhydrous sodium sulfate, and then concentrated under reduced pressure. The residue was purified by silica gel column chromatography (eluting solvent: ethyl acetate-hexane) to obtain the title compound (328 mg). $^1$H-NMR (CDCl$_3$) δ ppm: 0.84 (3H, t, J=7.4 Hz), 1.23 (3H, d, J=6.9 Hz), 1.45-1.80 (2H, m), 2.60-2.75 (1H, m), 3.93 (3H, s), 4.06 (3H, s), 5.50 (2H, s), 6.31 (1H, s), 6.40-6.50 (1H, m), 7.12 (1H, s), 7.15 (1H, s), 7.64 (1H, t, J=7.9 Hz), 7.95-8.05 (1H, m).

REFERENCE EXAMPLE 35

6-[2-(Butan-2-yl)-6-chloro-5-methoxyindol-1-ylmethyl]pyridine-2-carboxylic acid

To a solution of methyl 6-[2-(butan-2-yl)-6-chloro-5-methoxyindol-1-ylmethyl]pyridine-2-carboxylate (200 mg) in tetrahydrofuran (3.08 mL) and methanol (1.32 mL) was added 2 mol/L aqueous sodium hydroxide solution (0.775 mL) at room temperature, followed by stirring for 2.5 hours. To the reaction mixture was added 1 mol/L hydrochloric acid (1.55 mL). To the mixture were added water and ethyl acetate to separate the organic layer. The organic layer was washed with water twice, dried over anhydrous sodium sulfate, and then concentrated under reduced pressure to obtain the title compound (190 mg). $^1$H-NMR (DMSO-d$_6$) δ ppm: 0.77 (3H, t, J=7.4 Hz), 1.17 (3H, d, J=6.9 Hz), 1.40-1.70 (2H, m), 2.80-2.95 (1H, m), 3.83 (3H, s), 5.45-5.65 (2H, m), 6.30 (1H, s), 6.70 (1H, d, J=7.3 Hz), 7.20 (1H, s), 7.55 (1H, s), 7.80-7.95 (2H, m), 13.00-13.50 (1H, br).

REFERENCE EXAMPLE 36

Methyl 6-[2-(2,5-difluorophenyl)-5-methoxyindol-1-ylmethyl]pyridine-2-carboxylate In the same method as in Reference Example 34 using the corresponding starting material and reaction agents, the title compound was synthesized. $^1$H-NMR (CDCl$_3$) δ ppm: 3.86 (3H, s), 4.02 (3H, s), 5.47 (2H, s), 6.55-6.70 (2H, m), 6.80-6.90 (1H, m), 6.95-7.20 (5H, m), 7.64 (1H, t, J=7.8 Hz), 7.97 (1H, d, J=7.8 Hz).

REFERENCE EXAMPLE 37

6-[2-(2,5-Difluorophenyl)-5-methoxyindol-1-ylmethyl]pyridine-2-carboxylic acid

In the same method as in Reference Example 35 using the corresponding starting material and reaction agents, the title compound was synthesized. $^1$H-NMR (DMSO-d$_6$) δ ppm: 3.77 (3H, s), 5.43 (2H, s), 6.66 (1H, s), 6.75-6.90 (2H, m), 7.14 (1H, d, J=2.5 Hz), 7.25-7.70 (4H, m), 7.75-7.95 (2H, m). ESI-MS (m/z): 395 (M+H)$^+$

REFERENCE EXAMPLE 38 tert-Butyl {5-chloro-4-methoxy-2-[2-oxo-2-(pyridin-3-yl)ethyl]phenyl}carbamate

In the same method as in Reference Example 14 using the corresponding starting material and reaction agents, the title compound was synthesized. $^1$H-NMR (CDCl$_3$) δ ppm: 1.47 (9H, s), 3.85 (3H, s), 4.29 (2H, s), 6.50-7.20 (2H, m), 7.40-7.90 (2H, m), 8.25-8.35 (1H, m), 8.75-8.90 (1H, m), 9.25-9.35 (1H, m).

REFERENCE EXAMPLE 39

6-Chloro-5-methoxy-2-(pyridin-3-yl)-1H-indole

In the same method as in Reference Example 15 using the corresponding starting material and reaction agents, the title compound was synthesized. $^1$H-NMR (CDCl$_3$) δ ppm: 3.95 (3H, s), 6.75-6.85 (1H, m), 7.14 (1H, s), 7.38 (1H, dd, J=4.8, 8.0 Hz), 7.45 (1H, s), 7.85-8.00 (1H, m), 8.36 (1H, br s), 8.50-8.65 (1H, m), 8.90-9.00 (1H, m).

REFERENCE EXAMPLE 40

Methyl 6-[6-chloro-5-methoxy-2-(pyridin-3-yl)indol-1-ylmethyl]pyridine-2-carboxylate In the same method as in Reference Example 34 using the corresponding starting material and reaction agents, the title compound was synthesized. $^1$H-NMR (CDCl$_3$) δ ppm: 3.96 (3H, s), 4.03 (3H, s), 5.50 (2H, s), 6.60-6.80 (2H, m), 7.20 (1H, s), 7.23 (1H, s), 7.25-7.40 (1H, m), 7.65-7.80 (2H, m), 8.02 (1H, d, J=7.8 Hz), 8.55-8.65 (1H, m), 8.65-8.75 (1H, m).

REFERENCE EXAMPLE 41

6-[6-Chloro-5-methoxy-2-(pyridin-3-yl)indol-1-ylmethyl]pyridine-2-carboxylic acid In the same method as in Reference Example 35 using the corresponding starting material and reaction agents, the title compound was synthesized. $^1$H-NMR (DMSO-d$_6$) δ ppm: 3.87 (3H, s), 5.55 (2H, s), 6.75 (1H, s), 6.85-7.00 (1H, m), 7.33 (1H, s), 7.35-7.55 (1H, m), 7.63 (1H, s), 7.80-7.95 (2H, m), 8.00-8.15 (1H, m), 8.50-8.65 (1H, m), 8.70-8.85 (1H, m), 12.80-13.60 (1H, br).

REFERENCE EXAMPLE 42 tert-Butyl[2-(2-hydroxy-3-methylpentyl)-4-methoxyphenyl]carbamate

In the same method as in Reference Example 31 using the corresponding starting material and reaction agents, the title compound was synthesized. $^1$H-NMR (CDCl$_3$) δ ppm: 0.85-1.05 (6H, m), 1.15-1.35 (1H, m), 1.40-1.70 (11H, m), 1.80-2.05 (1H, m), 2.50-2.85 (2H, m), 3.60-3.85 (4H, m), 6.65-6.85 (2H, m), 7.25-7.65 (2H, m).

REFERENCE EXAMPLE 43

2-(Butan-2-yl)-5-methoxy-1H-indole

To a solution of tert-butyl[2-(2-hydroxy-3-methylpentyl)-4-methoxyphenyl]carbamate (2.65 g) in dichloromethane (25 mL) was added trifluoroacetic acid (5 mL) under ice-cooling. This mixture was stirred at room temperature for 2 hours. The reaction mixture was concentrated under reduced pressure. To the residue were added ethyl acetate and saturated aqueous sodium hydrogen carbonate solution to separate the organic layer. The organic layer was washed with water and saturated brine successively, dried over anhydrous sodium sulfate, and then concentrated under reduced pressure. Under an argon atmosphere, the residue was dissolved in N,N-dimethylformamide (30 mL), and then 2-bromomesitylene (1.50 mL), tetrakis(triphenylphosphine) palladium(0) (472 mg), and potassium carbonate (2.25 g) were added thereto. The mixture was stirred overnight at 150° C. The reaction mixture was cooled to room temperature, and then water was added thereto, followed by extraction with ethyl acetate. The organic layer was washed with water and saturated brine successively, dried over anhydrous magnesium sulfate, and then concentrated under reduced pressure. The residue was purified by silica gel column chromatography (eluting solvent: ethyl acetate-hexane) to obtain the title compound (1.46 g). $^1$H-NMR (CDCl$_3$) δ ppm: 0.91 (3H, t, J=7.4 Hz), 1.32 (3H, d, J=7.0 Hz), 1.55-1.80 (2H, m), 2.75-2.90 (1H, m), 3.84 (3H, s), 6.15-6.20 (1H, m), 6.77 (1H, dd, J=2.4, 8.8 Hz), 7.02 (1H, d, J=2.4 Hz), 7.19 (1H, d, J=8.8 Hz), 7.77 (1H, br s).

REFERENCE EXAMPLE 44

Methyl 6-[2-(butan-2-yl)-5-methoxyindol-1-ylmethyl]pyridine-2-carboxylate

In the same method as in Reference Example 1 using the corresponding starting material and reaction agents, the title compound was synthesized. $^1$H-NMR (CDCl$_3$) δ ppm: 0.85 (3H, t, J=7.4 Hz), 1.23 (3H, d, J=6.8 Hz), 1.45-1.80 (2H, m), 2.60-2.80 (1H, m), 3.84 (3H, s), 4.05 (3H, s), 5.54 (2H, s), 6.32 (1H, s), 6.40-6.50 (1H, m), 6.75 (1H, dd, J=2.3, 8.8 Hz), 7.00 (1H, d, J=8.8 Hz), 7.08 (1H, d, J=2.3 Hz), 7.61 (1H, t, J=7.8 Hz), 7.95-8.05 (1H, m).

REFERENCE EXAMPLE 45

6-[2-(Butan-2-yl)-5-methoxyindol-1-ylmethyl]pyridine-2-carboxylic acid

In the same method as in Reference Example 2 using the corresponding starting material and reaction agents, the title compound was synthesized. $^1$H-NMR (DMSO-d$_6$) δ ppm: 0.79 (3H, t, J=7.4 Hz), 1.18 (3H, d, J=6.8 Hz), 1.40-1.75 (2H, m), 2.80-2.95 (1H, m), 3.73 (3H, s), 5.45-5.60 (2H, m), 6.25 (1H, s), 6.55-6.75 (2H, m), 7.01 (1H, d, J=2.5 Hz), 7.23 (1H, d, J=9.0 Hz), 7.75-7.95 (2H, m), 12.50-14.00 (1H, br).

REFERENCE EXAMPLE 46

6-Fluoro-5-methoxy-2-phenyl-1H-indole

In the same method as in Reference Example 6 using the corresponding starting material and reaction agents, the title compound was synthesized. $^1$H-NMR (CDCl$_3$) δ ppm: 3.94 (3H, s), 6.70-6.80 (1H, m), 7.10-7.20 (2H, m), 7.25-7.50 (3H, m), 7.55-7.70 (2H, m), 8.23 (1H, br s).

REFERENCE EXAMPLE 47

Methyl 6-(6-fluoro-5-methoxy-2-phenylindol-1-ylmethyl)pyridine-2-carboxylate

In the same method as in Reference Example 1 using the corresponding starting material and reaction agents, the title compound was synthesized. $^1$H-NMR (CDCl$_3$) δ ppm: 3.94 (3H, s), 4.03 (3H, s), 5.53 (2H, s), 6.55-6.75 (2H, m), 6.80-6.95 (1H, m), 7.20 (1H, d, J=8.3 Hz), 7.30-7.45 (5H, m), 7.68 (1H, t, J=7.8 Hz), 7.95-8.05 (1H, m).

REFERENCE EXAMPLE 48

6-(6-Fluoro-5-methoxy-2-phenylindol-1-ylmethyl)pyridine-2-carboxylic acid

In the same method as in Reference Example 35 using the corresponding starting material and reaction agents, the title compound was synthesized. $^1$H-NMR (DMSO-d$_6$) δ ppm: 3.85 (3H, s), 5.52 (2H, s), 6.60-6.80 (2H, m), 7.25-7.65 (7H, m), 7.75-7.95 (2H, m), 11.90-14.50 (1H, br).

REFERENCE EXAMPLE 49 tert-Butyl {5-chloro-2-[2-(furan-3-yl)-2-oxoethyl]-4-methoxyphenyl}carbamate

In the same method as in Reference Example 14 using the corresponding starting material and reaction agents, the title compound was synthesized. $^1$H-NMR (CDCl$_3$) δ ppm: 1.50 (9H, s), 3.85 (3H, s), 4.01 (2H, s), 6.70 (1H, s), 6.75-6.85 (1H, m), 7.00-8.00 (3H, m), 8.15-8.25 (1H, m).

REFERENCE EXAMPLE 50

6-Chloro-2-(furan-3-yl)-5-methoxy-1H-indole

In the same method as in Reference Example 15 using the corresponding starting material and reaction agents, the title compound was synthesized. $^1$H-NMR (CDCl$_3$) δ ppm: 3.94 (3H, s), 6.50-6.60 (1H, m), 6.60-6.75 (1H, m), 7.09 (1H, s), 7.35-7.40 (1H, m), 7.45-7.55 (1H, m), 7.70-7.80 (1H, m), 7.80-8.20 (1H, br).

REFERENCE EXAMPLE 51

Methyl 6-[6-chloro-2-(furan-3-yl)-5-methoxyindol-1-ylmethyl]pyridine-2-carboxylate In the same method as in Reference Example 1 using the corresponding starting material and reaction agents, the title compound was synthesized. $^1$H-NMR (CDCl$_3$) δ ppm: 3.95 (3H, s), 4.06 (3H, s), 5.58 (2H, s), 6.45-6.55 (1H, m), 6.55-6.75 (2H, m), 7.16 (1H, s), 7.20-7.25 (1H, m), 7.40-7.55 (2H, m), 7.69 (1H, t, J=7.8 Hz), 8.00-8.10 (1H, m).

REFERENCE EXAMPLE 52

6-[6-Chloro-2-(furan-3-yl)-5-methoxyindol-1-ylmethyl]pyridine-2-carboxylic acid

In the same method as in Reference Example 35 using the corresponding starting material and reaction agents, the title compound was synthesized. $^1$H-NMR (DMSO-d$_6$) δ ppm: 3.86 (3H, s), 5.63 (2H, s), 6.65-6.90 (3H, m), 7.27 (1H, s), 7.60-8.10 (5H, m). ESI-MS (m/z): 383, 385(M+H)$^+$

REFERENCE EXAMPLE 53 tert-Butyl {4-methoxy-2-[2-(1-methylcyclopropyl)-2-oxoethyl]phenyl}carbamate

In the same method as in Reference Example 14 using the corresponding starting material and reaction agents, the title compound was synthesized. $^1$H-NMR (CDCl$_3$) δ ppm: 0.75-0.95 (2H, m), 1.25-1.45 (5H, m), 1.50 (9H, s), 3.62 (2H, s), 3.77 (3H, s), 6.63 (1H, d, J=3.0 Hz), 6.79 (1H, dd, J=3.0, 8.8 Hz), 7.20-7.75 (2H, m).

REFERENCE EXAMPLE 54

5-Methoxy-2-(1-methylcyclopropyl)-1H-indole

In the same method as in Reference Example 15 using the corresponding starting material and reaction agents, the title compound was synthesized. $^1$H-NMR (CDCl$_3$) δ ppm: 0.70-1.05 (4H, m), 1.49 (3H, s), 3.83 (3H, s), 6.10-6.20 (1H, m), 6.76 (1H, dd, J=2.4, 8.8 Hz), 6.98 (1H, d, J=2.4 Hz), 7.16 (1H, d, J=8.8 Hz), 7.55-7.90 (1H, br).

REFERENCE EXAMPLE 55

Methyl 6-[5-methoxy-2-(1-methylcyclopropyl)indol-1-ylmethyl]pyridine-2-carboxylate In the same method as in Reference Example 1 using the corresponding starting material and reaction agents, the title compound was synthesized. $^1$H-NMR (CDCl$_3$) δ ppm: 0.60-0.95 (4H, m), 1.26 (3H, s), 3.83 (3H, s), 4.06 (3H, s), 5.74 (2H, s), 6.30-6.35 (1H, m), 6.40-6.50 (1H, m), 6.72 (1H, dd, J=2.4, 8.9 Hz), 6.85 (1H, d, J=8.9 Hz), 7.06 (1H, d, J=2.4 Hz), 7.62 (1H, t, J=7.9 Hz), 7.95-8.05 (1H, m).

REFERENCE EXAMPLE 56

6-[5-Methoxy-2-(1-methylcyclopropyl)indol-1-ylmethyl]pyridine-2-carboxylic acid

In the same method as in Reference Example 35 using the corresponding starting material and reaction agents, the title compound was synthesized. $^1$H-NMR (DMSO-d$_6$) δ ppm: 0.60-0.90 (4H, m), 1.25 (3H, s), 3.72 (3H, s), 5.64 (2H, s), 6.25-6.30 (1H, m), 6.45-6.60 (1H, m), 6.65 (1H, dd, J=2.5, 8.8 Hz), 6.95-7.10 (2H, m), 7.75-7.95 (2H, m), 12.70-13.90 (1H, br).

REFERENCE EXAMPLE 57 tert-Butyl {5-chloro-4-methoxy-2-[2-(1-methylcyclopropyl)-2-oxoethyl]phenyl}carbamate In the same method as in Reference Example 14 using the corresponding starting material and reaction agents, the title compound was synthesized. $^1$H-NMR (CDCl$_3$) δ ppm: 0.80-0.95 (2H, m), 1.30-1.45 (5H, m), 1.50 (9H, s), 3.64 (2H, s), 3.86 (3H, s), 6.63 (1H, s), 7.20-7.85 (2H, m).

REFERENCE EXAMPLE 58

6-Chloro-5-methoxy-2-(1-methylcyclopropyl)-1H-indole

In the same method as in Reference Example 15 using the corresponding starting material and reaction agents, the title compound was synthesized. $^1$H-NMR (CDCl$_3$) δ ppm: 0.70-1.05 (4H, m), 1.48 (3H, s), 3.91 (3H, s), 6.05-6.15 (1H, m), 7.02 (1H, s), 7.25-7.35 (1H, m), 7.55-7.90 (1H, br).

REFERENCE EXAMPLE 59

Methyl 6-[6-chloro-5-methoxy-2-(1-methylcyclopropyl)indol-1-ylmethyl]pyridine-2-carboxylate In the same method as in Reference Example 1 using the corresponding starting material and reaction agents, the title compound was synthesized. $^1$H-NMR (CDCl$_3$) δ ppm: 0.60-0.95 (4H, m), 1.25 (3H, s), 3.91 (3H, s), 4.07 (3H, s), 5.70 (2H, s), 6.25-6.35 (1H, m), 6.40-6.50 (1H, m), 7.00 (1H, s), 7.09 (1H, s), 7.65 (1H, t, J=7.8 Hz), 7.95-8.10 (1H, m).

REFERENCE EXAMPLE 60

6-[6-Chloro-5-methoxy-2-(1-methylcyclopropyl)indol-1-ylmethyl]pyridine-2-carboxylic acid In the same method as in Reference Example 35 using the corresponding starting material and reaction agents, the title compound was synthesized. $^1$H-NMR (DMSO-d$_6$) δ ppm: 0.60-0.90 (4H, m), 1.23 (3H, s), 3.82 (3H, s), 5.66 (2H, s), 6.25-6.35 (1H, m), 6.55-6.65 (1H, m), 7.20 (1H, s), 7.32 (1H, s), 7.75-7.95 (2H, m), 13.00-13.60 (1H, br).

REFERENCE EXAMPLE 61

Ethyl 5-[5-methoxy-2-(1-methylcyclopryopyl)indol-1-ylmethyl]furan-2-carboxylate

To a solution of 5-methoxy-2-(1-methylcyclopryopyl)-1H-indole (280 mg) in N,N-dimethylformamide (5.6 mL) was added sodium hydride (dispersed in liquid paraffin, 50% or more, 70 mg) under ice-cooling. This mixture was stirred at room temperature for 40 minutes. Subsequently, ethyl 5-chloromethylfuran-2-carboxylate (0.254 mL) was added thereto, and the mixture was stirred at 80° C. for 14 hours. To the reaction mixture were added saturated aqueous ammonium chloride solution and water, followed by extraction with ethyl acetate. The organic layer was washed with water and saturated brine successively, dried over anhydrous magnesium sulfate, and then concentrated under reduced pressure. The residue was purified by aminopropylated silica gel column chromatography (eluting solvent: ethyl acetate-hexane) to obtain the title compound (92 mg). $^1$H-NMR (CDCl$_3$) δ ppm: 0.65-1.00 (4H, m), 1.30-1.45 (6H, m), 3.82 (3H, s), 4.35 (2H, q, J=7.2 Hz), 5.49 (2H, s), 5.80-5.90 (1H, m), 6.20-6.30 (1H, m), 6.78 (1H, dd, J=2.4, 8.9 Hz), 6.95-7.10 (3H, m).

REFERENCE EXAMPLE 62

5-[5-Methoxy-2-(1-methylcyclopryopyl)indol-1-ylmethyl]furan-2-carboxylic acid

To a solution of ethyl 5-[5-methoxy-2-(1-methylcyclopryopyl)indol-1-ylmethyl]furan-2-carboxylate (90 mg) in tetrahydrofuran (1.3 mL) and methanol (1.3 mL) was added 2 mol/L aqueous sodium hydroxide solution (0.38 mL) at room temperature, followed by stirring at 60° C. for 1.5 hours. The reaction mixture was concentrated under reduced pressure. The residue was diluted with water, and then 2 mol/L hydrochloric acid (0.38 mL) was added. To the mixture was added ethyl acetate to separate the organic layer. The organic layer was dried over anhydrous magnesium sulfate and then concentrated under reduced pressure to obtain the title compound (76 mg). $^1$H-NMR (DMSO-d$_6$) δ ppm: 0.70-1.00 (4H, m), 1.36 (3H, s), 3.71 (3H, s), 5.52 (2H, s), 6.15-6.25 (1H, m), 6.36 (1H, d, J=3.5 Hz), 6.69 (1H, dd, J=2.5, 8.9 Hz), 6.96 (1H, d, J=2.5 Hz), 7.11 (1H, d, J=3.5 Hz), 7.26 (1H, d, J=8.9 Hz), 12.80-13.30 (1H, br).

REFERENCE EXAMPLE 63

Ethyl 5-[6-chloro-5-methoxy-2-(1-methylcyclopryopyl)indol-1-ylmethyl]furan-2-carboxylate In the same method as in Reference Example 61 using the corresponding starting material and reaction agents, the title compound was synthesized. $^1$H-NMR (CDCl$_3$) δ ppm: 0.65-1.00 (4H, m), 1.25-1.45 (6H, m), 3.90 (3H, s), 4.36 (2H, q, J=7.1 Hz), 5.46 (2H, s), 5.80-5.95 (1H, m), 6.20-6.30 (1H, m), 6.95-7.10 (2H, m), 7.15-7.25 (1H, m).

REFERENCE EXAMPLE 64

5-[6-Chloro-5-methoxy-2-(1-methylcyclopryopyl)indol-1-ylmethyl]furan-2-carboxylic acid In the same method as in Reference Example 62 using the corresponding starting material and reaction agents, the title compound was synthesized. $^1$H-NMR (DMSO-d$_6$) δ ppm: 0.70-1.00 (4H, m), 1.35 (3H, s), 3.80 (3H, s), 5.54 (2H, s), 6.20-6.30 (1H, m), 6.35 (1H, d, J=3.4 Hz), 7.00-7.20 (2H, m), 7.51 (1H, s). ESI-MS (m/z): 360 (M+H)$^+$

REFERENCE EXAMPLE 65

6-[2-(Butan-2-yl)-6-chloro-5-methoxyindol-1-ylmethyl]pyridine-2-carboxamide

To a suspension of methyl 6-[2-(butan-2-yl)-6-chloro-5-methoxyindol-1-ylmethyl]pyridine-2-carboxylate (125 mg) in ammonia (Ca. 7 mol/L methanol solution, 20.1 mL) was added tetrahydrofuran (6.7 mL) at room temperature, followed by stirring for 27 hours. The reaction mixture was concentrated under reduced pressure to obtain the title compound (120 mg). $^1$H-NMR (CDCl$_3$) δ ppm: 0.86 (3H, t, J=7.5 Hz), 1.25 (3H, d, J=6.9 Hz), 1.45-1.80 (2H, m), 2.65-2.80 (1H, m), 3.93 (3H, s), 5.39 (2H, s), 5.45-5.65 (1H, br), 6.30 (1H, s), 6.65-6.75 (1H, m), 7.11 (1H, s), 7.19 (1H, s), 7.60-7.80 (2H, m), 8.00-8.15 (1H, m).

REFERENCE EXAMPLE 66

6-[2-(Butan-2-yl)-6-chloro-5-methoxyindol-1-ylmethyl]pyridine-2-carbonitrile

To a solution of 6-[2-(butan-2-yl)-6-chloro-5-methoxyindol-1-ylmethyl]pyridine-2-carboxamide (118 mg) in dichloromethane (1.6 mL) were successively added triethylamine (0.225 mL) and trifluoroacetic anhydride (0.112 mL) under ice-cooling. This mixture was stirred at room temperature for 22 hours. To the reaction mixture was added saturated aqueous sodium hydrogen carbonate solution, followed by extraction with ethyl acetate. The organic layer was washed with saturated brine, dried over anhydrous sodium sulfate, and then concentrated under reduced pressure. The residue was purified by silica gel column chromatography (eluting solvent: ethyl acetate-hexane) to obtain the title compound (98 mg). $^1$H-NMR (CDCl$_3$) δ ppm: 0.86 (3H, t, J=7.4 Hz), 1.24 (3H, d, J=6.8 Hz), 1.45-1.80 (2H, m), 2.60-2.75 (1H, m), 3.93 (3H, s), 5.40 (2H, s), 6.31 (1H, s), 6.50-6.65 (1H, m), 7.11 (1H, s), 7.14 (1H, s), 7.50-7.70 (2H, m).

REFERENCE EXAMPLE 67

6-[2-(2,5-Difluorophenyl)-5-methoxyindol-1-ylmethyl]pyridine-2-carboxamide

In the same method as in Reference Example 65 using the corresponding starting material and reaction agents, the title compound was synthesized. $^1$H-NMR (CDCl$_3$) δ ppm: 3.86 (3H, s), 5.37 (2H, s), 5.40-5.60 (1H, br), 6.64 (1H, s), 6.75-6.90 (2H, m), 7.00-7.20 (5H, m), 7.50-7.75 (2H, m), 7.95-8.10 (1H, m).

REFERENCE EXAMPLE 68

6-[2-(2,5-Difluorophenyl)-5-methoxyindol-1-ylmethyl]pyridine-2-carbonitrile

In the same method as in Reference Example 66 using the corresponding starting material and reaction agents, the title compound was synthesized. $^1$H-NMR (CDCl$_3$) δ ppm: 3.86 (3H, s), 5.37 (2H, s), 6.64 (1H, s), 6.72 (1H, d, J=8.0 Hz), 6.86 (1H, dd, J=2.4, 8.9 Hz), 7.02 (1H, d, J=8.9 Hz), 7.05-7.20 (4H, m), 7.53 (1H, d, J=8.0 Hz), 7.63 (1H, t, J=8.0 Hz).

REFERENCE EXAMPLE 69

6-[2-(Butan-2-yl)-5-methoxyindol-1-ylmethyl]pyridine-2-carbonitrile

In the same method as in Reference Example 24 using the corresponding starting material and reaction agents, the title compound was synthesized. $^1$H-NMR (CDCl$_3$) δ ppm: 0.87 (3H, t, J=7.4 Hz), 1.24 (3H, d, J=7.0 Hz), 1.50-1.80 (2H, m), 2.60-2.80 (1H, m), 3.84 (3H, s), 5.44 (2H, s), 6.30-6.35 (1H, m), 6.50-6.60 (1H, m), 6.76 (1H, dd, J=2.5, 8.8 Hz), 7.00 (1H, d, J=8.8 Hz), 7.08 (1H, d, J=2.5 Hz), 7.50-7.70 (2H, m).

REFERENCE EXAMPLE 70

5-(6-Chloro-5-methoxy-2-phenylindol-1-ylmethyl)furan-2-carboxamide

A suspension of ethyl 5-(6-chloro-5-methoxy-2-phenylindol-1-ylmethyl)furan-2-carboxylate (258 mg) in ammonia (Ca. 7 mol/L methanol solution, 12.4 mL) was stirred at room temperature for 44 hours. The reaction mixture was filtered, washed with methanol, and then concentrated under reduced pressure to obtain the title compound (138 mg). $^1$H-NMR (CDCl$_3$) δ ppm: 3.95 (3H, s), 5.23 (2H, s), 6.10 (1H, d, J=3.5 Hz), 6.50-6.55 (1H, m), 7.03 (1H, d, J=3.5 Hz), 7.15 (1H, s), 7.35-7.55 (6H, m).

REFERENCE EXAMPLE 71

5-(6-Chloro-5-methoxy-2-phenylindol-1-ylmethyl)furan-2-carbonitrile

To a solution of 5-(6-chloro-5-methoxy-2-phenylindol-1-ylmethyl)furan-2-carboxamide (194 mg) in dichloromethane (2.5 mL) were successively added triethylamine (0.355 mL) and trifluoroacetic anhydride (0.177 mL) under ice-cooling. This mixture was stirred at room temperature for 8 hours. To the reaction mixture was added saturated aqueous sodium hydrogen carbonate solution, followed by extraction with ethyl acetate. The organic layer was washed with saturated brine, dried over anhydrous sodium sulfate, and then concentrated under reduced pressure. The residue was purified by silica gel column chromatography (eluting solvent: ethyl acetate-hexane) to obtain the title compound (143 mg). $^1$H-NMR (CDCl$_3$) δ ppm: 3.95 (3H, s), 5.23 (2H, s), 6.00-6.10 (1H, m), 6.50-6.60 (1H, m), 6.98 (1H, d, J=3.6 Hz), 7.16 (1H, s), 7.25-7.35 (1H, m), 7.40-7.55 (5H, m).

REFERENCE EXAMPLE 72

6-(6-Fluoro-5-methoxy-2-phenylindol-1-ylmethyl)pyridine-2-carboxamide

In the same method as in Reference Example 65 using the corresponding starting material and reaction agents, the title compound was synthesized. $^1$H-NMR (CDCl$_3$) δ ppm: 3.94 (3H, s), 5.35-5.55 (3H, m), 6.55-6.65 (1H, m), 6.85-7.00 (2H, m), 7.19 (1H, d, J=8.3 Hz), 7.30-7.45 (5H, m), 7.50-7.70 (1H, br), 7.73 (1H, t, J=7.8 Hz), 8.00-8.10 (1H, m).

REFERENCE EXAMPLE 73

6-(6-Fluoro-5-methoxy-2-phenylindol-1-ylmethyl)pyridine-2-carbonitrile

In the same method as in Reference Example 66 using the corresponding starting material and reaction agents, the title compound was synthesized. $^1$H-NMR (CDCl$_3$) δ ppm: 3.94 (3H, s), 5.43 (2H, s), 6.55-6.65 (1H, m), 6.70-6.90 (2H, m), 7.20 (1H, d, J=8.2 Hz), 7.30-7.75 (7H, m).

REFERENCE EXAMPLE 74

6-[6-Chloro-2-(furan-3-yl)-5-methoxyindol-1-ylmethyl]pyridine-2-carbonitrile

In the same method as in Reference Example 24 using the corresponding starting material and reaction agents, the title compound was synthesized. $^1$H-NMR (CDCl$_3$) δ ppm: 3.95 (3H, s), 5.48 (2H, s), 6.45-6.50 (1H, m), 6.55-6.65 (1H, m), 6.70-6.85 (1H, m), 7.15 (1H, s), 7.15-7.25 (1H, m), 7.45-7.65 (3H, m), 7.69 (1H, t, J=7.9 Hz).

REFERENCE EXAMPLE 75

6-[5-Methoxy-2-(1-methylcyclopropyl)indol-1-ylmethyl]pyridine-2-carbonitrile

In the same method as in Reference Example 24 using the corresponding starting material and reaction agents, the title compound was synthesized. $^1$H-NMR (CDCl$_3$) δ ppm: 0.65-0.90 (4H, m), 1.27 (3H, s), 3.83 (3H, s), 5.64 (2H, s), 6.25-6.35 (1H, m), 6.50-6.60 (1H, m), 6.74 (1H, dd, J=2.4, 8.8 Hz), 6.85 (1H, d, J=8.8 Hz), 7.05 (1H, d, J=2.4 Hz), 7.50-7.70 (2H, m).

REFERENCE EXAMPLE 76

6-[6-Chloro-5-methoxy-2-(1-methylcyclopropyl)indol-1-ylmethyl]pyridine-2-carbonitrile In the same method as in Reference Example 24 using the corresponding starting material and reaction agents, the title compound was synthesized. $^1$H-NMR (CDCl$_3$) δ ppm: 0.65-0.90 (4H, m), 1.26 (3H, s), 3.92 (3H, s), 5.60 (2H, s), 6.25-6.35 (1H, m), 6.50-6.60 (1H, m), 6.99 (1H, s), 7.09 (1H, s), 7.55-7.70 (2H, m).

REFERENCE EXAMPLE 77

5-[5-Methoxy-2-(1-methylcyclopropyl)indol-1-ylmethyl]furan-2-carbonitrile

To a solution of 5-methoxy-2-(1-methylcyclopropyl)-1H-indole (155 mg) in N,N-dimethylformamide (3 mL) was added sodium hydride (dispersed in liquid paraffin, 50% or more, 39 mg) under ice-cooling. This mixture was stirred at room temperature for 50 minutes. Subsequently, a solution of 5-chloromethylfuran-2-carbonitrile (131 mg) in N,N-dimethylformamide (0.5 mL) was added thereto at room temperature, and the mixture was stirred at 80° C. for 14 hours. To the reaction mixture were added saturated aqueous ammonium chloride solution and water, followed by extraction with ethyl acetate. The organic layer was washed with water and saturated brine successively, dried over anhydrous magnesium sulfate, and then concentrated under reduced pressure. The residue was purified by aminopropylated silica gel column chromatography (eluting solvent: ethyl acetate-hexane) to obtain the title compound (34 mg). $^1$H-NMR (CDCl$_3$) δ ppm: 0.70-1.00 (4H, m), 1.35 (3H, s), 3.83 (3H, s), 5.45 (2H, s), 5.95-6.00 (1H, m), 6.20-6.30 (1H, m), 6.75-6.85 (1H, m), 6.90-7.10 (3H, m).

REFERENCE EXAMPLE 78

5-[6-Chloro-5-methoxy-2-(1-methylcyclopropyl)indol-1-ylmethyl]furan-2-carbonitrile In the same method as in Reference Example 77 using the corresponding starting material and reaction agents, the title compound was synthesized. $^1$H-NMR (CDCl$_3$) δ ppm: 0.70-1.00 (4H, m), 1.34 (3H, s), 3.91 (3H, s), 5.43 (2H, s), 5.95-6.05 (1H, m), 6.20-6.30 (1H, m), 7.00 (1H, d, J=3.6 Hz), 7.05 (1H, s), 7.15 (1H, s).

REFERENCE EXAMPLE 79

6-[2-(Butan-2-yl)-6-chloro-5-methoxyindol-1-ylmethyl]pyridine-2-carboxamidoxime

In the same method as in Reference Example 29 using the corresponding starting material and reaction agents, the title compound was synthesized. $^1$H-NMR (DMSO-d$_6$) δ ppm: 0.78 (3H, t, J=7.4 Hz), 1.18 (3H, d, J=6.9 Hz), 1.40-1.75 (2H, m), 2.80-3.00 (1H, m), 3.82 (3H, s), 5.51 (2H, s), 5.70 (2H, s), 6.28 (1H, s), 6.70-6.85 (1H, m), 7.18 (1H, s), 7.54 (1H, s), 7.65-7.75 (2H, m), 9.92 (1H, s).

REFERENCE EXAMPLE 80

6-(6-Chloro-5-methoxy-2-phenylindol-1-ylmethyl)pyridine-2-carboxamidoxime

In the same method as in Reference Example 29 using the corresponding starting material and reaction agents, the title compound was synthesized. $^1$H-NMR (DMSO-d$_6$) δ ppm: 3.85 (3H, s), 5.54 (2H, s), 5.59 (2H, s), 6.60-6.65 (1H, m), 6.83 (1H, dd, J=1.5, 7.1 Hz), 7.29 (1H, s), 7.35-7.75 (8H, m), 9.90 (1H, s). ESI-MS (m/z): 407 (M+H)$^+$

REFERENCE EXAMPLE 81

6-[2-(2,5-Difluorophenyl)-5-methoxyindol-1-ylmethyl]pyridine-2-carboxamidoxime

In the same method as in Reference Example 29 using the corresponding starting material and reaction agents, the title compound was synthesized. $^1$H-NMR (CDCl$_3$) δ ppm: 3.86 (3H, s), 5.36 (2H, s), 5.49 (2H, s), 6.45 (1H, s), 6.60-6.70 (2H, m), 6.85 (1H, dd, J=2.5, 9.0 Hz), 7.00-7.20 (5H, m), 7.51 (1H, t, J=7.8 Hz), 7.65-7.80 (1H, m).

REFERENCE EXAMPLE 82

5-(5-Methoxy-2-phenylindol-1-ylmethyl)furan-2-carboxamidoxime

In the same method as in Reference Example 29 using the corresponding starting material and reaction agents, the title compound was synthesized. $^1$H-NMR (DMSO-d$_6$) δ ppm: 3.76 (3H, s), 5.31 (2H, s), 5.50-5.60 (2H, br), 6.13 (1H, d, J=3.4 Hz), 6.45-6.55 (1H, m), 6.63 (1H, d, J=3.4 Hz), 6.79 (1H, dd, J=2.5, 8.9 Hz), 7.08 (1H, d, J=2.5 Hz), 7.40-7.65 (6H, m), 9.61 (1H, s).

REFERENCE EXAMPLE 83

6-[2-(Butan-2-yl)-5-methoxyindol-1-ylmethyl]pyridine-2-carboxamidoxime

In the same method as in Reference Example 29 using the corresponding starting material and reaction agents, the title compound was synthesized. $^1$H-NMR (DMSO-d$_6$) δ ppm: 0.80 (3H, t, J=7.4 Hz), 1.19 (3H, d, J=6.9 Hz), 1.40-1.75 (2H, m), 2.80-3.00 (1H, m), 3.73 (3H, s), 5.48 (2H, s), 5.74 (2H, s), 6.23 (1H, s), 6.60-6.80 (2H, m), 7.00 (1H, d, J=2.4 Hz), 7.26 (1H, d, J=8.9 Hz), 7.60-7.75 (2H, m), 9.91 (1H, s).

REFERENCE EXAMPLE 84

6-(6-Fluoro-5-methoxy-2-phenylindol-1-ylmethyl)pyridine-2-carboxamidoxime

In the same method as in Reference Example 29 using the corresponding starting material and reaction agents, the title compound was synthesized. $^1$H-NMR (CDCl$_3$) δ ppm: 3.94 (3H, s), 5.30-5.60 (4H, m), 6.55-6.65 (1H, m), 6.70-6.80 (1H, m), 6.90-7.00 (1H, m), 7.19 (1H, d, J=8.2 Hz), 7.30-7.50 (5H, m), 7.57 (1H, t, J=7.8 Hz), 7.70-7.85 (1H, m).

REFERENCE EXAMPLE 85

6-[6-Chloro-2-(furan-3-yl)-5-methoxyindol-1-ylmethyl]pyridine-2-carboxamidoxime

In the same method as in Reference Example 29 using the corresponding starting material and reaction agents, the title compound was synthesized. $^1$H-NMR (DMSO-d$_6$) δ ppm: 3.85 (3H, s), 5.63 (2H, s), 5.68 (2H, s), 6.65-6.85 (3H, m), 7.25 (1H, s), 7.60-7.80 (4H, m), 7.95-8.00 (1H, m), 9.92 (1H, s).

EXAMPLE 4-1

6-[2-(Butan-2-yl)-6-chloro-5-methoxyindol-1-ylmethyl]-N-(methanesulfonyl)pyridine-2-carboxamide

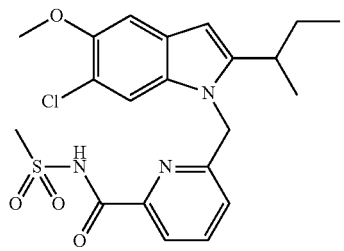 [SMILES: CCC(C)c1cc2cc(OC)c(Cl)cc2n1Cc1cccc(C(=O)NS(C)(=O)=O)n1]

To a solution of 6-[2-(butan-2-yl)-6-chloro-5-methoxyindol-1-ylmethyl]pyridine-2-carboxylic acid (68 mg) in dichloromethane (1.8 mL) were successively added methanesulfonamide (19 mg), 4-dimethylaminopyridine (49 mg), and 1-ethyl-3-(3-dimethylaminopropyl)carbodiimide hydrochloride (77 mg). This mixture was stirred for 62 hours at room temperature. To the reaction mixture was added 1 mol/L hydrochloric acid, followed by extraction with dichloromethane. The organic layer was washed with 1 mol/L hydrochloric acid and saturated brine successively, dried over anhydrous sodium sulfate, and then concentrated under reduced pressure. The residue was purified by silica gel column chromatography (eluting solvent: ethyl acetate-methanol) to obtain the title compound (62 mg). $^1$H-NMR (DMSO-d$_6$) δ ppm: 0.79 (3H, t, J=7.3 Hz), 1.19 (3H, d, J=6.9 Hz), 1.45-1.75 (2H, m), 2.80-2.95 (1H, m), 3.34 (3H, s), 3.83 (3H, s), 5.58 (2H, s), 6.32 (1H, s), 6.65-6.80 (1H, m), 7.20 (1H, s), 7.53 (1H, s), 7.85-7.95 (2H, m), 11.41 (1H, br s). ESI-MS (m/z): 450, 452 (M+H)$^+$ EXAMPLES 4-2 to 4-39

In the same method as in Example 4-1 using the corresponding starting material and reaction agents, the groups of the compounds shown in Tables 5 to 13 were synthesized.

EXAMPLES 5-1 to 5-8

In the same method as in Example 2-1 using the corresponding starting material and reaction agents, the groups of the compounds shown in Tables 14 and 15 were synthesized.

EXAMPLES 6-1 to 6-7

In the same method as in Example 3 using the corresponding starting material and reaction agents, the groups of the compounds shown in Tables 16 and 17 were synthesized.

EXAMPLE 7-1

3-{6-[2-(2,5-Difluorophenyl)-5-methoxyindol-1-ylmethyl]pyridin-2-yl}-4,5-dihydro-1,2,4-oxadiazol-5-thione

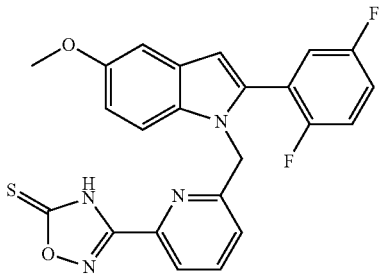 [SMILES: COc1ccc2c(c1)cc(-c1cc(F)ccc1F)n2Cc1cccc(-c2noc(=S)[nH]2)n1]

To a suspension of 6-[2-(2,5-difluorophenyl)-5-methoxyindol-1-ylmethyl]pyridine-2-carboxamidoxime (63 mg) in acetonitrile (1.54 mL) were successively added 1,1'-thiocarbonyldiimidazole (41 mg) and 1,8-diazabicyclo[5.4.0]undec-7-ene (0.092 mL), followed by stirring at room temperature for 3 hours. To the reaction mixture was added 1 mol/L hydrochloric acid, followed by extraction with ethyl acetate. The organic layer was washed with 1 mol/L hydrochloric acid, saturated aqueous sodium hydrogen carbonate solution, and saturated brine successively, dried over anhydrous sodium sulfate, and then concentrated under reduced pressure. The residue was purified by silica gel column chromatography (eluting solvent: ethyl acetate-methanol) to obtain the title compound (70 mg). $^1$H-NMR (DMSO-d$_6$) δ ppm: 3.77 (3H, s), 5.41 (2H, s), 6.50-6.60 (1H, m), 6.67 (1H, s), 6.80 (1H, dd, J=2.4, 9.0 Hz), 7.15 (1H, d, J=2.4 Hz), 7.25-7.45 (3H, m), 7.50-7.60 (1H, m), 7.65-7.80 (2H, m). ESI-MS (m/z): 451 (M+H)$^+$ EXAMPLES 7-2 and 7-3

In the same method as in Example 7-1 using the corresponding starting material and reaction agents, the groups of the compounds shown in Table 18 were synthesized.

EXAMPLE 8-1

N-Cyano-6-[2-(2,5-difluorophenyl)-5-methoxyindol-1-ylmethyl]pyridine-2-carboxamide

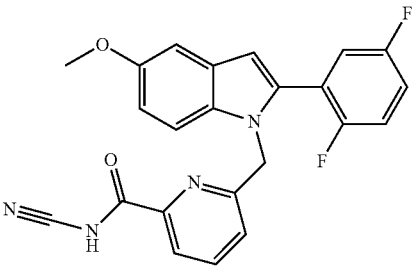 [SMILES: COc1ccc2c(c1)cc(-c1cc(F)ccc1F)n2Cc1cccc(C(=O)NC#N)n1]

To a solution of 6-[2-(2,5-difluorophenyl)-5-methoxyindol-1-ylmethyl]pyridine-2-carboxylic acid (70 mg) in dichloromethane (1.8 mL) were successively added cyanamide (8.2 mg), 4-dimethylaminopyridine (48 mg), and 1-ethyl-3-(3-dimethylaminopropyl)carbodiimide hydrochloride (75 mg). This mixture was stirred for 35 hours at room temperature. To the reaction mixture was added 1 mol/L hydrochloric acid, followed by extraction with dichloromethane. The organic layer was washed with 1 mol/L hydrochloric acid and saturated brine successively, dried over anhydrous sodium sulfate, and then concentrated under reduced pressure. The residue was purified by silica gel column chromatography (eluting solvent: ethyl acetate-methanol) to obtain the title compound (55 mg). $^1$H-NMR (DMSO-d$_6$) δ ppm: 3.77 (3H, s), 5.37 (2H, s), 6.45 (1H, d, J=7.4 Hz), 6.66 (1H, s), 6.79 (1H, dd, J=2.4, 8.9 Hz), 7.10-7.45 (4H, m), 7.50-7.85 (3H, m). ESI-MS (m/z): 419 (M+H)$^+$ EXAMPLES 8-2 to 8-8

In the same method as in Example 8-1 using the corresponding starting material and reaction agents, the groups of the compounds shown in Tables 19 and 20 were synthesized.

EXAMPLE 9

5-[6-(5-Methoxy-2-phenylindol-1-ylmethyl)pyridin-2-yl]-2,3-dihydro-1,3,4-oxadiazol-2-one

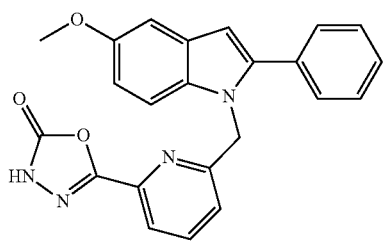 [SMILES: COc1ccc2c(c1)cc(-c1ccccc1)n2Cc1cccc(-c2n[nH]c(=O)o2)n1]

To a solution of methyl 6-(5-methoxy-2-phenylindol-1-ylmethyl)pyridine-2-carboxylate (70 mg) in methanol (1.2 mL) and tetrahydrofuran (0.4 mL) was added hydrazine monohydrate (0.091 mL). This mixture was stirred at room temperature overnight. The reaction mixture was concentrated under reduced pressure. The residue was dissolved in tetrahydrofuran (1 mL), and then 1,1'-carbonyldiimidazole (46 mg) was added thereto at room temperature. The mixture was stirred at room temperature for 2 hours. To the reaction mixture was added 1 mol/L hydrochloric acid, followed by extraction with ethyl acetate. The organic layer was washed with saturated brine, dried over anhydrous magnesium sulfate, and then concentrated under reduced pressure. The residue was purified by silica gel column chromatography (eluting solvent: ethyl acetate-hexane) to obtain the title compound (48 mg). $^1$H-NMR (DMSO-$d_6$) δ ppm: 3.77 (3H, s), 5.52 (2H, s), 6.62 (1H, s), 6.65-6.80 (2H, m), 7.13 (1H, d, J=2.5 Hz), 7.25 (1H, d, J=8.9 Hz), 7.35-7.50 (3H, m), 7.55-7.65 (2H, m), 7.75 (1H, d, J=7.9 Hz), 7.85 (1H, t, J=7.9 Hz), 12.78 (1H, br s). ESI-MS (m/z): 399 (M+H)$^+$

EXAMPLE 10

3-[6-(5-Methoxy-2-phenylindol-1-ylmethyl)pyridin-2-yl]-4,5-dihydro-1,2,4-thiadiazol-5-one

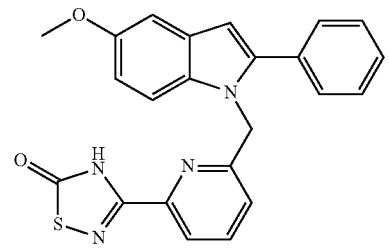

To a solution of 6-(5-methoxy-2-phenylindol-1-ylmethyl)pyridine-2-carboxamidoxime (123 mg) in tetrahydrofuran (2 mL) was added 1,1'-thiocarbonyldiimidazole (71 mg). This mixture was stirred at room temperature for 1 hour. To the reaction mixture was added water, followed by extraction with ethyl acetate. The organic layer was washed with water, dried over anhydrous magnesium sulfate, and then concentrated under reduced pressure. To the residue was added tetrahydrofuran (2 mL), and subsequently boron trifluoride ethyl ether complex (0.21 mL) was added thereto under ice-cooling. The mixture was stirred at room temperature for 3 days. To the reaction mixture was added water, followed by extraction with ethyl acetate. The organic layer was washed with 1 mol/L hydrochloric acid and water successively, dried over anhydrous magnesium sulfate, and then concentrated under reduced pressure. The residue was purified by silica gel column chromatography (eluting solvent: dichloromethane-methanol) to obtain the title compound (24 mg). $^1$H-NMR (DMSO-$d_6$) δ ppm: 3.77 (3H, s), 5.55 (2H, s), 6.45-6.55 (1H, m), 6.60-6.70 (1H, m), 6.77 (1H, dd, J=2.5, 8.9 Hz), 7.14 (1H, d, J=2.5 Hz), 7.28 (1H, d, J=8.9 Hz), 7.35-7.60 (5H, m), 7.75-7.95 (2H, m), 13.35 (1H, br s). ESI-MS (m/z): 415 (M+H)$^+$

TABLE 5

| Ex. No. | Strc | Physical Data |
|---|---|---|
| 4-2 | (structure) | $^1$H-NMR (DMSO-$d_6$) δ ppm: 0.79 (3H, t, J = 7.3 Hz), 1.19 (3H, d, J = 6.9 Hz), 1.25 (3H, t, J = 7.3 Hz), 1.45-1.70 (2H, m), 2.80-2.95 (1H, m), 3.52 (2H, q, J = 7.3 Hz), 3.82 (3H, s), 5.60 (2H, s), 6.31 (1H, s), 6.80-6.90 (1H, m), 7.20 (1H, s), 7.55 (1H, s), 7.85-8.00 (2H, m), 11.25 (1H, br s). ESI-MS (m/z): 464, 466 (M + H)$^+$ |
| 4-3 | (structure) | $^1$H-NMR (DMSO-$d_6$) δ ppm: 0.77 (3H, t, J = 7.3 Hz), 1.19 (3H, d, J = 6.8 Hz), 1.40-1.70 (2H, m), 2.75-2.95 (1H, m), 3.83 (3H, s), 5.59 (2H, s), 6.33 (1H, s), 6.81 (1H, d, J = 7.9 Hz), 7.22 (1H, s), 7.50-8.10 (8H, m), 11.82 (1H, br s). ESI-MS (m/z): 512, 514 (M + H)$^+$ |

TABLE 5-continued

| Ex. No. | Strc | Physical Data |
|---|---|---|
| 4-4 | | $^1$H-NMR (DMSO-d$_6$) δ ppm: 3.36 (3H, s), 3.77 (3H, s), 5.50 (2H, s), 6.65-6.90 (3H, m), 7.15 (1H, d, J = 2.4 Hz), 7.25-7.50 (4H, m), 7.80-7.95 (2H, m), 11.24 (1H, br s). ESI-MS (m/z): 472 (M + H)$^+$ |
| 4-5 | | $^1$H-NMR (DMSO-d$_6$) δ ppm: 1.23 (3H, t, J = 7.3 Hz), 3.50 (2H, q, J = 7.3 Hz), 3.77 (3H, s), 5.51 (2H, s), 6.69 (1H, s), 6.75-6.85 (2H, m), 7.15 (1H, d, J = 2.5 Hz), 7.20-7.45 (4H, m), 7.80-7.95 (2H, m), 11.08 (1H, br s). ESI-MS (m/z): 486 (M + H)$^+$ |

TABLE 6

| Ex. No. | Strc | Physical Data |
|---|---|---|
| 4-6 | | $^1$H-NMR (DMSO-d$_6$) δ ppm: 1.30 (6H, d, J = 6.9 Hz), 3.65-3.85 (4H, m), 5.52 (2H, s), 6.68 (1H, s), 6.80 (1H, dd, J = 2.4, 8.9 Hz), 6.85 (1H, d, J = 7.3 Hz), 7.14 (1H, d, J = 2.4 Hz), 7.20-7.50 (4H, m), 7.80-7.95 (2H, m), 10.96 (1H, br s). ESI-MS (m/z): 500 (M + H)$^+$ |
| 4-7 | | $^1$H-NMR (DMSO-d$_6$) δ ppm: 3.34 (3H, s), 3.87 (3H, s), 5.63 (2H, s), 6.75-6.90 (2H, m), 7.34 (1H, s), 7.40-7.55 (1H, m), 7.67 (1H, s), 7.80-8.05 (3H, m), 8.59 (1H, dd, J = 1.6, 4.9 Hz), 8.70-8.80 (1H, m), 11.14 (1H, br s). ESI-MS (m/z): 471, 473 (M + H)$^+$ |
| 4-8 | | $^1$H-NMR (DMSO-d$_6$) δ ppm: 1.23 (3H, t, J = 7.3 Hz), 3.50 (2H, q, J = 7.3 Hz), 3.87 (3H, s), 5.66 (2H, s), 6.75-6.95 (2H, m), 7.34 (1H, s), 7.45-7.55 (1H, m), 7.71 (1H, s), 7.80-8.05 (3H, m), 8.59 (1H, dd, J = 1.6, 4.8 Hz), 8.70-8.80 (1H, m), 10.70-11.40 (1H, br). ESI-MS (m/z): 485, 487 (M + H)$^+$ |

TABLE 6-continued

| Ex. No. | Strc | Physical Data |
|---|---|---|
| 4-9 | | ¹H-NMR (DMSO-d₆) δ ppm: 0.81 (3H, t, J = 7.3 Hz), 1.20 (3H, d, J = 6.8 Hz), 1.45-1.75 (2H, m), 2.80-2.95 (1H, m), 3.40 (3H, s), 3.73 (3H, s), 5.57 (2H, s), 6.27 (1H, s), 6.66 (1H, dd, J = 2.5, 8.8 Hz), 6.70-6.80 (1H, m), 7.02 (1H, d, J = 2.5 Hz), 7.24 (1H, d, J = 8.8 Hz), 7.85-7.95 (2H, m), 11.47 (1H, br s). ESI-MS (m/z): 416 (M + H)⁺ |

TABLE 7

| Ex. No. | Strc | Physical Data |
|---|---|---|
| 4-10 | | ¹H-NMR (DMSO-d₆) δ ppm: 0.80 (3H, t, J = 7.4 Hz), 1.10-1.30 (6H, m), 1.40-1.75 (2H, m), 2.80-2.95 (1H, m), 3.41 (2H, q, J = 7.4 Hz), 3.73 (3H, s), 5.55 (2H, s), 6.26 (1H, s), 6.55-6.75 (2H, m), 7.02 (1H, d, J = 2.4 Hz), 7.24 (1H, d, J = 8.9 Hz), 7.75-7.95 (2H, m), 11.35 (1H, br s). ESI-MS (m/z): 430 (M + H)⁺ |
| 4-11 | | ¹H-NMR (DMSO-d₆) δ ppm: 0.78 (3H, t, J = 7.4 Hz), 1.17 (3H, d, J = 6.8 Hz), 1.40-1.75 (2H, m), 2.75-2.90 (1H, m), 3.73 (3H, s), 5.49 (2H, s), 6.26 (1H, s), 6.30-6.50 (1H, br), 6.65 (1H, dd, J = 2.4, 8.9 Hz), 7.02 (1H, d, J = 2.4 Hz), 7.19 (1H, d, J = 8.9 Hz), 7.45-7.80 (5H, m), 7.85-8.05 (2H, m). ESI-MS (m/z): 478 (M + H)⁺ |
| 4-12 | | ¹H-NMR (DMSO-d₆) δ ppm: 0.97 (3H, t, J = 7.4 Hz), 1.60-1.80 (2H, m), 3.40-3.55 (2H, m), 3.76 (3H, s), 5.61 (2H, s), 6.60-6.65 (1H, m), 6.75 (1H, dd, J = 2.5, 8.9 Hz), 6.80-6.95 (1H, m), 7.13 (1H, d, J = 2.5 Hz), 7.31 (1H, d, J = 8.9 Hz), 7.35-7.60 (5H, m), 7.80-7.95 (2H, m), 11.08 (1H, br s). ESI-MS (m/z): 464 (M + H)⁺ |
| 4-13 | | ¹H-NMR (DMSO-d₆) δ ppm: 1.30 (6H, d, J = 6.8 Hz), 3.65-3.85 (4H, m), 5.62 (2H, s), 6.60-6.65 (1H, m), 6.75 (1H, dd, J = 2.4, 8.9 Hz), 6.90 (1H, d, J = 7.4 Hz), 7.12 (1H, d, J = 2.4 Hz), 7.32 (1H, d, J = 8.9 Hz), 7.35-7.60 (5H, m), 7.80-7.95 (2H, m), 10.96 (1H, br s). ESI-MS (m/z): 464 (M + H)⁺ |

TABLE 8

| Ex. No. | Strc | Physical Data |
| --- | --- | --- |
| 4-14 | | $^1$H-NMR (DMSO-d$_6$) δ ppm: 1.00-1.30 (4H, m), 3.00-3.15 (1H, m), 3.77 (3H, s), 5.61 (2H, s), 6.60-6.65 (1H, m), 6.76 (1H, dd, J = 2.4, 8.9 Hz), 6.80-6.90 (1H, m), 7.13 (1H, d, J = 2.4 Hz), 7.31 (1H, d, J = 8.9 Hz), 7.35-7.60 (5H, m), 7.80-7.95 (2H, m), 11.18 (1H, br s). ESI-MS (m/z): 462 (M + H)$^+$ |
| 4-15 | | $^1$H-NMR (DMSO-d$_6$) δ ppm: 3.77 (3H, s), 5.61 (2H, s), 6.60-6.85 (3H, s), 7.15 (1H, d, J = 2.5 Hz), 7.29 (1H, d, J = 8.8 Hz), 7.35-7.90 (10H, m), 7.95-8.05 (2H, m), 11.40-12.00 (1H, br). ESI-MS (m/z): 498 (M + H)$^+$ |
| 4-16 | | $^1$H-NMR (DMSO-d$_6$) δ ppm: 0.80 (3H, t, J = 7.3 Hz), 0.99 (3H, t, J = 7.4 Hz), 1.20 (3H, d, J = 6.8 Hz), 1.40-1.85 (4H, m), 2.80-2.95 (1H, m), 3.40-3.60 (2H, m), 3.73 (3H, s), 5.57 (2H, s), 6.27 (1H, s), 6.66 (1H, dd, J = 2.3, 8.8 Hz), 6.75-6.90 (1H, m), 7.01 (1H, d, J = 2.3 Hz), 7.25 (1H, d, J = 8.8 Hz), 7.85-8.00 (2H, m), 11.35 (1H, br s). ESI-MS (m/z): 444 (M + H)$^+$ |
| 4-17 | | $^1$H-NMR (DMSO-d$_6$) δ ppm: 0.80 (3H, t, J = 7.4 Hz), 1.20 (3H, d, J = 6.8 Hz), 1.25-1.40 (6H, m), 1.45-1.75 (2H, m), 2.80-2.95 (1H, m), 3.65-3.85 (4H, m), 5.58 (2H, s), 6.26 (1H, s), 6.66 (1H, dd, J = 2.4, 8.9 Hz), 6.83 (1H, dd, J = 1.6, 7.1 Hz), 7.01 (1H, d, J = 2.4 Hz), 7.26 (1H, d, J = 8.9 Hz), 7.80-8.00 (2H, m), 11.23 (1H, br s). ESI-MS (m/z): 444 (M + H)$^+$ |

TABLE 9

| Ex. No. | Strc | Physical Data |
| --- | --- | --- |
| 4-18 | | $^1$H-NMR (DMSO-d$_6$) δ ppm: 0.81 (3H, t, J = 7.3 Hz), 1.00-1.30 (7H, m), 1.40-1.75 (2H, m), 2.80-2.95 (1H, m), 3.05-3.15 (1H, m), 3.73 (3H, s), 5.57 (2H, s), 6.27 (1H, s), 6.66 (1H, dd, J = 2.5, 8.8 Hz), 6.70-6.85 (1H, m), 7.02 (1H, d, J = 2.5 Hz), 7.25 (1H, d, J = 8.8 Hz), 7.85-8.00 (2H, m), 11.43 (1H, br s). ESI-MS (m/z): 442 (M + H)$^+$ |

TABLE 9-continued

| Ex. No. | Strc | Physical Data |
| --- | --- | --- |
| 4-19 | | $^1$H-NMR (DMSO-$d_6$) δ ppm: 3.38 (3H, s), 3.85 (3H, s), 5.60 (2H, s), 6.60-6.70 (1H, m), 6.80-6.90 (1H, m), 7.32 (1H, d, J = 8.5 Hz), 7.35-7.60 (6H, m), 7.80-7.95 (2H, m), 11.16 (1H, br s). ESI-MS (m/z): 454 (M + H)$^+$ |
| 4-20 | | $^1$H-NMR (DMSO-$d_6$) δ ppm: 1.23 (3H, t, J = 7.3 Hz), 3.51 (2H, q, J = 7.3 Hz), 3.84 (3H, s), 5.61 (2H, s), 6.60-6.70 (1H, m), 6.85-6.95 (1H, m), 7.31 (1H, d, J = 8.6 Hz), 7.35-7.60 (6H, m), 7.80-7.95 (2H, m), 10.98 (1H, br s). ESI-MS (m/z): 468 (M + H)$^+$ |
| 4-21 | | $^1$H-NMR (DMSO-$d_6$) δ ppm: 1.30 (6H, d, J = 6.9 Hz), 3.65-3.80 (1H, m), 3.84 (3H, s), 5.62 (2H, s), 6.60-6.70 (1H, m), 6.90-7.00 (1H, m), 7.30 (1H, d, J = 8.5 Hz), 7.35-7.60 (6H, m), 7.80-7.95 (2H, m), 10.84 (1H, br s). ESI-MS (m/z): 482 (M + H)$^+$ |

TABLE 10

| Ex. No. | Strc | Physical Data |
| --- | --- | --- |
| 4-22 | | $^1$H-NMR (DMSO-$d_6$) δ ppm: 0.97 (3H, t, J = 7.6 Hz), 1.60-1.80 (2H, m), 3.40-3.55 (2H, m), 3.84 (3H, s), 5.61 (2H, s), 6.60-6.70 (1H, m), 6.85-6.95 (1H, m), 7.31 (1H, d, J = 8.5 Hz), 7.35-7.60 (6H, m), 7.80-7.95 (2H, m), 10.98 (1H, br s). ESI-MS (m/z): 482 (M + H)$^+$ |
| 4-23 | | $^1$H-NMR (DMSO-$d_6$) δ ppm: 1.05-1.30 (4H, m), 3.00-3.15 (1H, m), 3.85 (3H, s), 5.61 (2H, s), 6.60-6.70 (1H, m), 6.80-6.95 (1H, m), 7.32 (1H, d, J = 8.5 Hz), 7.35-7.60 (6H, m), 7.80-7.95 (2H, m), 11.09 (1H, br s). ESI-MS (m/z): 480 (M + H)$^+$ |

TABLE 10-continued

| Ex. No. | Strc | Physical Data |
| --- | --- | --- |
| 4-24 | | ¹H-NMR (DMSO-d₆) δ ppm:<br>1.21 (3H, t, J = 7.4 Hz), 3.43 (2H, q, J = 7.4 Hz), 3.86 (3H, s), 5.45 (2H, s), 6.20 (1H, d, J = 3.5 Hz), 6.55-6.65 (1H, m), 7.28 (1H, s), 7.40-7.65 (6H, m), 7.65-7.75 (1H, m), 11.93 (1H, br s).<br>ESI-MS (m/z): 473, 475 (M + H)⁺ |
| 4-25 | | ¹H-NMR (DMSO-d₆) δ ppm:<br>3.41 (3H, s), 3.86 (3H, s), 5.72 (2H, s), 6.70-6.90 (3H, m), 7.28 (1H, s), 7.69 (1H, s), 7.70-7.80 (1H, m), 7.85-8.05 (3H, m), 11.47 (1H, br s).<br>ESI-MS (m/z): 460 (M + H)⁺ |

TABLE 11

| Ex. No. | Strc | Physical Data |
| --- | --- | --- |
| 4-26 | | ¹H-NMR (DMSO-d₆) δ ppm:<br>1.26 (3H, t, J = 7.3 Hz), 3.53 (2H, q, J = 7.3 Hz), 3.86 (3H, s), 5.73 (2H, s), 6.70-6.90 (3H, m), 7.27 (1H, s), 7.65-7.80 (2H, m), 7.85-8.05 (3H, m), 11.31 (1H, br s).<br>ESI-MS (m/z): 474 (M + H)⁺ |
| 4-27 | | ¹H-NMR (DMSO-d₆) δ ppm:<br>0.65-0.90 (4H, m), 1.20-1.35 (6H, m), 3.53 (2H, q, J = 7.4 Hz), 3.72 (3H, s), 5.70 (2H, s), 6.25-6.35 (1H, m), 6.60-6.75 (2H, m), 6.95-7.10 (2H, m), 7.85-7.95 (2H, m), 11.37 (1H, br s).<br>ESI-MS (m/z): 428 (M + H)⁺ |
| 4-28 | | ¹H-NMR (DMSO-d₆) δ ppm:<br>0.65-0.85 (4H, m), 1.15-1.35 (6H, m), 3.51 (2H, q, J = 7.2 Hz), 3.82 (3H, s), 5.72 (2H, s), 6.30-6.35 (1H, m), 6.65-6.80 (1H, m), 7.20 (1H, s), 7.30 (1H, s), 7.85-8.00 (2H, m), 11.23 (1H, br s).<br>ESI-MS (m/z): 462 (M + H)⁺ |

TABLE 11-continued

| Ex. No. | Strc | Physical Data |
| --- | --- | --- |
| 4-29 | | ¹H-NMR (DMSO-d₆) δ ppm: 0.65-1.00 (4H, m), 1.21 (3H, t, J = 7.4 Hz), 1.36 (3H, s), 3.44 (2H, q, J = 7.4 Hz), 3.71 (3H, s), 5.54 (2H, s), 6.15-6.25 (1H, m), 6.34 (1H, d, J = 3.6 Hz), 6.69 (1H, dd, J = 2.4, 8.9 Hz), 6.96 (1H, d, J = 2.4 Hz), 7.25 (1H, d, J = 8.9 Hz), 7.49 (1H, d, J = 3.6 Hz), 11.96 (1H, br s). ESI-MS (m/z): 417 (M + H)⁺ |

TABLE 12

| Ex. No. | Strc | Physical Data |
| --- | --- | --- |
| 4-30 | | ¹H-NMR (DMSO-d₆) δ ppm: 0.70-1.00 (4H, m), 1.20 (3H, t, J = 7.4 Hz), 1.35 (3H, s), 3.42 (2H, q, J = 7.4 Hz), 3.80 (3H, s), 5.56 (2H, s), 6.20-6.30 (1H, m), 6.36 (1H, d, J = 3.4 Hz), 7.15 (1H, s), 7.40-7.55 (2H, m), 11.98 (1H, br s). ESI-MS (m/z): 451 (M + H)⁺ |
| 4-31 | | ¹H-NMR (DMSO-d₆) δ ppm: 3.77 (3H, s), 5.61 (2H, s), 6.64 (1H, s), 6.70-6.85 (2H, m), 7.13 (1H, d, J = 2.4 Hz), 7.31 (1H, d, J = 8.8 Hz), 7.35-7.60 (7H, m), 7.70-7.90 (3H, m), 7.95-8.10 (1H, m). ESI-MS (m/z): 516 (M + H)⁺ |
| 4-32 | | ¹H-NMR (DMSO-d₆) δ ppm: 3.77 (3H, s), 5.60 (2H, s), 6.60-6.80 (3H, m), 7.15 (1H, d, J = 2.4 Hz), 7.28 (1H, d, J = 8.8 Hz), 7.35-7.90 (11H, m). ESI-MS (m/z): 516 (M + H)⁺ |
| 4-33 | | ¹H-NMR (DMSO-d₆) δ ppm: 3.77 (3H, s), 5.60 (2H, s), 6.60-6.80 (3H, m), 7.15 (1H, d, J = 2.4 Hz), 7.28 (1H, d, J = 8.8 Hz), 7.35-7.60 (7H, m), 7.70-7.90 (2H, m), 8.00-8.15 (2H, m). ESI-MS (m/z): 516 (M + H)⁺ |

TABLE 12-continued

| Ex. No. | Strc | Physical Data |
|---|---|---|
| 4-34 | 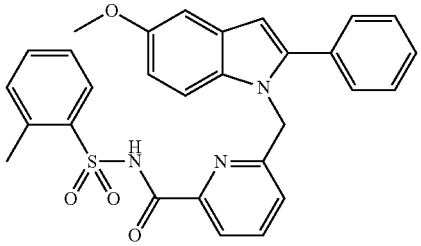 [SMILES: COc1ccc2c(c1)cc(-c1ccccc1)n2Cc1cccc(C(=O)NS(=O)(=O)c2ccccc2C)n1] | $^1$H-NMR (DMSO-d$_6$) δ ppm: 2.53 (3H, s), 3.77 (3H, s), 5.63 (2H, s), 6.64 (1H, s), 6.76 (1H, dd, J = 2.4, 8.8 Hz), 6.80-6.95 (1H, m), 7.13 (1H, d, J = 2.4 Hz), 7.25-7.90 (11H, m), 7.95-8.10 (1H, m), 11.40-12.00 (1H, br). ESI-MS (m/z): 512 (M + H)$^+$ |

TABLE 13

| Ex. No. | Strc | Physical Data |
|---|---|---|
| 4-35 | 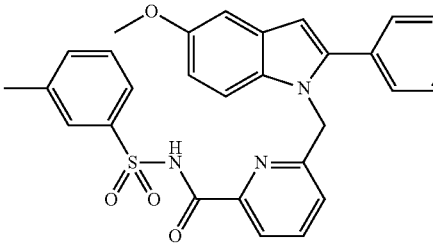 | $^1$H-NMR (DMSO-d$_6$) δ ppm: 2.41 (3H, s), 3.77 (3H, s), 5.61 (2H, s), 6.65 (1H, s), 6.70-6.85 (2H, m), 7.15 (1H, d, J = 2.4 Hz), 7.30 (1H, d, J = 8.8 Hz), 7.35-7.60 (7H, m), 7.70-7.90 (4H, m), 11.30-11.90 (1H, br). ESI-MS (m/z): 512 (M + H)$^+$ |
| 4-36 | 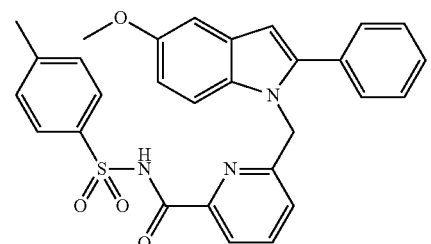 | $^1$H-NMR (DMSO-d$_6$) δ ppm: 2.39 (3H, s), 3.77 (3H, s), 5.60 (2H, s), 6.65 (1H, s), 6.70-6.85 (2H, m), 7.15 (1H, d, J = 2.4 Hz), 7.29 (1H, d, J = 8.9 Hz), 7.35-7.60 (7H, m), 7.65-7.95 (4H, m), 11.30-11.90 (1H, br). ESI-MS (m/z): 512 (M + H)$^+$ |
| 4-37 | 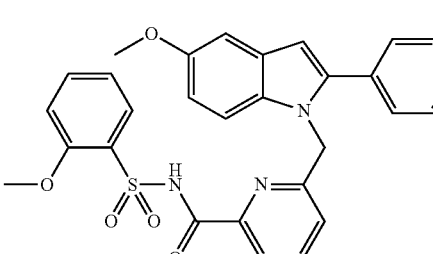 | $^1$H-NMR (DMSO-d$_6$) δ ppm: 3.66 (3H, s), 3.77 (3H, s), 5.64 (2H, s), 6.64 (1H, s), 6.76 (1H, dd, J = 2.5, 8.9 Hz), 6.95-8.05 (14H, m), 11.04 (1H, br s). ESI-MS (m/z): 528 (M + H)$^+$ |
| 4-38 | 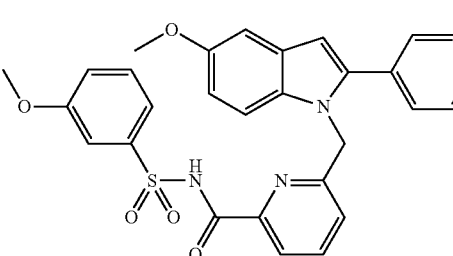 | $^1$H-NMR (DMSO-d$_6$) δ ppm: 3.77 (3H, s), 3.84 (3H, s), 5.61 (2H, s), 6.65 (1H, s), 6.70-6.85 (2H, m), 7.14 (1H, d, J = 2.3 Hz), 7.20-7.65 (10H, m), 7.70-7.90 (2H, m), 11.40-12.00 (1H, br). ESI-MS (m/z): 528 (M + H)$^+$ |

TABLE 13-continued

| Ex. No. | Strc | Physical Data |
| --- | --- | --- |
| 4-39 | | ¹H-NMR (DMSO-d$_6$) δ ppm: 3.77 (3H, s), 3.85 (3H, s), 5.60 (2H, s), 6.65 (1H, s), 6.70-6.85 (2H, m), 7.05-7.20 (3H, m), 7.29 (1H, d, J = 8.8 Hz), 7.35-7.60 (5H, m), 7.70-8.00 (4H, m), 11.30-11.70 (1H, br).<br>ESI-MS (m/z): 528 (M + H)⁺ |

TABLE 14

| Ex. No. | Strc | Physical Data |
| --- | --- | --- |
| 5-1 | | ¹H-NMR (DMSO-d$_6$) δ ppm: 0.78 (3H, t, J = 7.4 Hz), 1.19 (3H, d, J = 6.8 Hz), 1.40-1.75 (2H, m), 2.75-2.95 (1H, m), 3.74 (3H, s), 5.45-5.70 (2H, m), 6.29 (1H, s), 6.45-6.55 (1H, m), 6.68 (1H, dd, J = 2.4, 8.8 Hz), 7.04 (1H, d, J = 2.4 Hz), 7.27 (1H, d, J = 8.8 Hz), 7.90 (1H, t, J = 7.8 Hz), 8.00-8.15 (1H, m).<br>ESI-MS (m/z): 363 (M + H)⁺ |
| 5-2 | | ¹H-NMR (DMSO-d$_6$) δ ppm: 3.86 (3H, s), 5.50 (2H, s), 6.27 (1H, d, J = 3.5 Hz), 6.55-6.65 (1H, m), 7.09 (1H, d, J = 3.5 Hz), 7.29 (1H, s), 7.40-7.65 (5H, m), 7.70-7.80 (1H, m).<br>ESI-MS (m/z): 406, 408 (M + H)⁺ |
| 5-3 | | ¹H-NMR (DMSO-d$_6$) δ ppm: 3.87 (3H, s), 5.58 (2H, s), 6.50 (1H, d, J = 7.8 Hz), 6.67 (1H, s), 7.25-7.60 (7H, m), 7.87 (1H, t, J = 7.8 Hz), 8.02 (1H, d, J = 7.8 Hz).<br>ESI-MS (m/z): 401 (M + H)⁺ |
| 5-4 | | ¹H-NMR (DMSO-d$_6$) δ ppm: 3.87 (3H, s), 5.70 (2H, s), 6.55 (1H, d, J = 7.8 Hz), 6.70-6.85 (2H, m), 7.30 (1H, s), 7.65-7.80 (2H, m), 7.85-8.00 (2H, m), 8.07 (1H, d, J = 7.8 Hz).<br>ESI-MS (m/z): 407 (M + H)⁺ |

TABLE 15

| Ex. No. | Strc | Physical Data |
|---|---|---|
| 5-5 | | $^1$H-NMR (DMSO-d$_6$) δ ppm: 0.65-0.90 (4H, m), 1.26 (3H, s), 3.73 (3H, s), 5.69 (2H, s), 6.25-6.35 (2H, m), 6.67 (1H, dd, J = 2.5, 8.9 Hz), 7.03 (1H, d, J = 2.5 Hz), 7.07 (1H, d, J = 8.9 Hz), 7.80 (1H, t, J = 7.8 Hz), 8.01 (1H, d, J = 7.8 Hz). ESI-MS (m/z): 361 (M + H)$^+$ |
| 5-6 | | $^1$H-NMR (DMSO-d$_6$) δ ppm: 0.65-0.90 (4H, m), 1.23 (3H, s), 3.83 (3H, s), 5.72 (2H, s), 6.30-6.40 (2H, m), 7.22 (1H, s), 7.37 (1H, s), 7.85 (1H, t, J = 7.8 Hz), 8.05 (1H, d, J = 7.8 Hz). ESI-MS (m/z): 395 (M + H)$^+$ |
| 5-7 | | $^1$H-NMR (DMSO-d$_6$) δ ppm: 0.70-1.00 (4H, m), 1.39 (3H, s), 3.71 (3H, s), 5.59 (2H, s), 6.15-6.25 (1H, m), 6.44 (1H, d, J = 3.4 Hz), 6.70 (1H, dd, J = 2.4, 8.9 Hz), 6.96 (1H, d, J = 2.4 Hz), 7.14 (1H, d, J = 3.4 Hz), 7.31 (1H, d, J = 8.9 Hz). ESI-MS (m/z): 350 (M + H)$^+$ |
| 5-8 | | $^1$H-NMR (DMSO-d$_6$) δ ppm: 0.70-1.00 (4H, m), 1.38 (3H, s), 3.80 (3H, s), 5.61 (2H, s), 6.20-6.30 (1H, m), 6.45 (1H, d, J = 3.4 Hz), 7.05-7.20 (2H, m), 7.50-7.60 (1H, m). ESI-MS (m/z): 384 (M + H)$^+$ |

TABLE 16

| Ex. No. | Strc | Physical Data |
|---|---|---|
| 6-1 | | $^1$H-NMR (DMSO-d$_6$) δ ppm: 0.76 (3H, t, J = 7.4 Hz), 1.16 (3H, d, J = 6.8 Hz), 1.40-1.70 (2H, m), 2.75-2.90 (1H, m), 3.83 (3H, s), 5.45-5.65 (2H, m), 6.32 (1H, s), 6.55-6.65 (1H, m), 7.21 (1H, s), 7.57 (1H, s), 7.80-7.95 (2H, m), 13.17 (1H, br s). ESI-MS (m/z): 413 (M + H)$^+$ |
| 6-2 | | $^1$H-NMR (DMSO-d$_6$) δ ppm: 3.87 (3H, s), 5.57 (2H, s), 6.55-6.70 (2H, m), 7.34 (1H, s), 7.35-7.55 (5H, m), 7.57 (1H, s), 7.75-7.95 (2H, m), 13.08 (1H, br s). ESI-MS (m/z): 433 (M + H)$^+$ |

TABLE 16-continued

| Ex. No. | Strc | Physical Data |
| --- | --- | --- |
| 6-3 | | ¹H-NMR (DMSO-d₆) δ ppm:<br>3.78 (3H, s), 5.47 (2H, s), 6.60 (1H, d, J = 7.8 Hz), 6.70 (1H, s), 6.82 (1H, dd, J = 2.4, 9.0 Hz), 7.16 (1H, d, J = 2.4 Hz), 7.25-7.50 (4H, m), 7.75-7.90 (2H, m), 13.03 (1H, br s).<br>ESI-MS (m/z): 435 (M + H)⁺ |
| 6-4 | | ¹H-NMR (DMSO-d₆) δ ppm:<br>3.77 (3H, s), 5.44 (2H, s), 6.30 (1H, d, J = 3.6 Hz), 6.50-6.60 (1H, m), 6.81 (1H, d, J = 2.5, 8.8 Hz), 7.03 (1H, d, J = 3.6 Hz), 7.09 (1H, d, J = 2.5 Hz), 7.35-7.65 (6H, m), 12.97 (1H, br s).<br>ESI-MS (m/z): 388 (M + H)⁺ |

TABLE 17

| Ex. No. | Strc | Physical Data |
| --- | --- | --- |
| 6-5 | | ¹H-NMR (DMSO-d₆) δ ppm:<br>0.79 (3H, t, J = 7.4 Hz), 1.18 (3H, d, J = 6.8 Hz), 1.40-1.75 (2H, m), 2.75-2.95 (1H, m), 3.74 (3H, s), 5.45-5.60 (2H, m), 6.27 (1H, s), 6.50-6.60 (1H, m), 6.68 (1H, dd, J = 2.4, 8.9 Hz), 7.03 (1H, d, J = 2.4 Hz), 7.25 (1H, d, J = 8.9 Hz), 7.80-7.95 (2H, m), 13.16 (1H, br s).<br>ESI-MS (m/z): 379 (M + H)⁺ |
| 6-6 | | ¹H-NMR (DMSO-d₆) δ ppm:<br>3.86 (3H, s), 5.55 (2H, s), 6.50-6.70 (2H, m), 7.25-7.60 (7H, m), 7.75-7.95 (2H, m), 13.08 (1H, br s).<br>ESI-MS (m/z): 415 (M − H)⁻ |
| 6-7 | | ¹H-NMR (DMSO-d₆) δ ppm:<br>3.87 (3H, s), 5.66 (2H, s), 6.55-6.65 (1H, m), 6.70-6.85 (2H, m), 7.29 (1H, s), 7.69 (1H, s), 7.70-8.00 (4H, m), 13.19 (1H, br s).<br>ESI-MS (m/z): 423 (M + H)⁺ |

TABLE 18

| Ex. No. | Strc | Physical Data |
|---|---|---|
| 7-2 | | $^1$H-NMR (DMSO-$d_6$) δ ppm: 3.77 (3H, s), 5.55 (2H, s), 6.55-6.70 (2H, m), 6.77 (1H, dd, J = 2.4, 8.9 Hz), 7.15 (1H, d, J = 2.4 Hz), 7.26 (1H, d, J = 8.9 Hz), 7.35-7.60 (5H, m), 7.80-7.95 (2H, m). ESI-MS (m/z): 415 (M + H)$^+$ |
| 7-3 | | $^1$H-NMR (DMSO-$d_6$) δ ppm: 0.76 (3H, t, J = 7.4 Hz), 1.17 (3H, d, J = 6.8 Hz), 1.40-1.70 (2H, m), 2.75-2.95 (1H, m), 3.83 (3H, s), 5.45-5.65 (2H, m), 6.31 (1H, s), 6.55-6.70 (1H, m), 7.21 (1H, s), 7.57 (1H, s), 7.80-7.95 (2H, m). ESI-MS (m/z): 429, 431 (M + H)$^+$ |

TABLE 19

| Ex. No. | Strc | Physical Data |
|---|---|---|
| 8-2 | | $^1$H-NMR (DMSO-$d_6$) δ ppm: 3.77 (3H, s), 5.46 (2H, s), 6.41 (1H, d, J = 7.7 Hz), 6.62 (1H, s), 6.75 (1H, dd, J = 2.4, 8.8 Hz), 7.05-7.25 (2H, m), 7.30-7.90 (7H, m). ESI-MS (m/z): 383 (M + H)$^+$ |
| 8-3 | | $^1$H-NMR (DMSO-$d_6$) δ ppm: 3.87 (3H, s), 5.56 (2H, s), 6.57 (1H, d, J = 7.7 Hz), 6.68 (1H, s), 7.33 (1H, s), 7.35-7.60 (6H, m), 7.83 (1H, t, J = 7.7 Hz), 7.90 (1H, d, J = 7.7 Hz). ESI-MS (m/z): 417 (M + H)$^+$ |
| 8-4 | | $^1$H-NMR (DMSO-$d_6$) δ ppm: 3.88 (3H, s), 5.61 (2H, s), 6.70 (1H, dd, J = 1.2, 7.4 Hz), 6.75-6.85 (1H, m), 7.36 (1H, s), 7.45-7.55 (1H, m), 7.69 (1H, s), 7.85-8.00 (3H, m), 8.59 (1H, dd, J = 1.6, 4.8 Hz), 8.65-8.75 (1H, m). ESI-MS (m/z): 418, 4.20 (M + H)$^+$ |
| 8-5 | | $^1$H-NMR (DMSO-$d_6$) δ ppm: 3.77 (3H, s), 5.30 (2H, s), 5.96 (1H, d, J = 3.2 Hz), 6.45-6.55 (1H, m), 6.60 (1H, d, J = 3.2 Hz), 6.79 (1H, dd, J = 2.4, 8.9 Hz), 7.08 (1H, d, J = 2.4 Hz), 7.30-7.70 (6H, m). ESI-MS (m/z): 372 (M + H)$^+$ |

TABLE 20

| Ex. No. | Strc | Physical Data |
|---|---|---|
| 8-6 | | $^1$H-NMR (DMSO-d$_6$) δ ppm: 0.78 (3H, t, J = 7.4 Hz), 1.18 (3H, d, J = 6.7 Hz), 1.40-1.75 (2H, m), 2.75-2.90 (1H, m), 3.74 (3H, s), 5.40-5.60 (2H, m), 6.27 (1H, s), 6.46 (1H, d, J = 7.9 Hz), 6.67 (1H, dd, J = 2.5, 8.8 Hz), 7.02 (1H, d, J = 2.5 Hz), 7.22 (1H, d, J = 8.8 Hz), 7.77 (1H, t, J = 7.8 Hz), 7.89 (1H, d, J = 7.8 Hz). ESI-MS (m/z): 363 (M + H)$^+$ |
| 8-7 | | $^1$H-NMR (DMSO-d$_6$) δ ppm: 3.86 (3H, s), 5.57 (2H, s), 6.55-6.70 (2H, m), 7.20-7.55 (7H, m), 7.85-8.00 (2H, m), ESI-MS (m/z): 401 (M + H)$^+$ |
| 8-8 | | $^1$H-NMR (DMSO-d$_6$) δ ppm: 3.85 (3H, s), 5.34 (2H, s), 5.95 (1H, d, J = 3.3 Hz), 6.50-6.65 (2H, m), 7.27 (1H, s), 7.35-7.70 (6H, m). ESI-MS (m/z): 404, 406 (M − H)$^−$ |

TEST EXAMPLE 1

Test for Confirmation of EP$_1$ Receptor Antagonism (1) Preparation of Rat EP$_1$ Expression Vector Using Rat Kidney BD Marathon-Ready cDNA (Nippon Becton Dickinson Company, Ltd.) as a template, and using a forward primer shown in (SEQ ID NO:1) and a reverse primer shown in (SEQ ID NO:2), a first run of PCR was carried out using KOD-Plus-Ver 2.0 (Toyobo Co., Ltd.). Further, using this amplification product as a template, and using a forward primer shown in (SEQ ID NO:3) and a reverse primer shown in (SEQ ID NO:4), a second run of PCR was carried out in the same manner. The amplification product obtained by the second run of PCR was incorporated into a vector (pcDNA3.1 D/V5-His-TOPO (registered trademark), Invitrogen Japan K. K.). By a conventional method, the vector containing this amplification product was introduced into E. coli (One Shot TOP10 Competent Cells, Invitrogen Corporation) and transformed. This transformed E. coli was cultured in an LB agar medium for one day. After the culture, colonies were selected and cultured in an LB liquid medium containing 50 μg/mL of ampicillin. After the culture, the vector was purified using a QIAprep Spin Miniprep Kit (Qiagen K. K.). The base sequence of the insertion site of this vector (SEQ ID NO:5) was compared with the rat EP$_1$ base sequence (Ptger1) registered as Accession No. NM_013100 in a publicly-known database (NCBI), and as a result, the base sequences completely matched except for a single base. Further, the amino acid sequence translated by the base sequence completely matched the amino acid sequence of the rat EP$_1$ receptor registered as an NCBI Accession No. NP_037232. Therefore, it was confirmed that the cloned gene sequence was a base sequence of the rat EP$_1$ receptor and the obtained amino acid sequence was that of the rat EP$_1$ receptor. The pcDNA3.1 D/V5-His-TOPO (registered trademark) into which the nucleic acid shown in (SEQ ID NO:5) had been inserted was taken as a rat EP$_1$-expressing vector.

(2) Preparation of Rat EP$_1$ Receptor-Expressing Cells (2-1) COS-1 Cell Culture COS-1 cells (Dainippon Sumitomo Pharma Co., Ltd.) were cultured until they reached confluence in an incubator at 37° C. under a 5% CO$_2$ gas condition, using a D-MEM liquid medium (high glucose and L-glutamine contained, Invitrogen Corporation) to which a penicillin-streptomycin solution (Invitrogen Corporation, final concentration: 100 U/mL as benzylpenicillin; 100 μg/mL as streptomycin) as an antibiotic, MEM nonessential amino acids (Invitrogen Corporation, final concentration: 0.1 mM), and fetal calf serum (Sanko Junyaku Co., Ltd., final concentration: 10%) were added.

(2-2) COS-1 Cell Subculture

The cells that had reached confluence were stripped with 0.05% trypsin/0.53 mM EDTA•4Na (Invitrogen Japan K. K.) and resuspended in the liquid medium. The resuspended cells were diluted and cultured in the liquid medium at a spread ratio from 1:4 to 1:8.

(2-3) Preparation of Cells for Introduction of Rat EP$_1$-Expressing Vector

The cells that had reached confluence were stripped with 0.05% trypsin/0.53 mM EDTA•4Na, and resuspended in a D-MEM liquid medium (high glucose and L-glutamine contained, Invitrogen Corporation) to which MEM nonessential amino acids (final concentration: 0.1 mM) and fetal calf serum (final concentration: 10%) were added. In each well of a Poly D-lysine-coated 96-well microplate (BD BioCoat (registered trademark), Nippon Becton Dickinson Company, Ltd.), this resuspended cell suspension culture was prepared to be $5 \times 10^4$ cells/well in 100 µL of the liquid medium, and 100 µL of the cell suspension was dispensed and seeded in each well. After seeding, the cells were cultured in an incubator at 37° C. under a 5% $CO_2$ gas condition. Once the cells for introduction of a rat $EP_1$-expressing vector were adhered (about 2 hours after seeding), introduction of the rat $EP_1$-expressing vector was carried out in the following order.

(2-4) Introduction of Rat $EP_1$-Expressing Vector

For introduction of the rat $EP_1$-expressing vector, Lipofectamine 2000 (Invitrogen Japan K. K.) was used. The rat $EP_1$-expressing vector was diluted with OPTI-MEM (registered trademark) I Reduced-Serum Medium (Invitrogen Japan K. K.) to 200 ng/25 µL/well, and at the same time, Lipofectamine 2000 (Invitrogen Japan K. K.) was diluted with OPTI-MEM (registered trademark) I Reduced-Serum Medium (Invitrogen Japan K. K.) to 0.5 µL/25 µL/well, followed by incubation at room temperature for 5 minutes. After incubation for 5 minutes, in order to form a complex of the rat $EP_1$-expressing vector/Lipofectamine 2000, the diluted rat $EP_1$-expressing vector and the diluted Lipofectamine 2000 were mixed and incubated at room temperature for 30 minutes. After incubation for 30 minutes, the complex of the rat $EP_1$-expressing vector/Lipofectamine 2000 was distributed to the cells for introduction of the rat $EP_1$-expressing vector at 50 µL/well. The cells to which the complex of the rat $EP_1$-expressing vector/Lipofectamine 2000 had been distributed were cultured in an incubator at 37° C. for 20 hours under a 5% $CO_2$ gas condition. After the culture for 20 hours, the cells were used for measurement of an intracellular calcium concentration as rat $EP_1$ receptor-expressing cells.

(3) Study on Inhibitory Effect on Increase in Intracellular Calcium Concentration Using the rat $EP_1$ receptor-expressing cells, the inhibitory effect of each test compound on the increase in intracellular calcium concentration induced by prostaglandin $E_2$ was studied in accordance with the method shown below.

A 10 mM solution of each test compound in dimethyl sulfoxide was diluted with an assay buffer (20 mM HEPES/Hank's Balanced Salt Solution (HBSS), pH 7.2).

The rat $EP_1$ receptor-expressing cells were washed with the assay buffer. 100 µL of a fluorescent calcium indicator (Calcium kit II, Fluo 4 (Dojindo Laboratories): prepared by the protocol of the same product, Invitrogen Japan K. K., 2.5 mM probenecid contained) was added to each well, followed by incubation in an incubator at 37° C. for 60 minutes. Then, the intracellular calcium concentration was measured immediately.

The intracellular calcium concentration was measured as a fluorescence signal using FDSS (registered trademark) 7000 (manufactured by Hamamatsu Photonics K. K.). 50 µL of each test compound (final concentrations: 1 nM to 10 µM) was added to each well after 20 seconds from initiating the reading of the fluorescence signal, and the fluorescence signal was measured for 60 seconds. Then, 50 µL of a prostaglandin $E_2$ buffer solution was then added to each well (final concentration 10 nM) and the fluorescence signal was measured for 60 seconds.

In the method above, a fluorescence signal obtained by the addition of the prostaglandin $E_2$ with the addition of the assay buffer instead of the test compound was regarded as 100%, and a signal obtained without the addition of either the test compound or the prostaglandin $E_2$ was regarded as 0%. The concentration of the test compound showing 50% inhibition from the concentration-response curve was regarded as an $IC_{50}$ value. As the values of the $EP_1$ receptor antagonism, the obtained $IC_{50}$ values of each test compound were shown in Table 21 below.

TABLE 21

| Ex. No. | $IC_{50}$ (nM) |
|---|---|
| 1-1 | 47 |
| 1-5 | 49 |
| 1-6 | 19 |
| 1-12 | 81 |
| 2-1 | 34 |
| 2-2 | 42 |
| 2-3 | 67 |
| 2-4 | 32 |
| 4-2 | 31 |
| 4-5 | 47 |
| 4-10 | 46 |
| 4-12 | 30 |
| 4-13 | 37 |
| 4-14 | 63 |
| 4-16 | 43 |
| 4-17 | 49 |
| 4-18 | 31 |
| 4-19 | 60 |
| 4-20 | 40 |
| 4-22 | 59 |
| 4-23 | 28 |
| 5-1 | 23 |
| 5-3 | 31 |
| 5-4 | 35 |
| 5-5 | 24 |
| 5-6 | 33 |
| 5-7 | 64 |
| 6-6 | 22 |
| 8-7 | 97 |

As shown in Table 21, it is apparent that the compounds of the present invention exhibit potent $EP_1$ receptor antagonism.

TEST EXAMPLE 2

Inhibitory Effect of Compound on Sulprostone-Induced Bladder Contraction

Female SD rats were used. Under urethane anesthesia (1.25 g/kg, administered subcutaneously), a tracheal cannula (Size 8, HIBIKI) and a femoral vein cannula for administration (23G needle-equipped PESO) were inserted thereinto. The bladder cannula (PE50) was inserted from the bladder apex. The bladder cannula was connected to a three-way stopcock, and then one port was connected to a pressure transducer and the other port was connected to a syringe filled with saline. Saline was injected into the bladder at an injection rate of 3.6 mL/hour and the bladder contraction pressure was recorded at the time of injection with a recorder (RECTI-HORITZ-8K, NEC Corporation). After 10 minutes from stabilization of the bladder contraction pressure during urination, sulprostone was administered subcutaneously (0.3 mg/kg). Subsequently, once the bladder contraction pressure became constant, a test agent was administered intravenously (1.0 mg/kg). An average bladder contraction pressure during the 10 minute period before administration of sulprostone was used as a baseline (0%). Further, an average bladder contraction pressure during the 10 minute period directly before administration of the test agent was used as a maximum bladder contraction pressure (100%). The average bladder contraction pressures were measured for a 5 minute period before and after 15 minutes and 60 minutes from administration of the test agent. The ratio of this measured value to the maximum bladder contraction pressure was calculated by the following equation and regarded as an average bladder contraction rate after administration of the test agent:

$$(\text{Average Bladder Contraction Rate after Administration of Test Agent (\%)}) = [(\text{Average Bladder Contraction Pressure after Administration of Test Agent})/(\text{Maximum Bladder Contraction Pressure})] \times 100 \quad \text{EQUATION 1}$$

In addition, the difference between the maximum bladder contraction rate (100%) and the average bladder contraction rate (%) after administration of the test agent was calculated by the following equation and regarded as a bladder contraction inhibition rate of the test agent:

$$(\text{Bladder Contraction Inhibition Rate}) = 100\% - (\text{Average Bladder Contraction Rate after Administration of Test Agent (\%)}) \quad \text{EQUATION 2}$$

The results were shown in Table 22.

TABLE 22

| Ex. No. | Bladder Contraction Inhibition Rate (%) | |
|---|---|---|
| | 15 minutes | 60 minutes |
| 1-1 | 67.3 | 75.5 |
| 1-6 | 70.0 | 35.8 |
| 2-1 | 73.2 | 78.1 |
| 5-5 | 85.3 | 55.2 |

From the results above, it was found that the compounds of the present invention exhibited potent and sustained inhibition of the bladder contraction even when administered in vivo.

The compound of the present invention has a potent $EP_1$ receptor antagonism, and therefore, it is useful as an agent for treating or preventing diseases or symptoms caused by activation of an $EP_1$ receptor due to a stimulant action of $PGE_2$. In particular, it is useful as an agent for treating or preventing lower urinary tract symptoms (LUTS), particularly overactive bladder syndrome (OABs).

SEQ ID NO:1 is a sequence of a forward primer (5' primer) used for amplification of DNA of SEQ ID NO:5.

SEQ ID NO:2 is a sequence of a reverse primer (3' primer) used for amplification of DNA of SEQ ID NO:5.

SEQ ID NO:3 is a sequence of a forward primer (5' primer) used for amplification of DNA of SEQ ID NO:5.

SEQ ID NO:4 is a sequence of a reverse primer (3' primer) used for amplification of DNA of SEQ ID NO:5.

SEQ ID NO:5 is a DNA sequence for expressing a rat $EP_1$ receptor which is amplified using the primers of SEQ ID NO:1, SEQ ID NO:2, SEQ ID NO:3, and SEQ ID NO:4.

What is claimed is:

1. A compound represented by the general formula (I) or a pharmaceutically acceptable salt thereof:

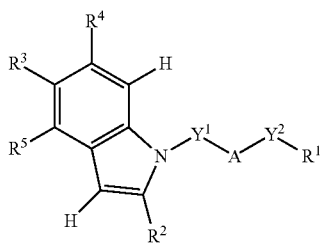

(I)

wherein A represents a group selected from the group consisting of the following a) to h):

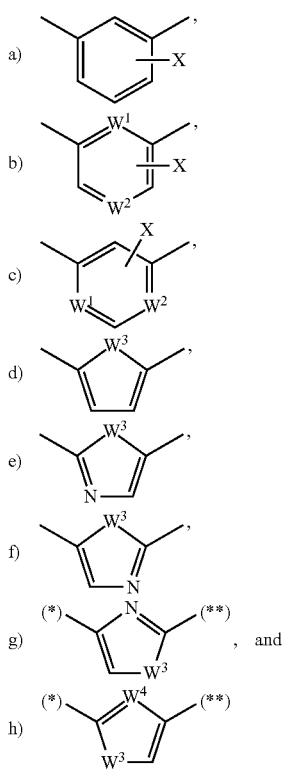

one of $W^1$ and $W^2$ represents a nitrogen atom and the other represents =CH— or a nitrogen atom;
$W^3$ represents an oxygen atom or a sulfur atom;
$W^4$ represents =CH— or a nitrogen atom;

X represents a hydrogen atom or a halogen atom;
$Y^1$ represents a $C_{1-6}$ alkylene group;
$Y^2$ represents a single bond or an oxy-$C_{1-6}$ alkylene group;
$R^1$ represents a group selected from the group consisting of the following i) to n):
  i) —C(=O)—NH—SO$_2$—R$^6$,
  j) —C(=O)—NH—OH,
  k) —C(=O)—NH—CN,
  l) —NH—C(=O)—R$^6$,
  m) an acidic 5-membered hetero ring group, and
  n) a 6-membered aromatic ring group substituted with a phenolic hydroxy group;
$R^2$ represents a group selected from the group consisting of the following o) to t):
  o) a branched $C_{3-6}$ alkyl group,
  p) a halo-$C_{1-6}$ alkyl group,
  q) a $C_{3-6}$ cycloalkyl group, in which the ring is unsubstituted or substituted with one $C_{1-6}$ alkyl group,
  r) a phenyl group, in which the ring is unsubstituted or substituted with one to five groups independently selected from the group consisting of the following: a halogen atom, a $C_{1-6}$ alkyl group, a halo-$C_{1-6}$ alkyl group, a hydroxy-$C_{1-6}$ alkyl group, a $C_{1-6}$ alkoxy group, and a cyano group,
  s) a 6-membered aromatic heterocyclic group, in which the ring is unsubstituted or substituted with one to four groups independently selected from the group consisting of the following: a halogen atom, a $C_{1-6}$ alkyl group, a halo-$C_{1-6}$ alkyl group, a hydroxy-$C_{1-6}$ alkyl group, a $C_{1-6}$ alkoxy group, and a cyano group, and
  t) a 5-membered aromatic heterocyclic group, in which the ring is unsubstituted or substituted with one to three groups independently selected from the group consisting of the following: a halogen atom, a $C_{1-6}$ alkyl group, a halo-$C_{1-6}$ alkyl group, a hydroxy-$C_{1-6}$ alkyl group, a $C_{1-6}$ alkoxy group, and a cyano group;
$R^3$ represents a halogen atom, a $C_{1-6}$ alkyl group, a halo-$C_{1-6}$ alkyl group, a hydroxy-$C_{1-6}$ alkyl group, a $C_{1-6}$ alkoxy group, a halo-$C_{1-6}$ alkoxy group, a $C_{1-6}$ alkylsulfanyl group, a $C_{3-6}$ cycloalkyl group, a cyano group, an amino group, or a nitro group;
$R^4$ represents a hydrogen atom, a halogen atom, a $C_{1-6}$ alkyl group, or a $C_{1-6}$ alkoxy group;
$R^5$ represents a hydrogen atom, a halogen atom, a $C_{1-6}$ alkyl group, or a $C_{1-6}$ alkoxy group;
$R^6$ represents a group selected from the group consisting of the following u) to x):
  u) a $C_{1-6}$ alkyl group,
  v) a halo-$C_{1-6}$ alkyl group,
  w) a $C_{3-6}$ cycloalkyl group, and
  x) a phenyl group, in which the ring is unsubstituted or substituted with one to five groups independently selected from the group consisting of the following: a halogen atom, a $C_{1-6}$ alkyl group, a halo-$C_{1-6}$ alkyl group, and a $C_{1-6}$ alkoxy group (with the proviso that the bonds with (*) represent binding to $Y^1$; and the bonds with (**) represent binding to $Y^2$).

2. The compound as claimed in claim 1 or a pharmaceutically acceptable salt thereof, wherein A represents a group selected from the group consisting of the following a), b), d), and h):

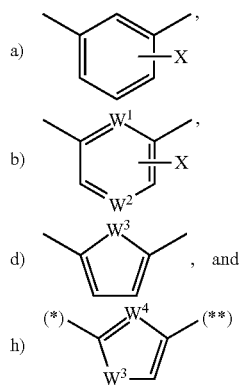

$Y^2$ represents a single bond; and
$R^5$ represents a hydrogen atom with the proviso that the bond with (*) represents binding to $Y^1$; and the bond with (**) represents binding to $Y^2$.

3. The compound as claimed in claim 2 or a pharmaceutically acceptable salt thereof, wherein A represents a group selected from the group consisting of the following a), b), and d):

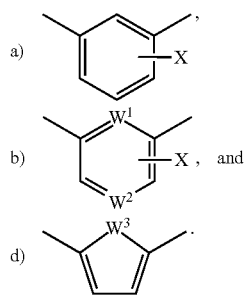

4. The compound as claimed in claim 3 or a pharmaceutically acceptable salt thereof, wherein $R^2$ is a group selected from the group consisting of the following o), r1), s1), and t1):
o) a branched $C_{3-6}$ alkyl group,
r1) a phenyl group, in which the ring is unsubstituted or substituted with one group selected from the group consisting of the following: a halogen atom, a $C_{1-6}$ alkyl group, a halo-$C_{1-6}$ alkyl group, and a $C_{1-6}$ alkoxy group,
s1) a 6-membered aromatic heterocyclic group, in which the ring is unsubstituted or substituted with one group selected from the group consisting of the following: a halogen atom, a $C_{1-6}$ alkyl group, a halo-$C_{1-6}$ alkyl group, and a $C_{1-6}$ alkoxy group, and
t1) a 5-membered aromatic heterocyclic group, in which the ring is unsubstituted or substituted with one group selected from the group consisting of the following: a halogen atom, a $C_{1-6}$ alkyl group, a halo-$C_{1-6}$ alkyl group, and a $C_{1-6}$ alkoxy group.

5. The compound as claimed in claim 4 or a pharmaceutically acceptable salt thereof, wherein $R^3$ represents a halogen atom, a $C_{1-6}$ alkyl group, a $C_{1-6}$ alkoxy group, or a $C_{3-6}$ cycloalkyl group.

6. The compound as claimed in claim 5 or a pharmaceutically acceptable salt thereof, wherein $R^1$ is a group selected from the group consisting of the following i) and m):
i) —C(=O)13 NH—SO$_2$—$R^6$; and
m) an acidic 5-membered hetero ring group.

7. The compound as claimed in claim 6 or a pharmaceutically acceptable salt thereof, wherein $R^1$ is —C(=O)—NH—SO$_2$—$R^6$.

8. The compound as claimed in claim 1, which is the compound selected from the following group, or a pharmaceutically acceptable salt thereof:
N-(methanesulfonyl)-6-(5-methoxy-2-phenylindol-1-ylmethyl)pyridine-2-carboxamide,
6-[6-fluoro-5-methoxy-2-(thiophen-3-yl)indol-1-ylmethyl]-N-(methanesulfonyl)pyridine-2-carboxamide,
6-(6-chloro-5-methoxy-2-phenylindol-1-ylmethyl)-N-(ethanesulfonyl)pyridine-2-carboxamide,
N-(ethanesulfonyl)-6-(5-methoxy-2-phenylindol-1-ylmethyl)pyridine-2-carboxamide,
5-methoxy-2-phenyl-1-[6-(1H-1,2,3,4-tetrazol-5-yl)pyridin-2-ylmethyl]-1H-indole,
5-methoxy-2-phenyl-1-[5-(1H-1,2,3,4-tetrazol-5-yl)furan-2-ylmethyl]-1H-indole,
6-chloro-5-methoxy-2-phenyl-1-[6-(1H-1,2,3,4-tetrazol-5-yl)pyridin-2-ylmethyl]-1H-indole,
6-fluoro-5-methoxy-1-[6-(1H-1,2,3,4-tetrazol-5-yl)pyridin-2-ylmethyl]-2-(thiophen-3-yl)-1H-indole,
6-[2-(butan-2-yl)-6-chloro-5-methoxyindol-1-ylmethyl]-N-(ethanesulfonyl)pyridine-2-carboxamide,
6-[2-(2,5-difluorophenyl)-5-methoxyindol-1-ylmethyl]-N-(ethanesulfonyl)pyridine-2-carboxamide,
6-[2-(butan-2-yl)-5-methoxyindol-1-ylmethyl]-N-(ethanesulfonyl)pyridine-2-carboxamide,
6-(5-methoxy-2-phenylindol-1-ylmethyl)-N-(propane-1-sulfonyl)pyridine-2-carboxamide,
6-(5-methoxy-2-phenylindol-1-ylmethyl)-N-(propane-2-sulfonyl)pyridine-2-carboxamide,
N-(cyclopropanesulfonyl)-6-(5-methoxy-2-phenylindol-1-ylmethyl)pyridine-2-carboxamide,
6-[2-(butan-2-yl)-5-methoxyindol-1-ylmethyl]-N-(propane-1-sulfonyl)pyridine-2-carboxamide,
6-[2-(butan-2-yl)-5-methhoxyindol-1-ylmethyl]-N-(propane-2-sulfonyl)pyridine-2-carboxamide,
6-[2-(butan-2-yl)-5-methhoxyindol-1-ylmethyl]-N-(cyclopropanesulfonyl)pyridine-2-carboxamide,
6-(6-fluoro-5-methoxy-2-phenylindol-1-ylmethyl)-N-(methanesulfonyl)pyridine-2-carboxamide,
N-(ethanesulfonyl)-6-(6-fluoro-5-methoxy-2-phenylindol-1-ylmethyl)pyridine-2-carboxamide,
6-(6-fluoro-5-methoxy-2-phenylindol-1-ylmethyl)-N-(propane-1-sulfonyl)pyridine-2-carboxamide,
N-(cyclopropanesulfonyl)-6-(6-fluoro-5-methoxy-2-phenylindol-1-ylmethyl)pyridine-2-carboxamide,
2-(butan-2-yl)-5-methoxy-1-[6-(1H-1,2,3,4-tetrazol-5-yl)pyridin-2-ylmethyl]-1H-indole,
6-fluoro-5-methoxy-2-phenyl-1-[6-(1H-1,2,3,4-tetrazol-5-yl)pyridin-2-ylmethyl]-1H-indole,
6-chloro-2-(furan-3-yl)-5-methoxy-1-[6-(1H-1,2,3,4-tetrazol-5-yl)pyridin-2-ylmethyl]-1H-indole,
5-methoxy-2-(1-methylcyclopropyl)-1-[6-(1H-1,2,3,4-tetrazol-5-yl)pyridin-2-ylmethyl]-1H-indole,
6-chloro-5-methoxy-2-(1-methylcyclopropyl)-1-[6-(1H-1,2,3,4-tetrazol-5-yl)pyridin-2-ylmethyl]-1H-indole, 5-methoxy-2-(1-methylcyclopropyl)-1-[5-(1H-1,2,3,4-tetrazol-5-yl)furan-2-ylmethyl]-1H-indole, 3-[6-(6-fluoro-5-methoxy-2-phenylindol-1-ylmethyl)pyridin-2-yl]-4,5-dihydro-1,2,4-oxadiazol-5-one, and N-cyano-6-(6-fluoro-5-methoxy-2-phenylindol-1-ylmethyl)pyridine-2-carboxamide.

9. A pharmaceutical composition comprising the compound as claimed in claim 1 or a pharmaceutically acceptable salt thereof.

10. The pharmaceutical composition as claimed in claim 9, comprising a combination of at least one agent selected from the group consisting of the following:

an anticholinergic agent, an $\alpha_1$ antagonist, a β agonist, a 5α-reductase inhibitor, a PDE inhibitor, an acetylcholine esterase inhibitor, an anti-androgen, a progesterone-based hormone, an LH-RH analog, a neurokinin inhibitor, an anti-diuretic, a calcium channel blocker, a direct smooth muscle agonist, a tricyclic antidepressant, a potassium channel modulator, a sodium channel blocker, an $H_1$ blocker, a serotonin reuptake inhibitor, a norepinephrine reuptake inhibitor, a dopamine reuptake inhibitor, a GABA agonist, a TRPV1 modulator, an endothelin antagonist, a $5\text{-HT}_{1A}$ antagonist, an $\alpha_1$ agonist, an opioid agonist, a $P_2X$ antagonist, a COX inhibitor, a σ agonist, and a muscarinic agonist.

11. An $EP_1$ receptor antagonist comprising the compound as claimed in claim 1 or a pharmaceutically acceptable salt thereof.

12. An agent for treating lower urinary tract symptoms, comprising the compound as claimed in claim 1 or a pharmaceutically acceptable salt thereof.

13. A method for treating lower urinary tract symptoms, comprising administering an effective amount of the compound as claimed in claim 1 or a pharmaceutically acceptable salt thereof.

* * * * *

SEQUENCE LISTING

```
<160> NUMBER OF SEQ ID NOS: 5

<210> SEQ ID NO 1
<211> LENGTH: 18
<212> TYPE: DNA
<213> ORGANISM: Artificial
<220> FEATURE:
<223> OTHER INFORMATION: 5' primer

<400> SEQUENCE: 1
ttggccactg atatgagc                                           18

<210> SEQ ID NO 2
<211> LENGTH: 18
<212> TYPE: DNA
<213> ORGANISM: Artificial
<220> FEATURE:
<223> OTHER INFORMATION: 3' primer

<400> SEQUENCE: 2
gctttgggca cattcaca                                           18

<210> SEQ ID NO 3
<211> LENGTH: 20
<212> TYPE: DNA
<213> ORGANISM: Artificial
<220> FEATURE:
<223> OTHER INFORMATION: 5' primer

<400> SEQUENCE: 3
caccactgat atgagcccct                                         20

<210> SEQ ID NO 4
<211> LENGTH: 19
<212> TYPE: DNA
<213> ORGANISM: Artificial
<220> FEATURE:
<223> OTHER INFORMATION: 3' primer

<400> SEQUENCE: 4
```
gcctagcttt gggcacatt                                            19

<210> SEQ ID NO 5
<211> LENGTH: 2414
<212> TYPE: DNA
<213> ORGANISM: Rattus norvegicus

<400> SEQUENCE: 5

| | | | | | |
|---|---|---|---|---|---|
| aacgccaata | gggactttcc | attgacgtca | atgggtggag | tatttacggt | aaactgccca      60 |
| cttggcagta | catcaagtgt | atcatatgcc | aagtacgccc | cctattgacg | tcaatgacgg     120 |
| taaatggccc | gcctggcatt | atgcccagta | catgacctta | tgggactttc | ctacttggca     180 |
| gtacatctac | gtattagtca | tcgctattac | catggtgatg | cggttttggc | agtacatcaa     240 |
| tgggcgtgga | tagcggtttg | actcacgggg | atttccaagt | ctccacccca | ttgacgtcaa     300 |
| tgggagtttg | ttttggcacc | aaaatcaacg | ggactttcca | aaatgtcgta | acaactccgc     360 |
| cccattgacg | caaatgggcg | gtaggcgtgt | acggtgggag | gtctatataa | gcagagctct     420 |
| ctggctaact | agagaaccca | ctgcttactg | gcttatcgaa | attaatacga | ctcactatag     480 |
| ggagacccaa | gctggctagt | taagcttggt | accgagctcg | gatccagtac | ccttcaccac     540 |
| tgatatgagc | ccctacgggc | ttaacctgag | cctagtggat | gaggcaacaa | cgtgtgtaac     600 |
| acccagggtc | cccaatacat | ctgtggtgct | gccaacaggc | ggtaacggca | catcaccagc     660 |
| gctgcctatc | ttctccatga | cgctgggtgc | tgtgtccaac | gtgctggcgc | tggcgctgct     720 |
| ggcccaggtt | gcaggcagac | tgcggcgccg | ccgctcgact | gccaccttcc | tgttgttcgt     780 |
| cgccagcctg | cttgccatcg | acctagcagg | ccatgtgatc | ccgggcgcct | tggtgcttcg     840 |
| cctgtatact | gcaggacgtg | cgcccgctgg | cggggcctgt | catttcctgg | gcggctgtat     900 |
| ggtcttcttt | ggcctgtgcc | cacttttgct | tggctgtggc | atggccgtgg | agcgctgcgt     960 |
| gggtgtcacg | cagccgctga | tccacgcggc | gcgcgtgtcc | gtagcccgcg | cacgcctggc    1020 |
| actagccctg | ctggccgcca | tggctttggc | agtggcgctg | ctgccactag | tgcacgtggg    1080 |
| tcactacgag | ctacagtacc | ctggcacttg | gtgtttcatt | agccttgggc | ctcctggagg    1140 |
| ttggcgccag | gcgttgcttg | cgggcctctt | cgccggcctt | ggcctggctg | cgctccttgc    1200 |
| cgcactagtg | tgtaatacgc | tcagcggcct | ggcgctcctt | cgtgcccgct | ggaggcggcg    1260 |
| tcgctctcga | cgtttccgag | agaacgcagg | tcccgatgat | cgccggcgct | ggggggtcccg   1320 |
| tggactccgc | ttggcctccg | cctcgtctgc | gtcatccatc | acttcaacca | cagctgccct    1380 |
| ccgcagctct | cggggaggcg | gctccgcgcg | cagggttcac | gcacacgacg | tggaaatggt    1440 |
| gggccagctc | gtgggcatca | tggtggtttc | gtgcatctgc | tggagccccc | tgctggtatt    1500 |
| ggtggtgttg | gccatcgggg | gctggaactc | taactccctg | cagcggccgc | tctttctggc    1560 |
| tgtacgcctc | gcgtcgtgga | accagatcct | ggacccatgg | gtgtacatcc | tgctgcgcca    1620 |
| ggctatgctg | cgccaacttc | ttcgcctcct | acccctgagg | gttagtgcca | agggtggtcc    1680 |
| aacggagctg | agcctaacca | agagtgcctg | ggaggccagt | tcactgcgta | gctcccggca    1740 |
| cagtggcttc | agccacttgt | gaatgtgccc | aaagctaggc | aagggtcaag | acaattctgc    1800 |
| agatatccag | cacagtggcg | gccgctcgag | tctagagggc | ccgcggttcg | aaggtaagcc    1860 |
| tatccctaac | cctctcctcg | gtctcgattc | tacgcgtacc | ggtcatcatc | accatcacca    1920 |
| ttgagtttaa | acccgctgat | cagcctcgac | tgtgccttct | agttgccagc | catctgttgt    1980 |
| ttgcccctcc | cccgtgcctt | ccttgaccct | ggaaggtgcc | actcccactg | tcctttccta    2040 |

-continued

```
ataaaatgag gaaattgcat cgcattgtct gagtaggtgt cattctattc tgggggtgg    2100 ggtggggcag gacagcaagg gggaggattg ggaagacaat agcaggcatg ctggggatgc    2160
ggtgggctct atggcttctg aggcggaaag aaccagctgg ggctctaggg ggtatcccca    2220
cgcgccctgt agcggcgcat taagcgcggc gggtgtggtg gttacgcgca gcgtgaccgc    2280
tacacttgcc agcgccctag cgcccgctcc tttcgctttc ttcccttcct ttctcgccac    2340
gttcgccggc tttccccgtc aagctctaaa tcgggggctc cctttagggt tccgatttag    2400
tgctttacgg cacc                                                     2414
```